(12) United States Patent
Ghadiri

(10) Patent No.: US 7,288,623 B2
(45) Date of Patent: Oct. 30, 2007

(54) CYCLIC PEPTIDE TUBE

(75) Inventor: Reza M. Ghadiri, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 728 days.

(21) Appl. No.: 10/196,937

(22) Filed: Jul. 17, 2002

(65) Prior Publication Data
US 2004/0024176 A1 Feb. 5, 2004

Related U.S. Application Data

(60) Division of application No. 08/632,444, filed as application No. PCT/US94/11620 on Oct. 14, 1994, now Pat. No. 6,613,875, which is a continuation-in-part of application No. 08/138,502, filed on Oct. 14, 1993, now abandoned.

(51) Int. Cl.
C07K 5/12 (2006.01)
A61K 38/12 (2006.01)

(52) U.S. Cl. .................. 530/321; 530/317; 530/345

(58) Field of Classification Search ............... 530/321, 530/317, 345
See application file for complete search history.

(56) References Cited

U.S. PATENT DOCUMENTS

| | | | |
|---|---|---|---|
| 4,102,877 A | 7/1978 | Nutt | |
| 5,041,533 A | 8/1991 | Wünsch et al. | |
| 5,169,862 A | 12/1992 | Burke, Jr. et al. | |
| 5,225,528 A | 7/1993 | Bock et al. | |

FOREIGN PATENT DOCUMENTS

FR 2 360 562 3/1978

OTHER PUBLICATIONS

Database Caplus, AN 1996:416696. Urry, D. Self-assembly of elastic protein-based polymers by the .DELTA.Tt-mechanism.*

(Continued)

*Primary Examiner*—Michael Borin
(74) *Attorney, Agent, or Firm*—Donald G. Lewis

(57) ABSTRACT

Cyclic homodetic peptides having a repeating D-L-chirality motif are shown to have a stable disk conformation with the amino acid side chains extending radially outward and the carbonyl and amino groups extending axially upward or downward. Such cyclic peptides can be employed as subunits in the assembly of molecular tubes. Cyclic peptides having a repeating D-L-chirality motif and lacking mutually repulsive side-chains are shown to stack atop one another in an anti-parallel fashion and are shown to be held together by the formation of β-sheet hydrogen bonding. The stacked cyclic peptides form a molecular tube having a central channel. The diameter of the channel is determined by the size cyclic peptide. If the cyclic peptide includes ionizable amino acid residues, e.g. glutamic acid or lysine, assembly and disassembly of the molecular tubes can be controlled by varying the pH. If the cyclic peptide includes hydrophobic amino acid residues, the molecular tube will insert into a lipid membrane. In such instances, the molecular tube provides a transmembrane channel. The channel can be gated or ungated. Molecular tubes can be terminated with a terminal cyclic peptide having methylated amino groups in one orientation. Molecular tubes may be employed as drug carriers, molecular sieves, reaction vessels, membrane channels, and other uses.

6 Claims, 32 Drawing Sheets

OTHER PUBLICATIONS

Javadpour et al. Database Caplus DN 127:136062 Biochemistry (1997), 36(31), 9540-9549.*

Khazanovich, et al., "Nanoscale Tubular Ensembles with Specified Internal Diameters. Design of a Self-Assembled Nanotube with a 13-A Pore", *J. Am. Chem. Soc.* 116:6011-6012 (1994).

Georger, et al., "Helical and Tubular Microstructures Formed by Polymerizable Phosphatidylcholines", *J. Am. Chem. Soc. 109*: 6169-6175 (1987).

Iijima, "Helical Microtubules of Graphitic Carbon", *Nature 354*: 56-58 (1991).

Ebbesen, et al., "Large-Scale Synthesis of Carbon Nanotubes", *Nature 358*: 220-222 (1992).

Fuhrhop, et al., "Molecular Monolayer Rods and Tubules Made of α-(L-Lysine),ω-(Amino) Bolaamphiphiles", *J. Am. Chem. Soc. 115*: 1600-1601 (1993).

Harada, et al., "Synthesis of a Tubular Polymer from Threaded Cyclodextrins", *Nature 364*: 516-518 (1993).

Ghadiri, et al., "Self-Assembling Organic Nanotubes Based on a Cyclic Peptide Architecture", *Nature 366*: 324-327 (1993).

Wang, "Encapsulation of Palladium Crystallites in Carbon and the Formation of Wormlike Nanostructures", *J. Am. Chem. Soc. 116*: 397-398 (1994).

Ghadiri, et al., "Artificial Transmembrane Ion Channels from Self-Assembling Peptide Nanotubes", *Nature 369*: 301-304 (1994).

Heitz, et al., "Conformations, cation binding, and transmembrane ion transfer properties of a cyclooctapeptide built by an alternation of D and L residues", *Int. J. Peptide and Protein Res. 34*: 387-393 (1989).

Heitz, et al., "Ionic Pores Formed by Cyclic Peptides", *Biochimie 71*: 71-76 (1989).

Tomasic, et al., "94. Some Cyclic Oligopeptides with $S_{zn}$ Symmetry", *Helv. Chim. Acta 70*: 1012-1016 (1987).

De Santis, et al., "Conformational Analysis of Regular Enantiomeric Sequences", *Macromolecules 7*: 52-58 (1974).

* cited by examiner

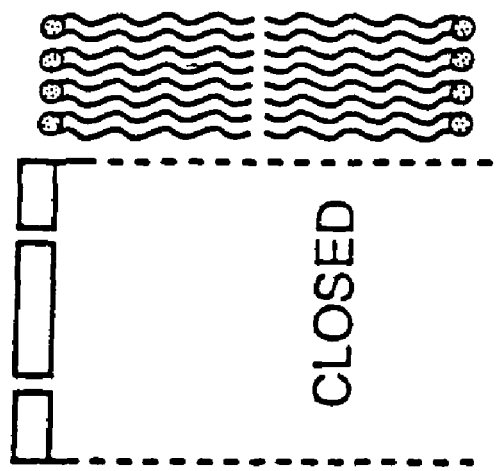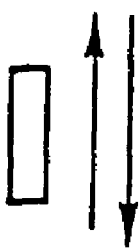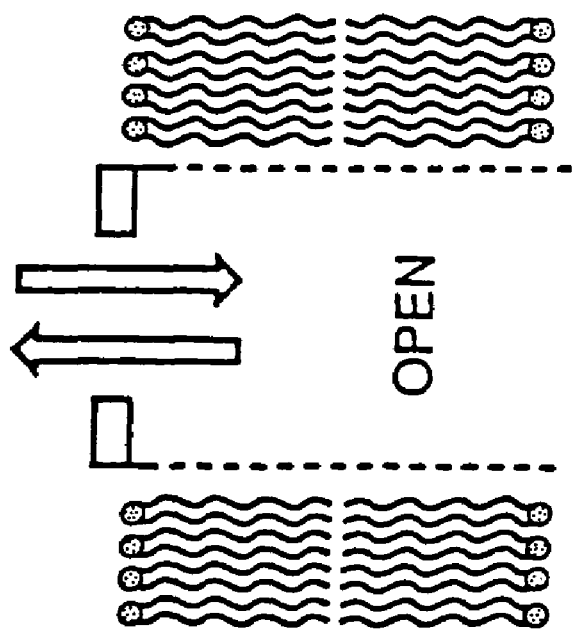
FIG. 5

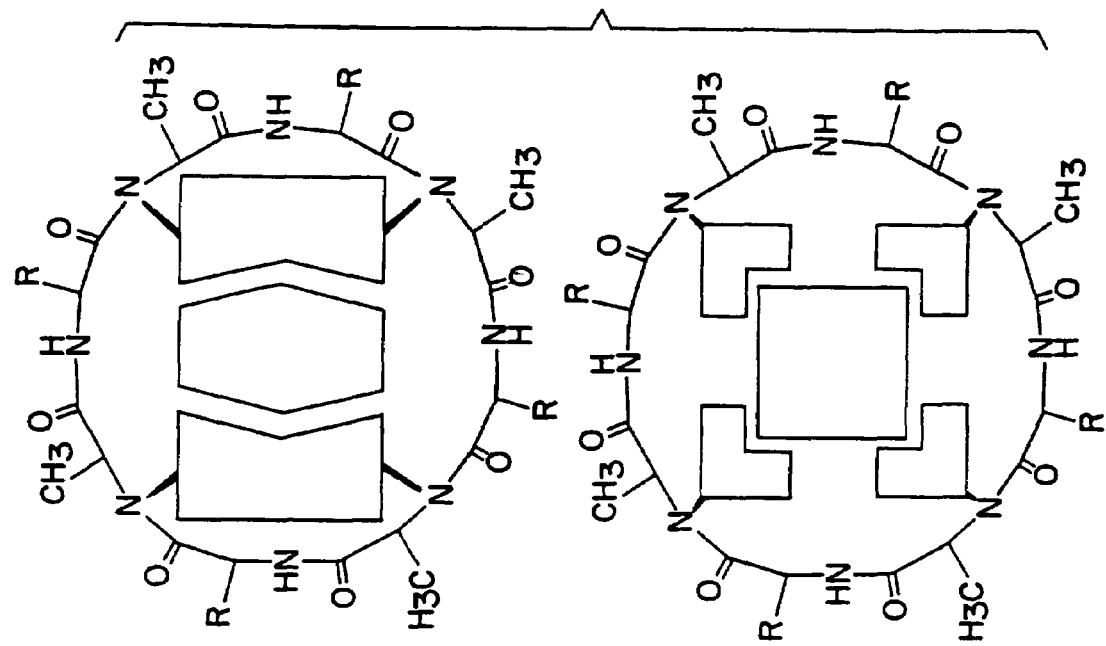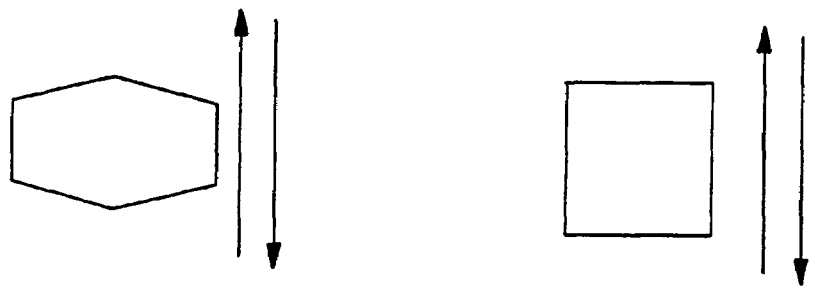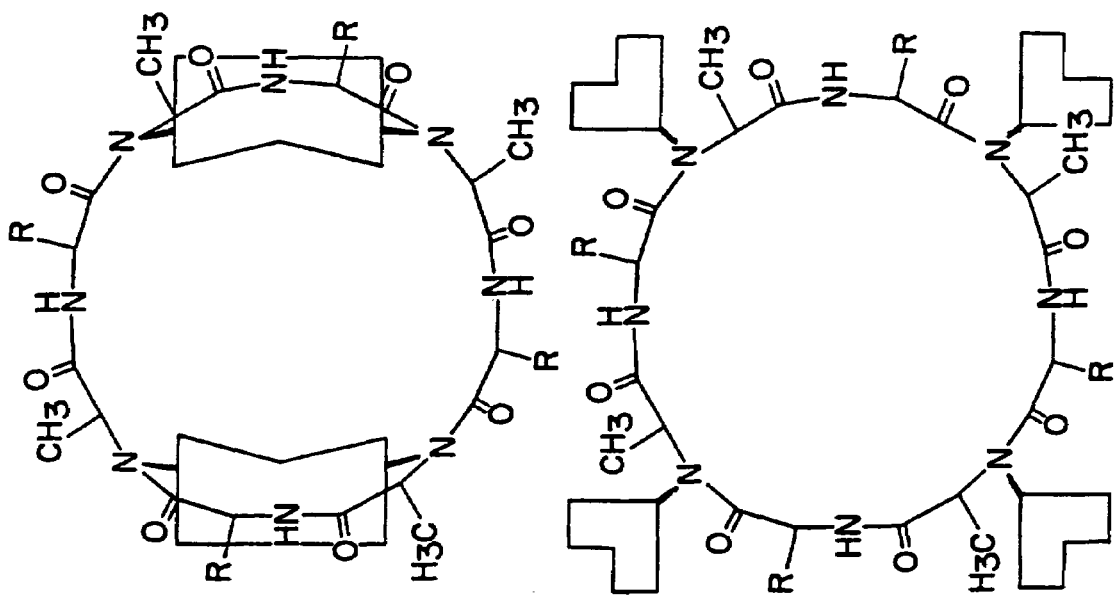
FIG. 6

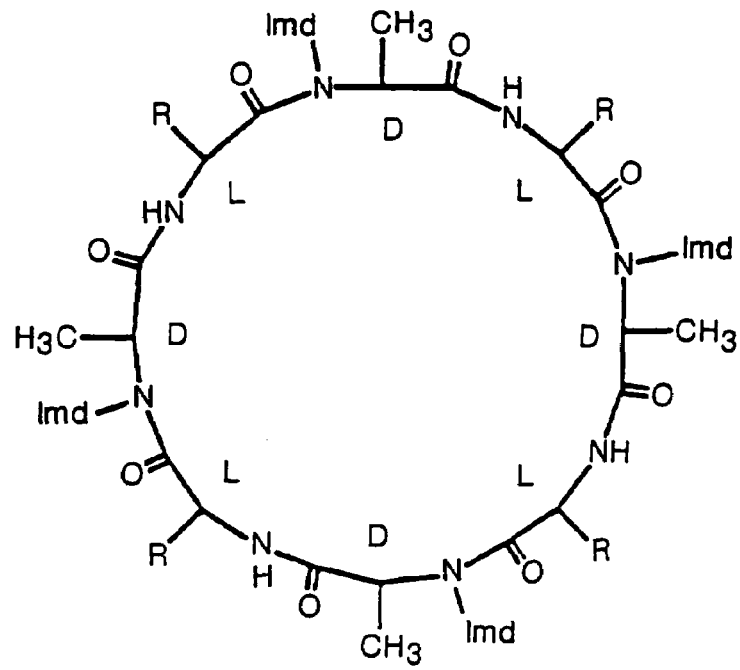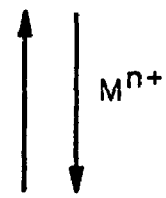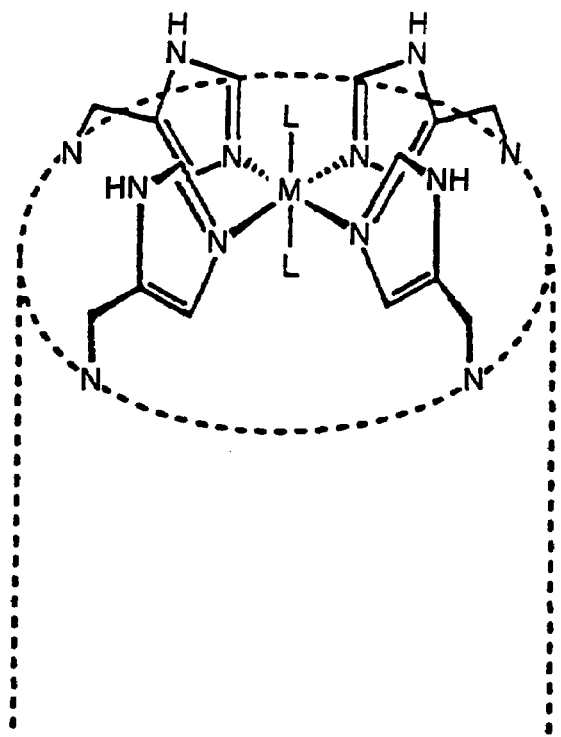
FIG. 8

FIG.II

CYCLIC PEPTIDE TUBE

This invention was made with government support under Contract No. N00014-94-1-0365 by the Office of Naval Research. The government has certain rights in the invention.

FIELD OF INVENTION

The invention relates to cyclic peptides and to molecular tube structures constructed from cyclic peptides. More particularly, the invention relates to the use of cyclic peptides having amino acid sequences with a repeating D-L-chirality motif employable for constructing self-assembling molecular tubes.

BACKGROUND

Cyclic peptides form a large class of natural and synthetic compounds. Naturally occurring cyclic peptides have diverse biological activities, e.g., antibiotics, toxins, hormones, and ion transport regulators. Naturally occurring cyclic peptides are not known to be synthesized via mRNA transcription, i.e., the amino acid sequence of naturally occurring cyclic peptides is not coded by the genome of the organism producing the material. Instead, the synthesis of naturally occurring cyclic peptides is dependent upon a series of non-transcriptional enzymes specifically dedicated to the synthesis of these products. Many cyclic peptides employ both amide and non-amide linkages and incorporate unnatural amino acids, i.e., amino acids not utilized in the mRNA transcriptional synthesis of linear proteins. Both D- and L-enantiomers of amino acids are widely employed in natural and synthetic amino acids synthetic analogs of several naturally occurring cyclic peptides have been designed and synthesized with modified biological activity.

Chemically, cyclic peptides are divided into two categories, i.e., homodetic peptides and heterodetic peptides. Homodetic peptides consist entirely of amino acid residues linked to one another by amide bonds. The present application is directed entirely to cyclic homodetic peptides. Heterodetic peptides include linkages other than amide linkages, e.g., disulfide linkages and ester linkages. Depsipeptides are a type of heterodetic peptide. Depsipeptides employ ester linkages. Valinomycin is a cyclic depsipeptide with an alternating chiral D-D-L-L-motif employing ester linkages within the ring. The present application specifically excludes heterodetic peptides. The chemistry of both homodetic and heterodetic cyclic peptides is extensively reviewed by Ovchinnikov et al. (1992), *The Proteins,* Vol. V: 307-642.

Molecular tubes are not previously known to be formed by cyclic peptides but are known to be formed by linear peptides. For example, gramicidin A is a linear pentadecapeptide having an alternating chiral D-L-motif. When integrated into a target bio-membrane, gramicidin A forms a left-handed anti-parallel double-stranded helix with 5.6-6.4 amino acid residues per turn. Gramicidin has an average outer diameter of approximately 16 Å and an average inner diameter of approximately 4.8 Å. The inner channel of gramicidin serves as a path for passive transmembrane ion transport. (See: Wallace, B. A. et al. (1988) *Science,* 44: 182-187; and Lang, D. (1988) *Science,* 44: 188-191.)

Molecular tubes may be formed from materials other that amino acids. Carbon tubes are disclosed by Iijima (*Nature* (1991), 354: 56-58) and Ebbesen et al. (*Nature* (1992), 358, 220-222). These carbon tubes are composed of graphite and have a concentric close ended structure. Inorganic tubes find wide application in chemistry, e.g., micro- and meso-porous inorganic solids known as zeolites are employed for enhancing a variety of reactions. The area of zeolites is reviewed by Meier et al., *Atlas of Zeolite Structure Types,* 2nd Edn (Butterworths, London, 1988).

What is needed is a method for assembling and disassembling molecular tubes of varying length and width using interchangeable subunits. What is needed is a versatile subunit for implementing the above method, i.e., a subunit which responds to a undergoes self-assembly and self-disassembly upon. What is needed is homodetic cyclic peptides which can be employed as subunits for self assembling and disassembling molecular tubes.

SUMMARY OF THE INVENTION

The invention includes cyclic homodetic peptides employable for assembling and disassembling molecular tubes, molecular tubes assembled from such cyclic homodetic peptides, and methods for assembling and disassembling such molecular tubes.

Cyclic homodetic peptides included within the invention have a stable disk conformation which facilitates the self-assembly of such peptides to form molecular tubes. A stable disk conformation is achieved by designing the cyclic peptides with a repeating D-L-chirality motif. Conformance with this repeating chirality motif necessitates that the amino acid sequence of the cyclic peptide include only an even number of amino acid residues. Since glycine lack chirality, conformance with this repeating chirality motif also necessitates that the amino acid sequence of the cyclic peptide exclude glycine or minimize the inclusion of glycine.

A stable disk conformation is further favored by limiting the size of the cyclic peptide, viz., the amino acid sequence of the cyclic peptide includes between 6 and 16 amino acid residues total. The stability of the disk conformation of cyclic peptides tends to decline with increasing ring size due to statistical mechanics considerations. Cyclic peptides with ring sizes greater than 16 residues are less preferred due to the low stability of their disk conformation.

Molecular tubes are assembled by stacking cyclic peptides atop one another. The resulting structure defines an interior channel. The diameter of the interior channel is determined by the size of the cyclic peptide, i.e., channel size increase with the size of the cyclic peptide. Cyclic peptides having only 6 amino acid residues have a very small channel suitable for the passage or inclusion of small ions only; cyclic peptides having 16 amino acid residues have a very large channel suitable for the passage or inclusion of small molecules; cyclic peptides having 16 amino acid residues have a very large channel suitable for the passage or inclusion of DNA or RNA.

The repeating D-L-chirality motif is thought to stabilize the disk conformation of cyclic homodetic peptides by lowering the energy of the outwardly oriented conformation of amino acid side chain grouts. In the outwardly oriented conformation, side chain groups of amino acid residues are oriented perpendicular to the axis of the disk in a radially outward direction orienting the amino acid side chains in this conformation also orients the backbone carboxyl groups and backbone amino hydrogens in a generally axial direction. Orienting the backbone carboxyl groups and backbone amino hydrogens in this axial direction predisposes cyclic peptides to stack atop one another in an anti-parallel fashion so as to form β-sheet hydrogen bonding.

The kinetics of assembly and disassembly cyclic peptide to form molecular tubes can be controlled by the selection of amino acid side chain groups. Cyclic peptides with ionizable amino acid side chains display pH dependent kinetics. Charged cyclic peptides are found to resist tube assembly; neutralized cyclic peptides are found to promote tube assembly. For example, cyclic peptides incorporating glutamic acid are found to spontaneously assemble into molecular tubes at acidic pH but resist assembly into molecular tubes at alkaline pH. Pre-assembled molecular tubes are found to spontaneously disassemble when the pH is raised from acid pH to alkaline pH. Judicious selection of amino acid side chains can promote packing or aggregation of molecular tubes to form tubular bundles.

Cyclic peptides composed entirely or largely of hydrophobic amino acid residues form molecular tubes within lipid bilayers. Such molecular tubes can span a membrane and provide an ion or molecular channel across such membrane. Such molecular tubes can be employed for loading cells or lipid vesicles with ions or molecules from the extra-vesicular space, depending upon the channel size of the tube. Transmembrane molecular tubes may also be gated so as to control the diffusion of ions and molecules through the channel.

Molecular tubes may be loaded with ionic or molecular inclusions within the channel space. If such tubes are loaded with a drug, the tubes may be employed as a drug delivery system. Release of the drug from molecular tubes may occur by diffusion or by tubular disassembly.

Molecular tubes may also be employed to facilitate the controlled growth of inorganic clusters, semiconductors, and atomic scale wires by means of tube assembly and/or diffusion within the tube channel to produce materials having novel optical and electronic properties.

BRIEF DESCRIPTION OF THE DRAWINGS

FIG. 3A illustrates a cyclic hexa-peptide having a channel diameter of approximately 7 Å.

FIG. 3B illustrates a cyclic octa-peptide having a channel diameter of approximately 10 Å.

FIG. 3C illustrates a cyclic dodeca-peptide having a channel diameter of approximately 15 Å.

FIG. 5 illustrates a schematic representation of a molecular tube having a gated channel.

FIG. 6 illustrates a schematic representation of a bidentatate (top) and a tetradentate gated channel.

FIG. 8 illustrates a membrane channel closed with respect to molecular transport mediated by $[M(Im)_4]^{B+}$ complex formation.

FIG. 18A is a low magnification image of a suspension of cyclic peptide tube particles, i.e., tube aggregates, adsorbed to carbon support film (scale bar=1 micron).

FIG. 18B is a low dose image of a frozen hydrated single particle of cyclic peptide tubes. The particle measures ~86× 1180 nm.

FIG. 18C is an enlarged image of the boxed region in FIG. 18B illustrating longitudinal striations with a resolution of approximately ~10 Å.

FIG. 18D is an image enhancement of FIG. 18 C illustrating 14.9 Å longitudinal striations representing side by side packing of cyclic peptide tubes in the particle (scale bar=10 nm).

FIG. 18E represents an electron diffraction pattern recorded from a single particle of cyclic peptide tubes showing orders of a 14.92 Å meridional spacing and a 4.73 Å axial spacing. Axially the pattern extends weakly to the third order (1.57 Å, data not shown) demonstrating that the particles are highly ordered and crystalline.

FIG. 19A are the infrared spectra of monomeric peptide subunit in $D_2O$ ($4 \times 10^{-3}$ M, pD=10, examined by attenuated total reflectance.

FIG. 19B is the infrared spectrum of particles of assembled cyclic peptide tubes (KBr pellet).

FIG. 19C is the FT-IR spectrum of N—H stretch region of particles of cyclic peptide tubes (KBr pellet). Components peaks are obtained by deconvolution of the original spectrum with single component, mixed Lorentzian and Gaussian functions using an iterative, linear least squares algorithm ("FIT", Galactic Industries Corp.).

DETAILED DESCRIPTION

Figure 1:
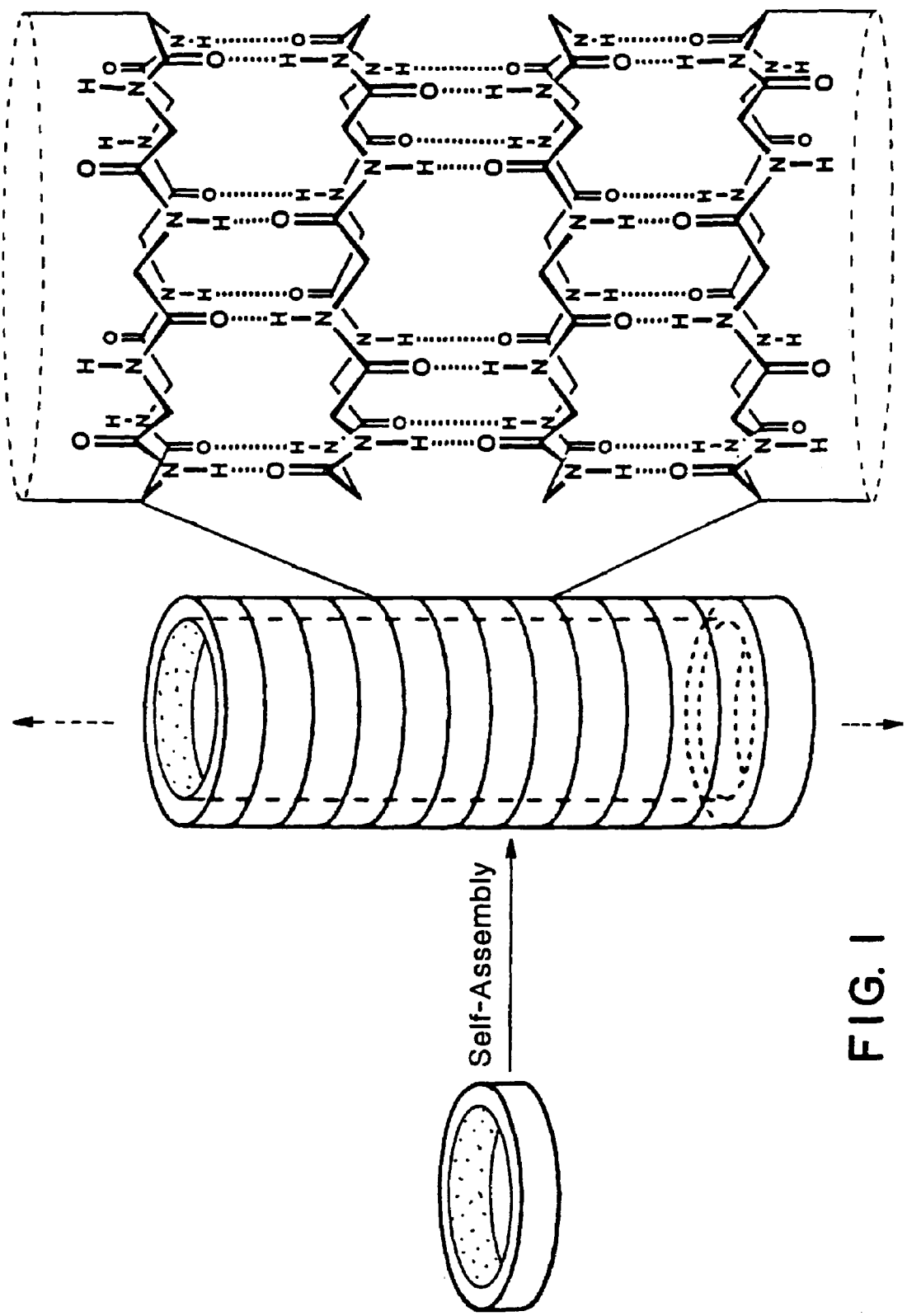
FIG. 1 is a schematic representation of a self-assembled molecular tube. Backbone-backbone hydrogen bonding interactions are shown but amino acid side chains are omitted for clarity. The internal diameter of the channel is determined by the ring size of the cyclic peptide subunits.

Self-Assembled Nanotube with a 7 to 8 Å Pore:

The design, synthesis, and characterization of a molecular tube, i.e., a cyclic peptide tube or "organic nanotube," is described. A rationally designed 24-membered ring peptide structure can be constructed and shown to undergo a proton-triggered self-assembly to produce tubular structures hundreds of nanometers long, with internal van der Waals diameter of 7 to 8 Å. Formation of tubular structures is established by Electron Microscopy (EM), electron diffraction studies, and Fourier Transformed Infrared Spectroscopy (FT-IR). A three-dimensional model of the molecular tube consistent with the experimental observations is also presented. As opposed to the recently identified closed concentric graphite tubes, cyclic peptide tubes, by virtue of the cyclic nature of their components, are open ended structures and have uniform shape and internal diameter, e.g., Tsang, S. C. et al. (1993), *Nature* 362, 520-522 and Ajayan, P. M. et al. (1993), *Nature* 362, 522-525 (1993). The proton-triggered self-assembly process described herein is a highly convergent approach in which numerous ring-shaped peptide subunits interact through an extensive network of hydrogen bonds to form molecular tube structures. Example I features an eight-residue cyclic peptide with the following sequence: cyclo[-(D-Ala-Glu-D-Ala-Gln)$_2$-]. (Sequence No.: 1) In designing the subunit, it is shown that cyclic peptides with an even number of alternating D- and L-amino acids can adopt or sample a low energy ring-shaped flat conformation in which all backbone amide functionalities lie approximately perpendicular to the plane of the structure. In this conformation, subunits can stack in an anti-parallel fashion and participate in backbone-backbone intermolecular hydrogen bonding to furnish a contiguous β-sheet structure. Moreover, because of the alternating D- and L-amino acid sequence, peptide side chains must \necessarily lie on the exterior of the ensemble thereby creating the desired hollow tubular core structure. In the present example, the ionization state of the glutamic acid side chain functionality is exploited as the trigger mechanism for the initiation of the self-assembly and self-disassembly processed in aqueous solutions. At alkaline pH, the large repulsive intermolecular electrostatic interactions between the negatively charged carboxylate side chains disfavors ring stacking and at the same time promotes the dissolution of the peptide subunit in aqueous media. However, upon protonation of the carboxylate moieties, not only does the unfavorable intermolecular electrostatic interactions vanish, but a multitude of attractive side chain-side chain hydrogen bonding interactions become operative. Furthermore, at acidic pH the peptide subunit displays lower solubility in aqueous media. This further contributes to an ordered phase transition toward self-assembled particles of cyclic peptide tubes. It is therefore concluded that since inter-subunit hydrogen bonding interactions provide the major driving force in the assembly process, and considering that only in the stacked configuration can the peptide subunits enjoy maximum possible number of hydrogen bonding contacts, protonation of the carboxylate moieties strongly biases the system toward self-assembly.

Figure 9A:
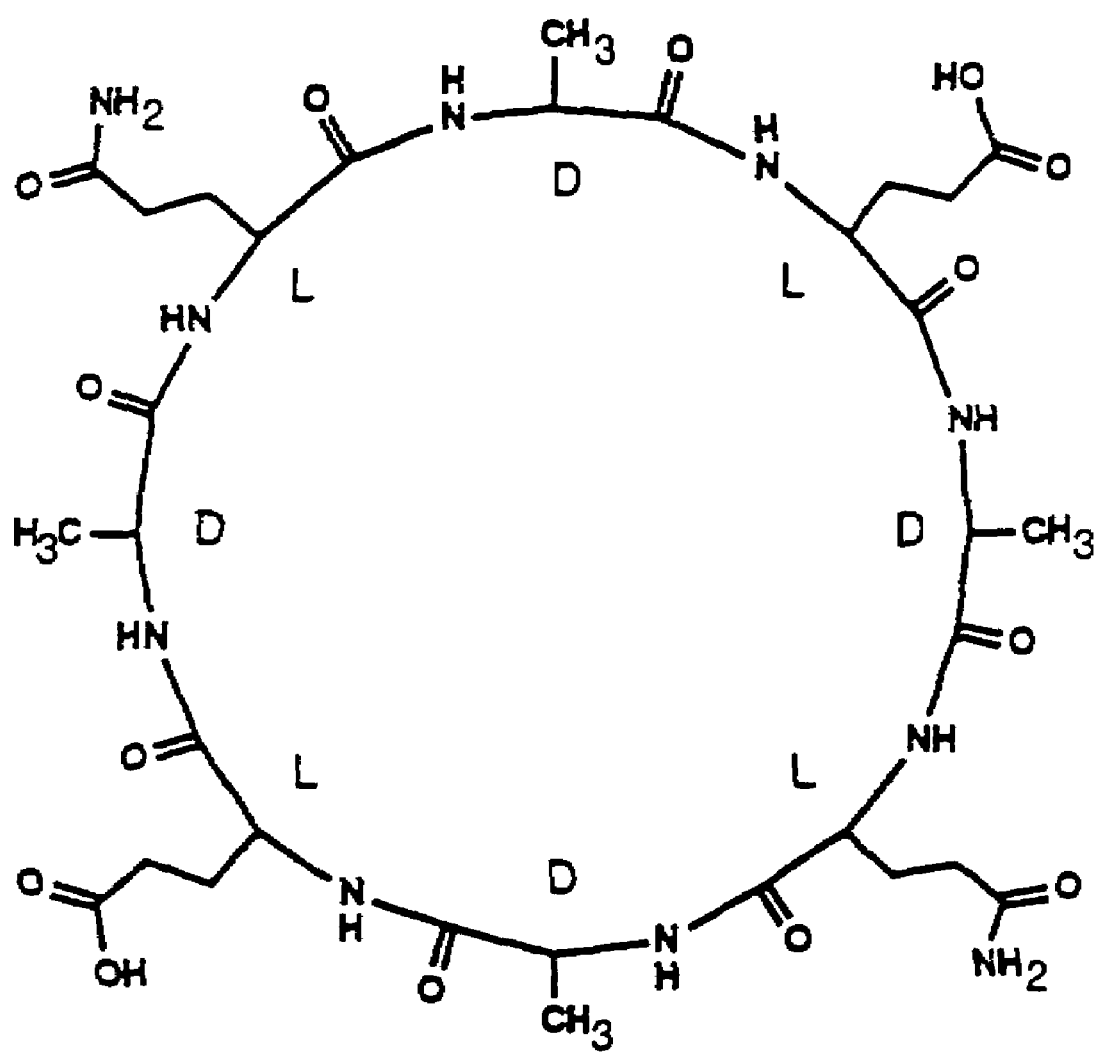
FIG. 9A illustrates the structure of cyclic peptide 1, i.e., an eight amino acid cyclic peptide having the amino acid sequence cyclo[-(Gln-D-Ala-Glu-D-Ala)$_2$-]. (Sequence No.: 1)
Figure 9B:
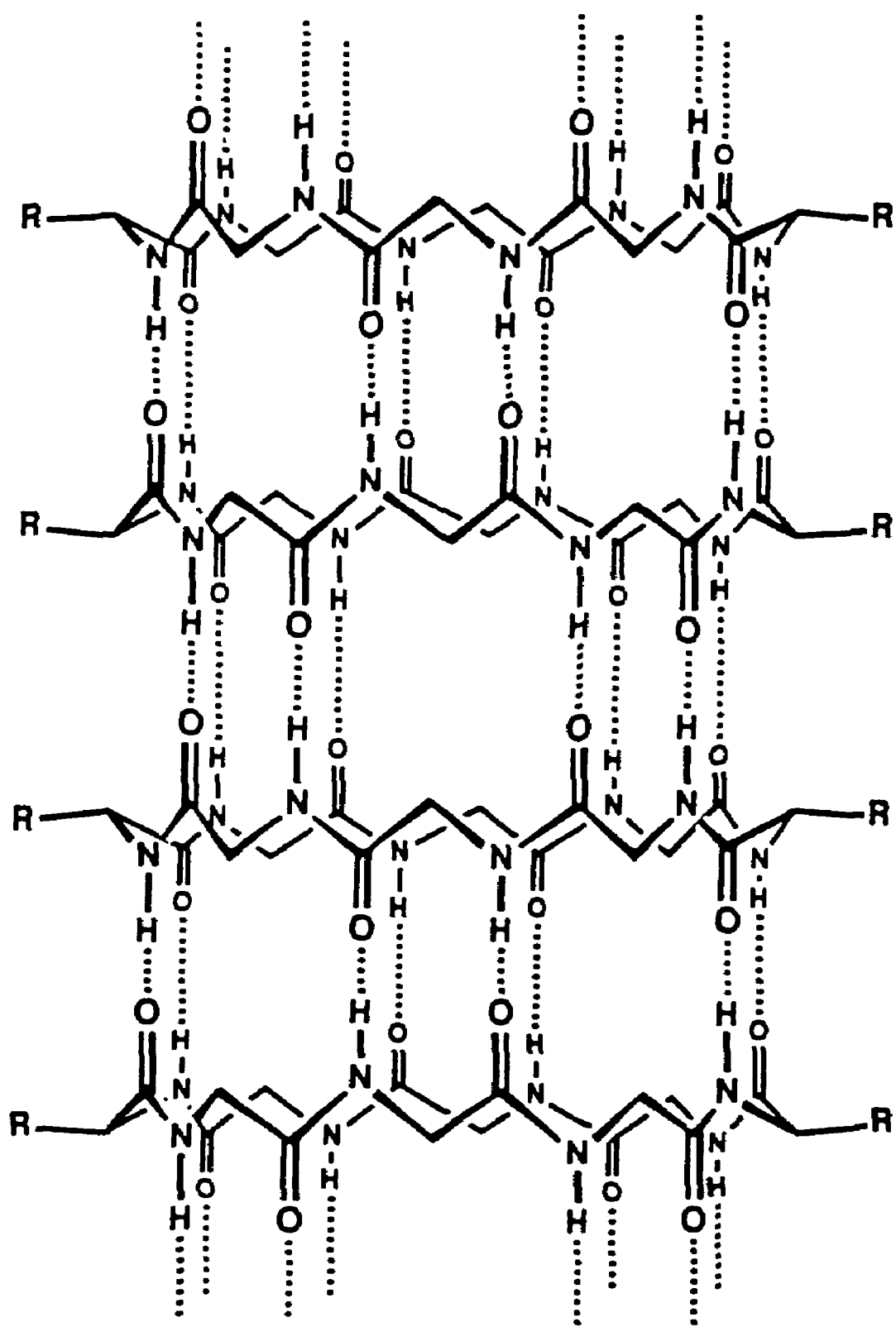
FIG. 9B illustrates a fragment of a molecular tube having four cyclic peptides of type 1.
Figure 10:
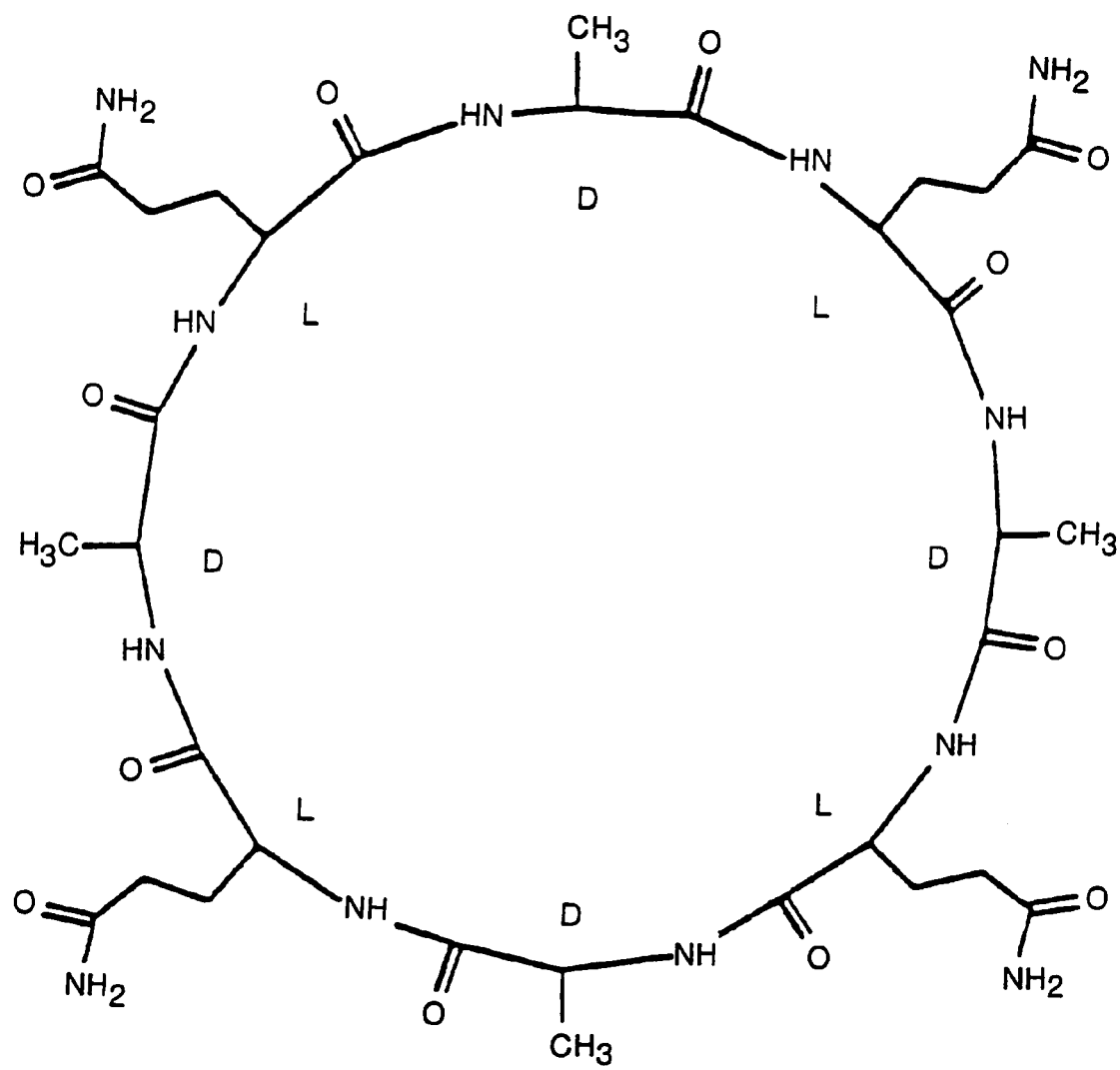
FIG. 10 illustrates the structure of cyclic peptide 2, i.e., an eight amino acid cyclic peptide having the amino acid sequence cyclo[-(Gln-D-Ala)$_4$-]. (Sequence No.: 2)
Figure 11:
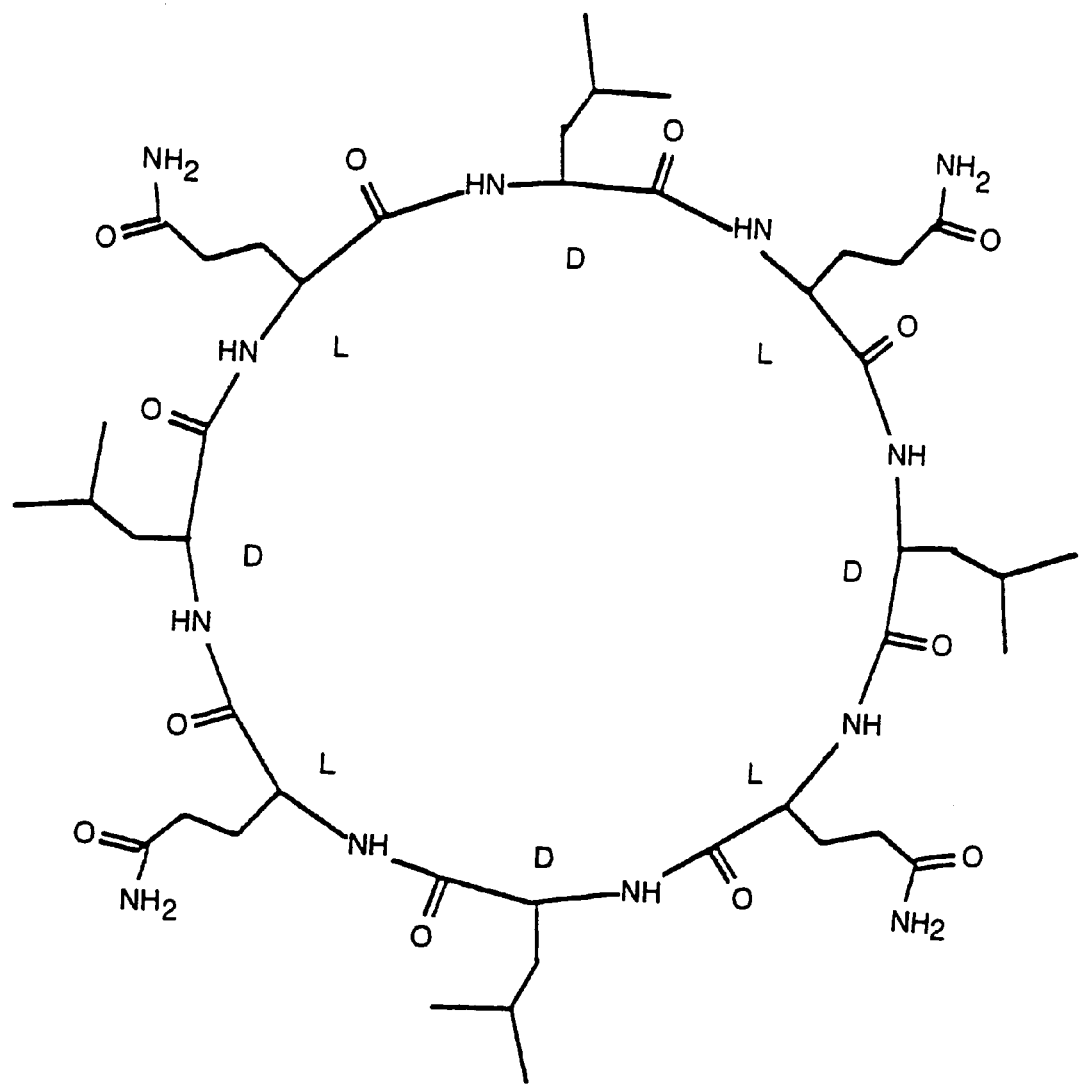
FIG. 11 illustrates the structure of cyclic peptide 3, i.e., an eight amino acid cyclic peptide having the amino acid sequence cyclo[-(Gln-D-Leu)$_4$-]. (Sequence No.: 3)
Figure 12:
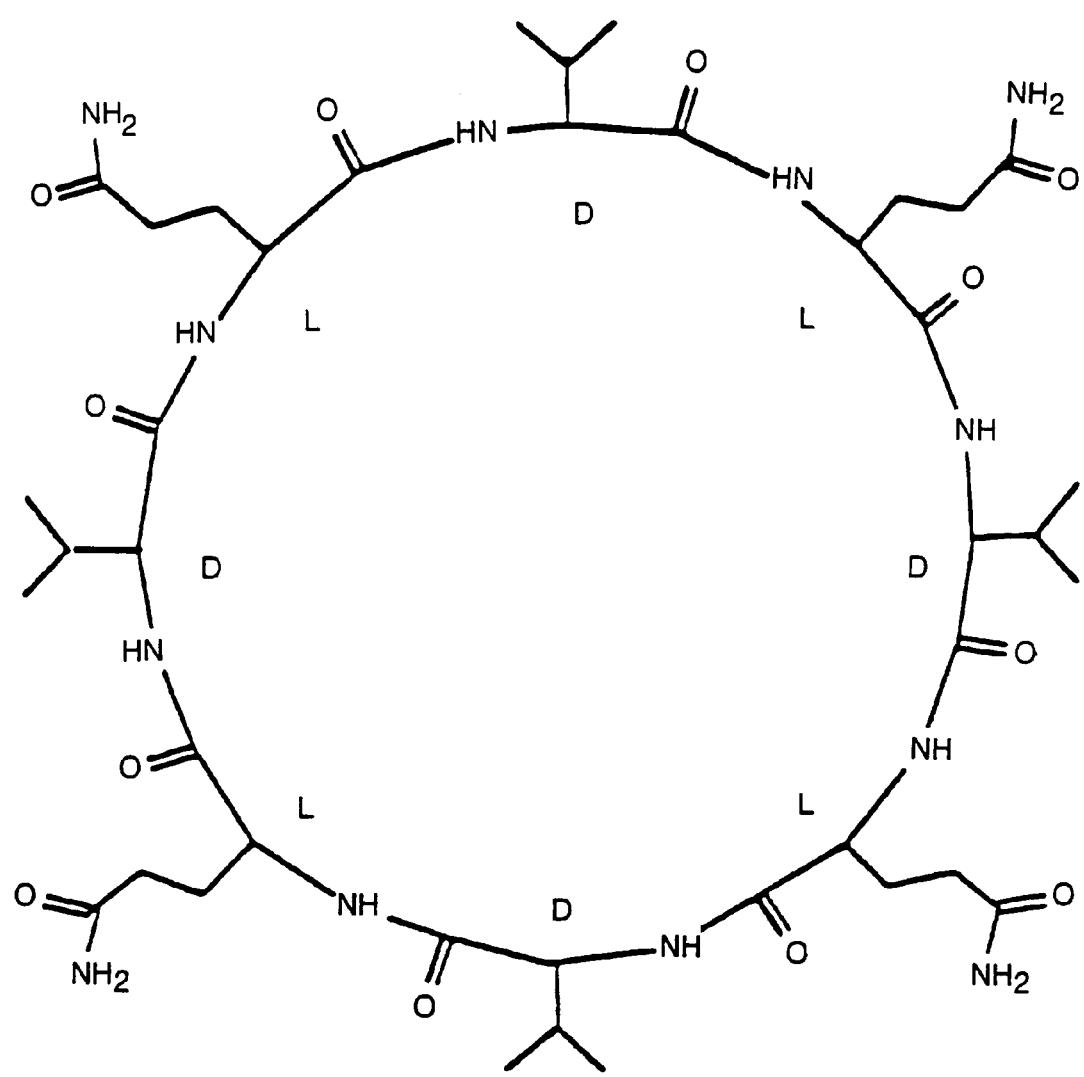
FIG. 12 illustrates the structure of cyclic peptide 4, i.e., an eight amino acid cyclic peptide having the amino acid sequence cyclo[-(Gln-D-Val)$_4$-]. (Sequence No.: 4)
Figure 13:
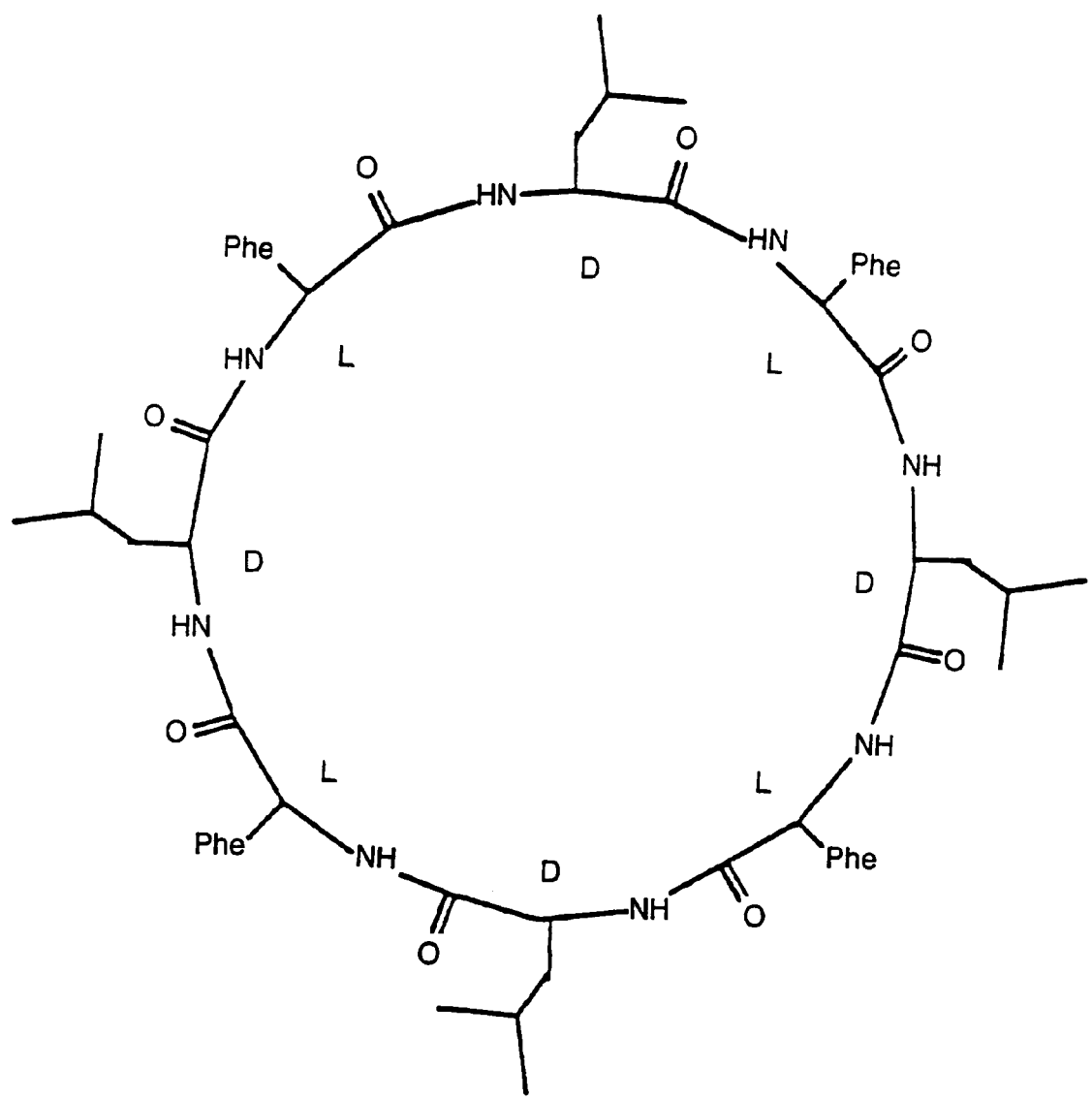
FIG. 13 illustrates the structure of cyclic peptide 5, i.e., an eight amino acid cyclic peptide having the amino acid sequence cyclo[-(Phe-D-Leu)$_4$]. (Sequence No.: 5)
Figure 14:
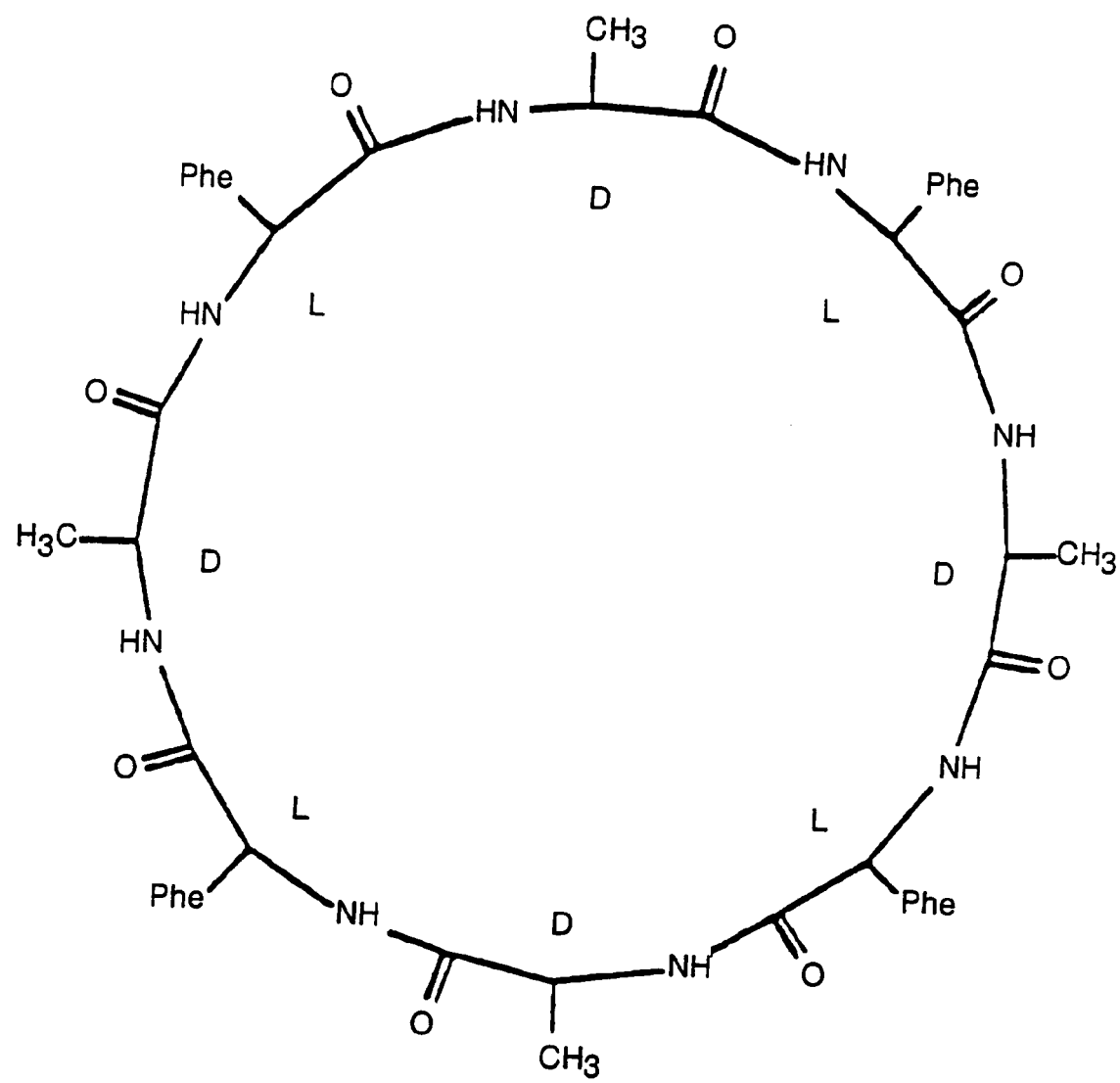
FIG. 14 illustrates the structure of cyclic peptide 6, i.e., an eight amino acid cyclic peptide having the amino acid sequence cyclo[-(Phe-D-Ala)$_4$-]. (Sequence No.: 6)
Figure 18A:
FIGS. 18A-E are micrographic images by electron microscopy and electron diffraction of cyclic peptide tubes.
Figure 18B:
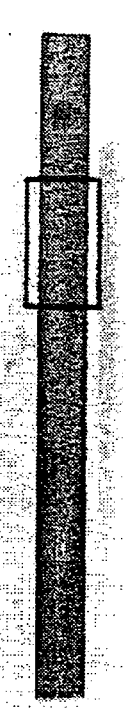
Figure 18C:
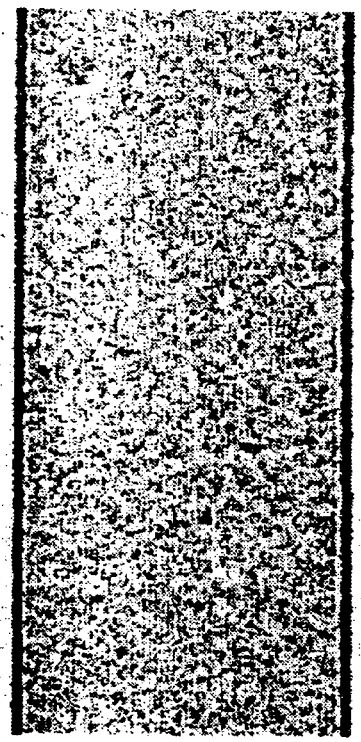
Figure 18D:
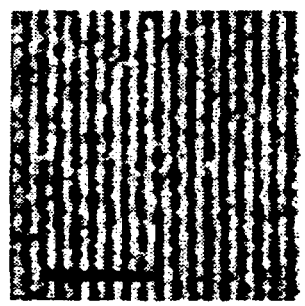
Figure 18E:
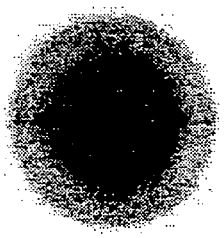

Controlled acidification of alkaline peptide solutions is disclosed to trigger spontaneous self-assembly of peptide subunits into rod-shaped crystals, as illustrated in FIGS. 18A and 18B. Transmission electron microscopy indicates that each particle is an orcanized bundle of hundreds of tightly packed cyclic peptide tubes. Low dose cryo microscopy of the particles reveals longitudinal striations with spacing of 14.9 Å along the long axis of the crystal, as expected, for the center to center spacing for closely packed cyclic peptide tubes, as illustrated in FIGS. 18C and D. As illustrated in FIG. 18E, electron diffraction patterns display 4.73 Å axial periodicity demonstrating that each cyclic peptide tube is made up of stacked rings with intersubunit distances corresponding to an ideal anti-parallel β-sheet structure as illustrated in FIG. 9B, e.g., Salemme, F. R. (1983) *Prog. Biophys. Molec. Biol.* 42, 95-133 and Stickle, D. F. et al. (1992), *J. Mol. Biol.* 226, 1143-1159. Given the thin rod shape of the crystals—on average 10 to 30 micron in length by 100 to 500 nanometer in width, it is reasonable to assume that crystals would lay on the supporting EM carbon film along the long axis and either of the eab or ac faces. However, all micrographs and diffraction patterns show similar diffraction intensities and nearly identical lattices. This suggests that the a and b axes are identical in size within experimental error. Furthermore, given the highly symmetric nature of the octapeptide, it seems reasonable that the similarity of the views reflects the symmetry of the molecule. Electron diffraction patterns showed a unit cell having a meridional spacing of 14.92±0.08 Å and an axial spacing of 4.73±0.02 Å with an angle of 99.2±0.5°. The diffraction patterns did not show any symmetry other than the center of symmetry due to Friedel's law. The patterns extend to 1.5 Å and occasionally to 1.2 Å indicating that the crystals are highly ordered. Considering the above observations, it follows that the lattice is trigonal with a=4.73 Å, b=c=15.1 Å, α=90°, and β=γ=99°.

Figure 20A:
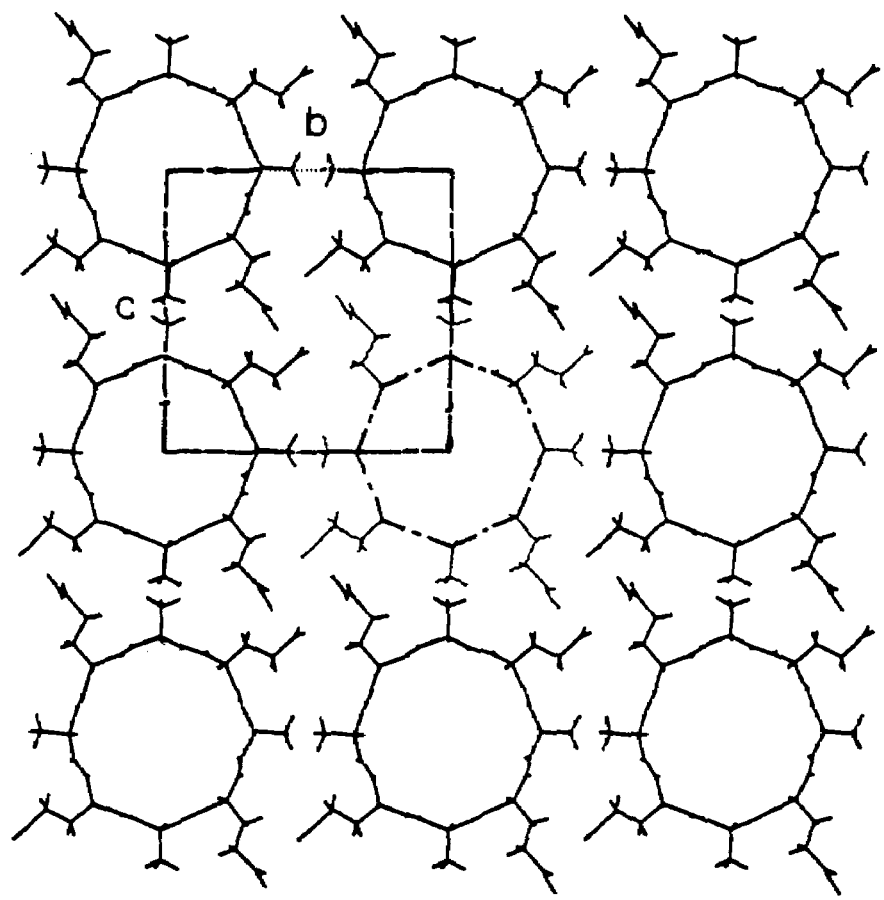
FIGS. 20A and B illustrate a three dimensional model of the self-assembled organic nanotubes formed by controlled acidification of cyclo[-(D-Ala-Glu-D-Ala-Gln)$_2$-] (Sequence No.: 1) into rod-shaped crystals, as illustrated in FIGS. 18A and 18B. View of the crystal packing along the a axis is shown in FIG. 20 A. View of the crystal packing along the c axis (bottom) is shown in FIG. 20B. The unit cell is indicated by the solid lines and the local two fold axis by the asterisk. The unit cell has dimensions a=9.5 Å, b=c=15.1 Å, and $\alpha$=90, $\beta$=$\gamma$=99 degrees. The tube axis is along a (x).
Figure 20B:
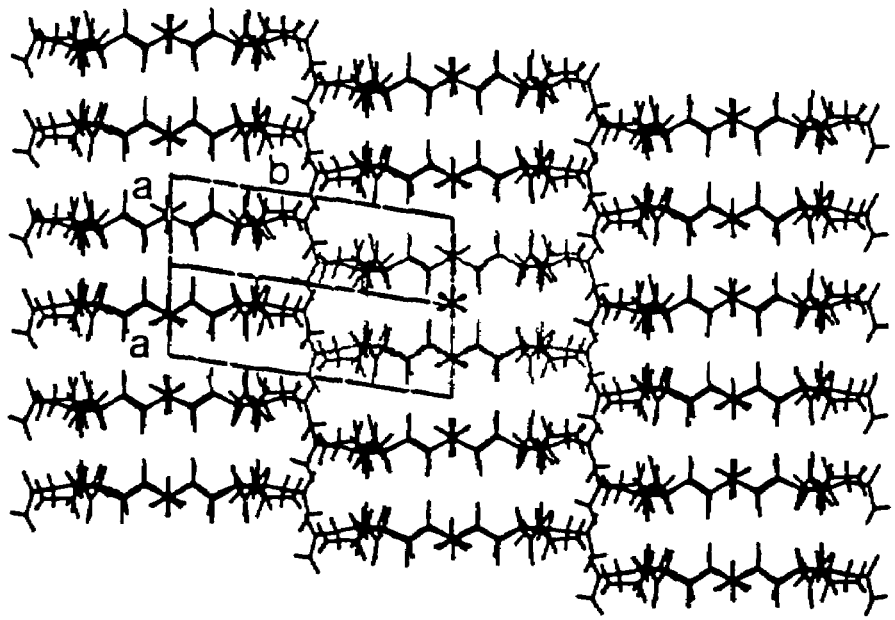
Figure 21A:
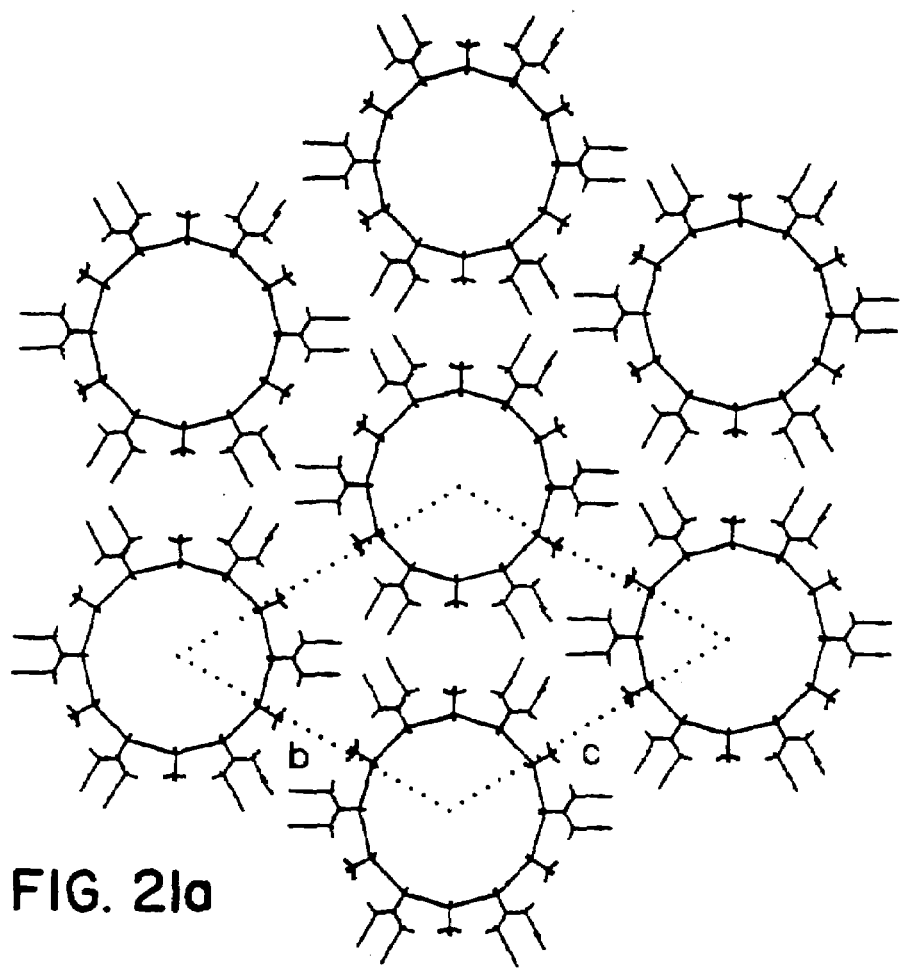
FIGS. 21A and B illustrate a three dimensional model of the self-assembled nanotubes formed by controlled acidification of cyclo[-(Gln-D-Ala-GluD-Ala)$_3$-] (Sequence No.: 8) into rod-shaped crystals, as illustrated in FIGS. 23. View of the crystal packing is shown along the a-axis (for clarity, each nanotube is represented only by the local 2-fold dimer) in FIG. 21A. View of the crystal packing is shown along the c-axis in FIG. 21 B. The unit cell is indicated by the dashed lines and the local 2-fold axis by the asterisk. The unit cell has the dimensions a=9.6 Å, b=c=25.66 Å, and $\alpha$=120, $\beta$=$\gamma$=99 degrees. The positions of the side chains in this model are arbitrary. The tube axis is along a (x).
Figure 21B:
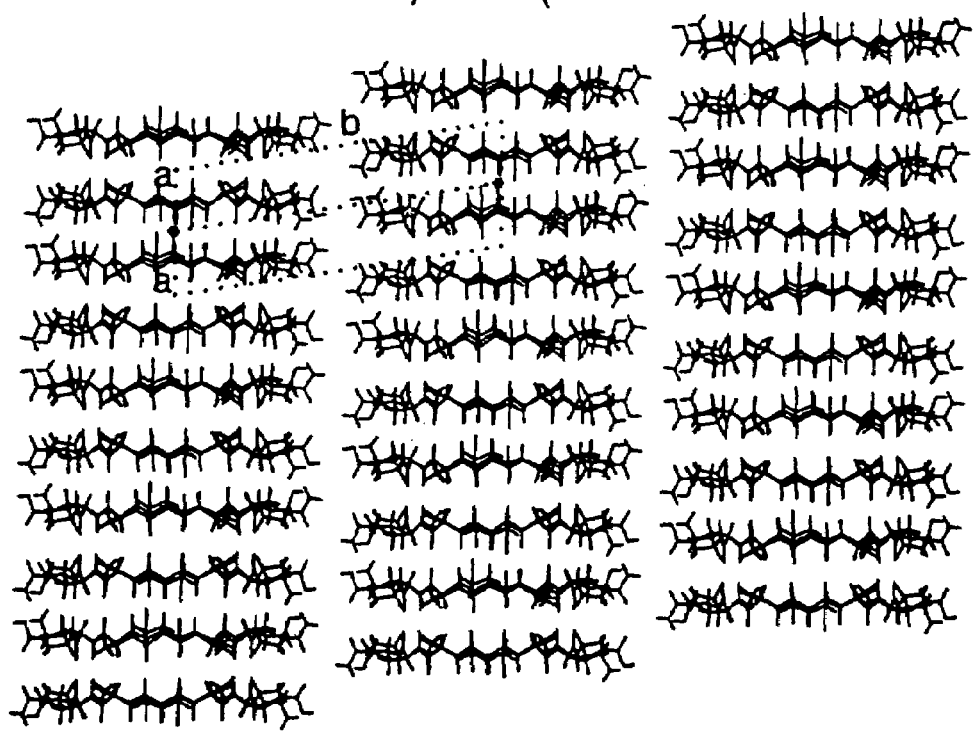

Although many conformers are possible using reasonable peptide backbone φ, ψ angles, only one fits the box defined by the unit cell-the disk-shaped flat conformation where all side chains extend out in the plane of the disk. Other conformations are puckered and the irregular presentation of side chains and backbone conformation prevent the packing of peptide subunits to within 4.7 Å due to prohibitive van der Waals contacts. The only way to pack two peptides to within 4.7 Å is to have the backbone carbonyl functionalities hydrogen bond intermolecularly to the nitrogen amide moieties of the opposite chain and position the side chains in the plane of the peptide backbone in order to avoid unfavorable side chain-side chain steric interactions. Furthermore, due to the use of alternating D- and L-amino acid residues, the most favorable intermolecular hydrogen bonds form when the disks are stacked on top of one another in an anti-parallel fashion giving rise to local two fold symmetry, as illustrated in FIG. 20. The model built in this way, using program XtalView disclosed by McRee, D. E. (1992) *J. Mol. Graphics* 10, 44-46, has unit cells which might at first glance seem twice as large—9.5×15.1×15.1—which would require a spacing of 9.4 Å in the diffraction pattern. However, when diffraction patterns are calculated every other level of h cancels out due to the pseudo-symmetry of the dimer. That is, the ring flipped over is nearly equivalent to the unflipped ring. Several other packing were tried but none were successful in forming a three-dimensional lattice without spacial overlaps and simultaneously fit the spacing indicated by the electron diffraction patterns. Cells where the local two-fold of the dimer is crystallographic were also considered but then the lattice could either not be modeled or the diffraction pattern had to have a mirror plane which of course is not observed. One other possibility is to consider that the observed diffraction pattern shows a diagonal of the lattice instead of a principle axis. This can be easily dismissed since it requires a substantially smaller unit cell. It should be pointed out that the volume of the unit cell in our proposed model is just large enough to contain the octapeptide and anything smaller can not physically hold the entire mass of the octapeptide. Therefore, the observed electron diffraction pattern must be due to the principle axis. Finally the crystalline model was checked for bad contacts using XPLOR, a program disclosed by Brunger, A. T. et al. (1987)

Science 235, 485 (molecular dynamics calculations on the three-dimensional crystalline lattice). No bad contacts were found and the overall energy of the model was low. Most importantly, when the three-dimensional model was used to calculate structure factors, the patterns produced compared very favorably with the electron diffraction patterns thus strongly supporting the efficacy of the proposed model.

Figure 19A:
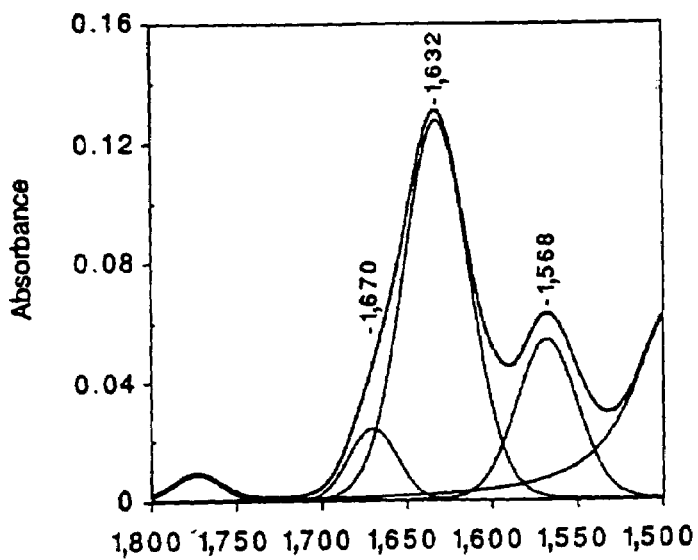
FIGS. 19A-C illustrate infrared spectra (at 8 $cm^{-1}$ resolution) of amide-I region.
Figure 19B:
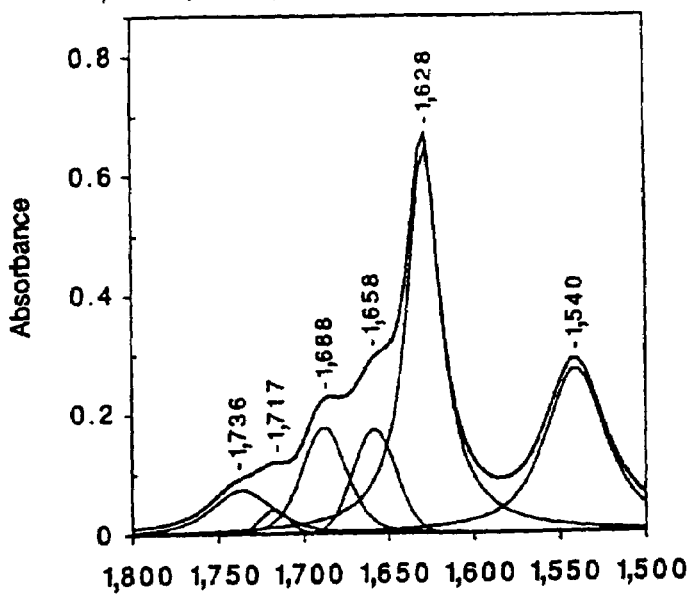
Figure 19C:
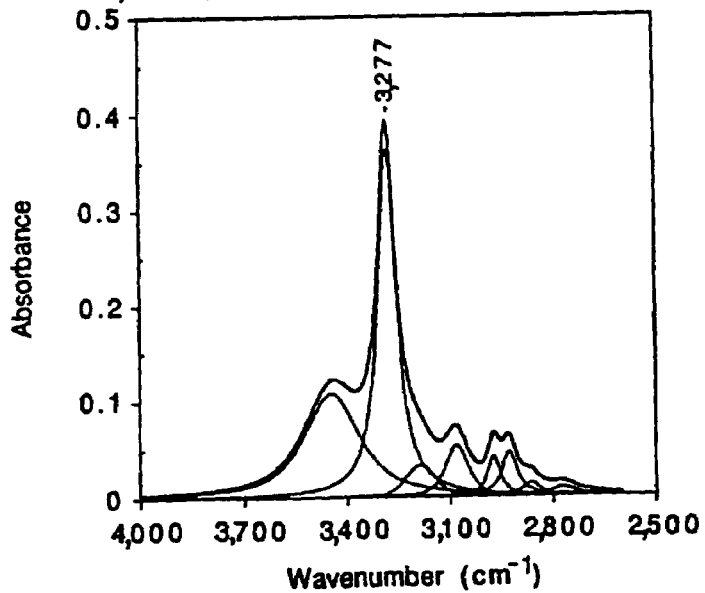

Involvement of intermolecular hydrogen bonding networks in tube assembly is also evident by FT-IR spectroscopic analysis[19], FIGS. 19A-C. In alkaline solutions, the monomeric peptide subunit displays an amide-I band at 1632 cm$^{-1}$ consistent with the cyclic structure of the backbone. Moreover, the bands at 1568 and 1670 cm$^{-1}$ are typical solvent exposed carbonyl stretching frequencies for glutamate and glutamine side chain functionalities, respectively. However, upon self-assembly, cyclic peptide tubes display characteristic features of a hydrogen bonded b-sheet structure. Not only is the appearance of amide I bands at 1628 and 1688 cm$^{-1}$ and the amide II band at 1540 cm cm$^{-1}$ consistent with the expected backbone structure, but the observed NH stretching frequency at 3277 cm$^{-1}$ also strongly supports formation of a tight network of backbone-backbone hydrogen bonding. Given the tight backbone-backbone intersubunit interactions, as determined by the above analysis of the electron diffraction patterns, it is possible to use Krimm's correlation to estimate intermolecular hydrogen bonding distance from the observed frequency of the N—H stretch, e.g., Krimm, S. et al., in *Advances in Protein Chemistry* (eds Anfinsen, C. B., Edsall, J. T. & Richards, F. M.) 181-364 (Academic Press, Orlando, 1986). The observed frequency of NH stretching mode approximately correlates to an average intersubunit N—O distance of 2.85 Å or an intersubunit distance of 4.71 Å. This value is in close agreement with the value of 4.73 Å obtained from electron diffraction patterns. It is noteworthy to point out that the IR spectrum of the cyclic peptide tubes also closely resemble the ones reported for Gramicidin A—a naturally occurring linear peptide composed of hydrophobic amino acids with alternating D- and L-configuration which is known to form dimeric b-helical transmembrane ion channel structures, e.g., Wallace, B. A. et al. (1988), *Science* 241, 182-187 and Langs, D. A. (1988), *Science* 241, 188-191. Gramicidin A has amide I bands at 1630, 1685 cm$^{-1}$, an amide II band at 1539 cm$^{-1}$, and an NH stretching frequency at 3285 cm$^{-1}$, consistant with Naik, V. M. et al. (1986), *Biophys. J.* 49, 1147-1154.

In summary, an example of a new class of synthetic tubular materials is disclosed. The general strategy described should allow for the design and synthesis of a wide range of tubular structures with specified internal diameters and surface characteristics. The availability of such a simple strategy for the design of open ended tubular structures should undoubtedly lend itself to a wide range of applications, e.g., Whitesides, G. M. et al. (1991), *Science* 254, 1312-1319 and ozin, G. A. (1992) *Adv. Mater.* 4, 612-649. Such tubular materials could be designed to mimic biological channels and pore structures, used to study physical and chemical properties of confined molecules, control growth and properties of inorganic and metallic clusters, or design novel optical and electronic devices.

Use of a Nanotube as a Carrier:

The cyclic peptide tubes disclosed in Example 1 may be assembled in the presence of hydrogen peroxide. After tube assembly and particle formation, the mixture is centrifuged in order to pellet the particles. The pelleted particles are washed by a further centrifugation step and then combined with the reagents of bioluminescent assay designed to test for the presence of hydrogen peroxide. Bioluminescence is seen to be confined to the pelleted fraction. This demonstrates that the cyclic peptide tubes can encapsulate hydrogen peroxide within their channel region but that the hydrogen peroxide slowly leaks by diffusion from such channel region into the external media.

Self-Assembled Nanotube with a 13 Å Pore:

The pore size of self-assembled organic nanotubes can be simply adjusted by the ring size of the peptide subunit employed. The internal diameter of the nanotube ensembles can be rigorously controlled simply by adjusting the ring size of the peptide subunit employed. A twelve-residue cyclic peptide structure, i.e., the thirty six-membered cyclic peptide subunit cyclo[-(Gln-D-Ala-Glu-D-Ala)$_3$-] (Sequence No.: 8) has been designed and shown to undergo a proton-induced self-assembly process to produce highly ordered nanotubular objects having a uniform 13 Å internal van der Waals diameter. These nanotubes have been characterized by IR spectroscopy, low-dose electron microscopy, and the analysis of electron diffraction patterns. The ability to design specifically sized tubular nanostructures is expected to have important applications in catalysis, inclusion chemistry, and molecular electronics. Formation of the tubular structures is supported by high resolution imaging using cryo electron microscopy, electron diffraction, Fourier-transform infrared spectroscopy, and molecular modeling.

Figure 22:
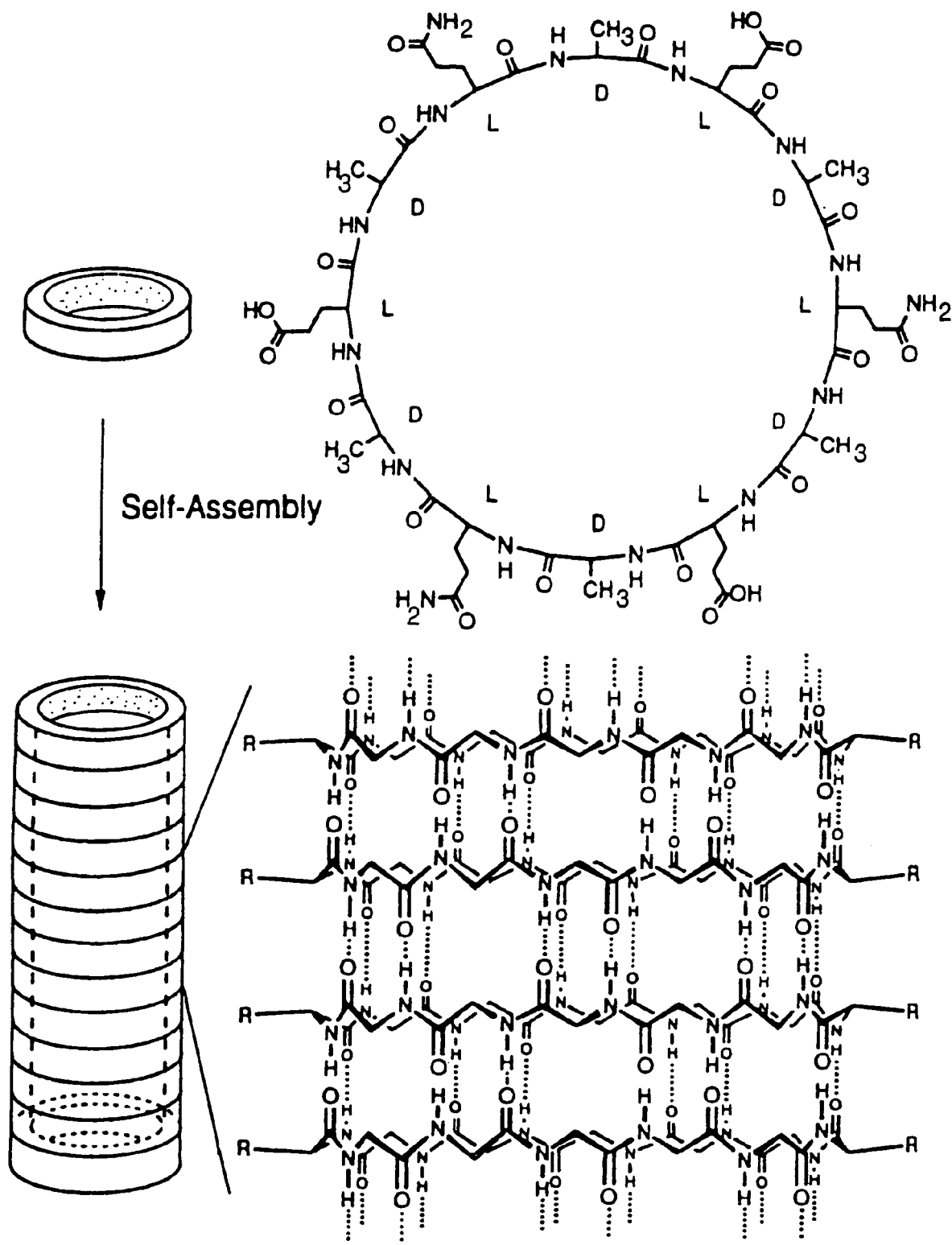
FIG. 22 illustrates a schematic representation of the strategy employed in the construction of self-assembled nanotubes of FIG. 21. Appropriately designed cyclic peptide subunits, under suitable conditions, stack to form hydrogen-bonded tubular structures (for clarity only backbone structure is represented). The ring size of the subunit sets the internal diameter of the tubular ensemble. The chemical structure of the subunit is shown on the top right (D or L refers to the amino acid chirality).
Figure 23A:
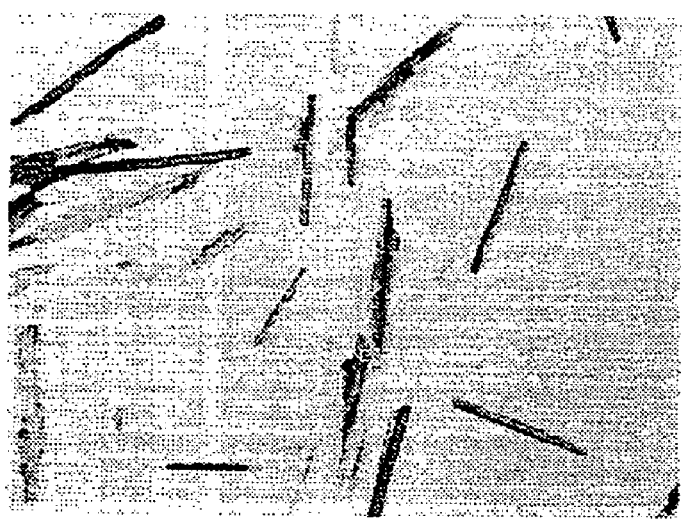
FIGS. 23A-B illustrates, on the left, a low magnification electron micrograph of nanotube suspensions of FIG. 21 adsorbed on carbon support film (Scale bar, 1 mm) and, on the right, low-dose image of a frozen hydrated single nanotube particle. Longitudinal striations which are approximately 25 Å apart are due to the side-by-side packing of nanotubes.
Figure 23B:
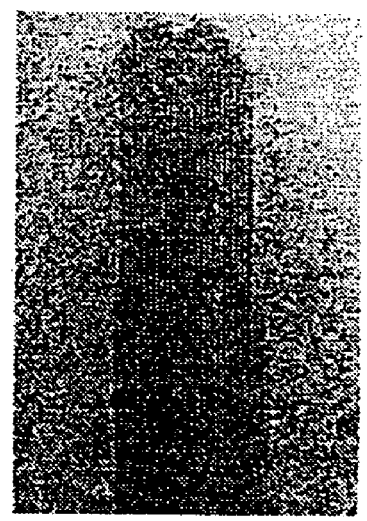

According to the disclosed design principles, cyclic peptide structures which are made up of an even number of alternating D- and L-amino acid residues can adopt or sample a flat ring-shaped conformation in which all backbone amide functionalities lie approximately perpendicular to the plane of the ring structure. In this conformation, the peptide subunits can stack, under favorable conditions, to furnish a contiguous hydrogen bonded hollow tubular structure (FIG. 22). The internal diameter of the nanotube ensemble can, in principle, be tailored by adjusting the ring size of the peptide subunit employed. In this study we will describe the largest pore diameter peptide-based nanotube structure thus far constructed by utilizing the following thirty six-membered ring peptide subunit cyclo[-(Gln-D-Ala-Glu-D-Ala)$_3$-]. The design principles and the self-assembly strategy employed in this study is similar to the one described previously[1]. The requisite peptide subunit was synthesized on a solid-support, according to the method of P. Rovero et al. (*Tetrahedron Lett.*, (1991), vol. 32, pages 2639-2642) and characterized by mass spectrometry and $^1$H NMR spectroscopy. Controlled acidification of alkaline solutions of the peptide subunit upon standing afforded rod shaped crystalline materials, as indicated above. Transmission electron microscopy indicates that each particle is an organized bundle of tightly packed nanotubes (FIGS. 23A-B). Low dose cryo microscopy, according to the method of M. Adrian et al. (*Nature* (1984), vol. 308, pages 32-36) and of R. A. Milligan et al. (*Ultramicroscopy* (1984), vol. 13, pages 1-10) revealed longitudinal striations with spacing of approximately 25 Å as expected for the center to center spacing for closely packed nanotubes (FIGS. 23A-B). Electron diffraction patterns display axial spacing of 4.80 Å which is in agreement with the peptide stacking and the formation of tight network of hydrogen bonded b-sheet type structure. The Meridonial spacing in the electron diffraction patterns display spacing of 12.67±0.06 Å and 21.94±0.05 Å characteristic of a hexagonal body centered packing of nanotubes. Hexagonal lattice resulting from the close packing of cylinders of radius r displays the characteristic two principle lattice planes of radius r and r such as the one observed here (r=12.67 Å and r=21.94 Å). The periodicity in this packing produces diffraction spots at 1/r, 2/r, and so on, and at 1/r, and 2/r, and so on. The observed electron diffraction patterns on the meridional axes extend to third order reflections (4.1 Å) signifying the ordered and crystalline state of the nanotube particles. The diffraction patterns also showed a unit cell with an angle of 99° and no other symmetry than the center of symmetry due to Friedel's law.

A three-dimensional model of the nanotube structure was built using the parameters obtained from the electron diffraction patterns-unit cell with a=9.6 Å (2×4.80 Å for the antiparallel dimer), b=c=25.66 Å (2×12.67÷ cos 9), α=120°, and β=γ=99°. The model shows structure factors similar to the patterns observed in the electron diffraction thus supporting the proposed three-dimensional model. Involvement of intermolecular hydrogen bonding network in the tube assembly is also supported by FT-IR spectroscopic analysis according to the method of S. Krimm et al. (*Advances in Protein Chemistry*; Anfinsen, C. B., Edsall, J. T.; Richards, F. M. Eds.; Academic Press: Orlando, 1986, pages 181-364). Nanotubes display characteristic IR features of a β-sheet structure signified not only by the amide I bands at 1626 $cm^{-1}$ and 1674 $cm^{-1}$ and an amide II band at 1526 $cm^{-1}$, but also by the observed NH stretching frequency at 3291 $cm^{-1}$ supporting formation of a tight network of hydrogen bonds. The IR spectrum is very similar to other nanotubes and closely resembles that of crystalline Gramicidin A which is known to form dimeric β-helical structures. Gramicidin A has amide I bands at 1630, 1685 $cm^{-1}$, an amide II band at 1539 $cm^{-1}$, and an NH stretching frequency at 3285 $cm^{-1}$. (V. M. Naik et al. in *Biophys. J.* (1986), vol. 49, pages 1147-1154.) The observed frequency of NH stretching mode correlates to an average intersubunit distance of 4.76 Å which is in close agreement with the value of 4.80 Å obtained independently from the electron diffraction patterns.

Artificial Transmembrane Ion Channels from Self-Assembling Peptide Nanotubes:

Artificial membrane ion channels may be constructed using self-assembled cylindrical β-sheet peptide architecture. The construct described displays an efficient channel-mediated ion transport activity with rates exceeding $10^7$ ions.$sec^{-1}$ rivaling that of many naturally occurring counterparts. Such molecular assemblies are expected to have potential utility in the design of novel cytotoxic agents, membrane transport vehicles, and drug delivery systems.

Figure 2:
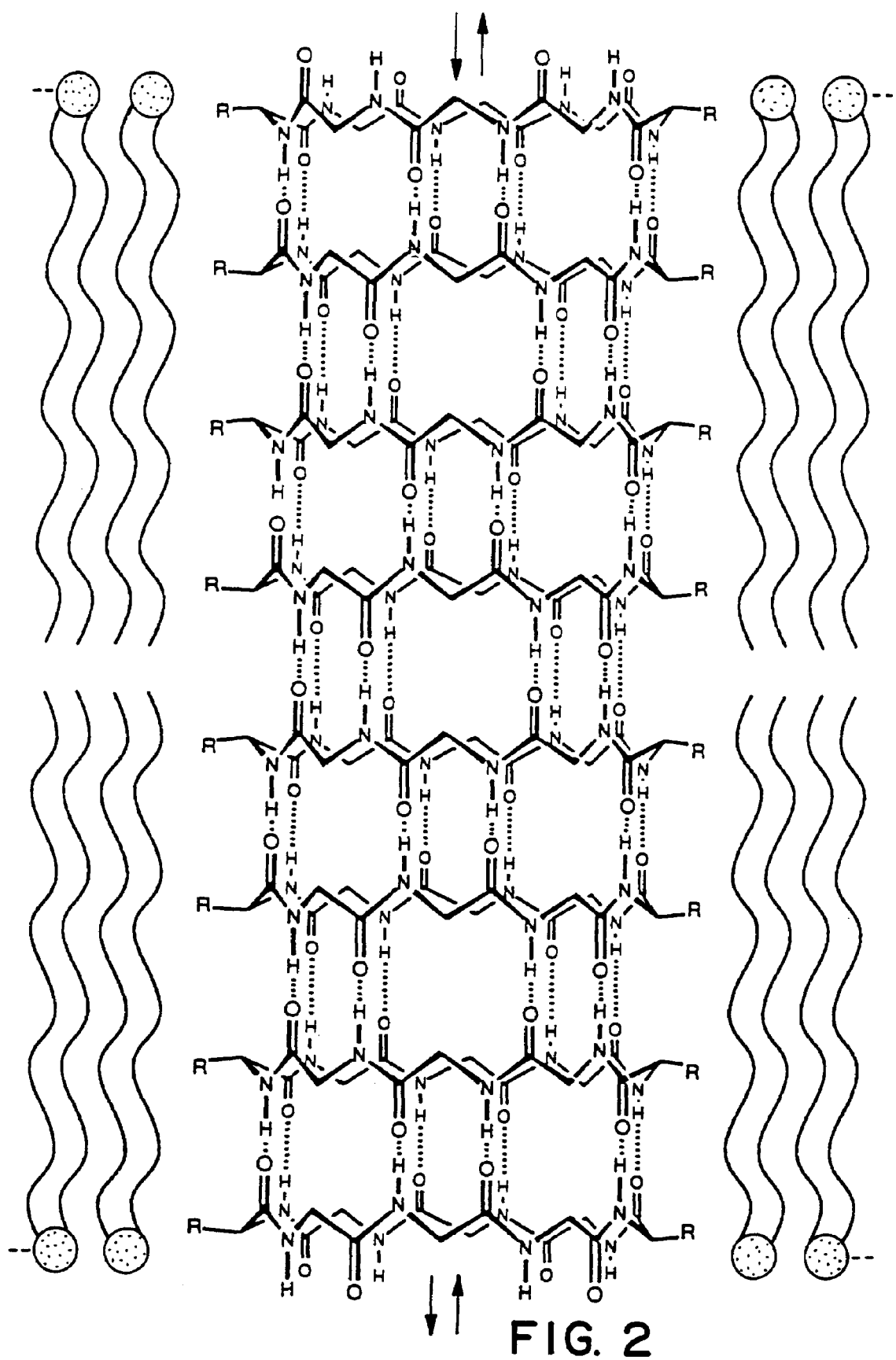
FIG. 2 illustrates a molecular tube having eight cyclic peptides of the type having eight hydrophobic amino acids each, such as cyclic peptides 5 and 6. The molecular tube traverses a lipid bilayer to provide a channel, indicated by arrows, across the lipid bilayer.

According to the design principles herein disclosed, cyclic peptide structures made up of an even number of alternating D- and L-amino acid residues can adopt a flat ring conformation and stack, under favorable conditions, to furnish a contiguous hydrogen bonded hollow tubular structure. Therefore, an ensemble made up of eight to ten subunits, each separated by the expected intersubunit distance of 4.7 to 5.0 Å and decorated with appropriate hydrophobic surface residues, would be long enough to span the thickness of average biological lipid membranes (FIG. 2). The eight residue cyclic peptide cyclo[-(Trp-D-Leu)$_3$-Gln-D-Leu-] (Sequence No.: 9) was designed for the purpose in hand. It is composed of alternating L-tryptophan and D-leucine side chain moieties with the exception of one L-glutamine residue introduced mainly to simplify the peptide synthesis. It is demonstrated that the channel structures having an aqueous pore of approximately 7.5 Å in diameter would form spontaneously upon incorporation a sufficient concentration of the peptide monomer in lipid bilayers. The driving force for the self-assembly of the channel structure is primarily provided by the enthalpic contribution of a large number of hydrogen bonding interactions which are favored in the low dielectric constant medium of lipid bilayers and by the increase in the lipid chain entropy arising from side chain-lipid interactions. (See D. M Engelman et al. in *Cell* (1981), vol. 23, pages 411-422; L. C. Allen in *Proc. Natl. Acad. Sci. USA* (1975), vol. 72, pages 4701-4705; and D. M. Engelman in *Annu. Rev. Biophys. Chem.* (1986), vol. 15, pages 321-353). In short, it is demonstrated that the designed flat ring-shaped cyclic peptide is not only structurally predisposed toward intermolecular interaction, but is also energetically favored to self-assemble, in the lipid bilayer environment to furnish the desired transmembrane channel structure. The following studies using a variety of spectroscopic techniques, lipid vesicle model systems, and single ion channel recordings support the validity of the above design hypothesis.

Figure 24A:
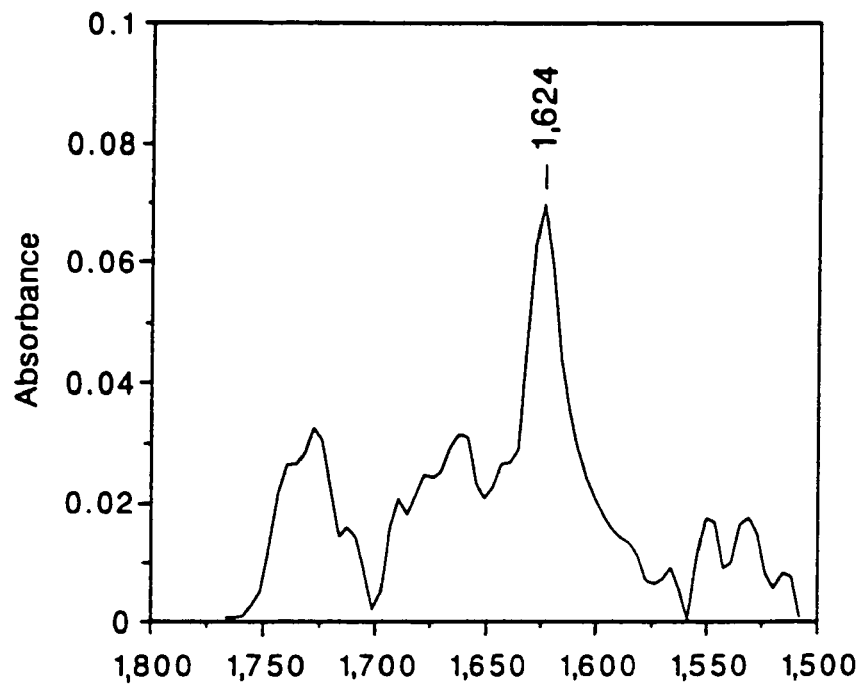
FIGS. 24A and B illustrate infrared spectra of a membrane channel structure formed by cyclo[-(Trp-D-Leu)$_3$-Gln-D-Leu-] (Sequence No.: 9). Figure A illustrates an infrared spectrum at 8-$cm^{-1}$ resolution of the amide-I region of the membrane channel structure. Figure B illustrates an infrared spectrum at 8-$cm^{-1}$ resolution of the N—H stretch region of the membrane channel structure. IR samples were prepared by the addition of a DMSO solution of the peptide to purified liposomes (20 to 50 phospholipids per peptide subunit) followed by gel filtration on a Sephadex G-25 column (for the method used to prepare the liposomes see legend to FIG. 3). Liposomes were then applied to a $CaF_2$ disk and dried in vacuo for 30 minutes. Characteristic absorbances due to the peptide channel ensemble are indicated in the figure.
Figure 24B:
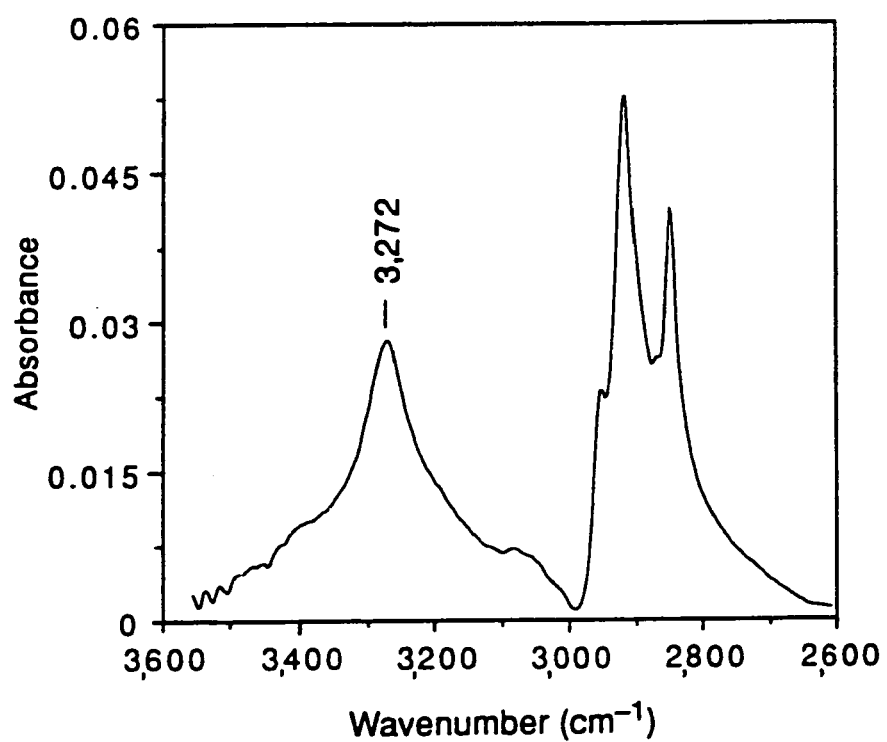

Addition of the peptide subunit to aqueous liposomal suspensions effects a rapid partitioning of the subunit into the lipid bilayers and its spontaneous self-assembly into ion transport-competent membrane channel structures. Incorporation of the peptide subunit into lipid bilayers using large unilamellar vesicles has been established by absorption and fluorescence spectroscopy. Formation of the hydrogen-bonded transmembrane channel structure in phosphatidylcholin liposomes has been supported by FT-IR spectroscopy (FIG. 24). The observed amide-I band at 1624 $cm^{-1}$ is not only similar to the carbonyl stretching frequencies found in other nanotube structures disclosed herein, but is also consistent with the infrared spectrum of gramicidin A in similar lipid bilayers. (E. Nabedryk et al in *Biophys. J.* (1982), vol. 38, pages 243-249. Furthermore, the observed N—H stretching frequency at 3272 $cm^{-1}$ strongly supports the formation of a tight network of hydrogen bonds with an average intersubunit distance of 4.7 Å.

Figure 25:
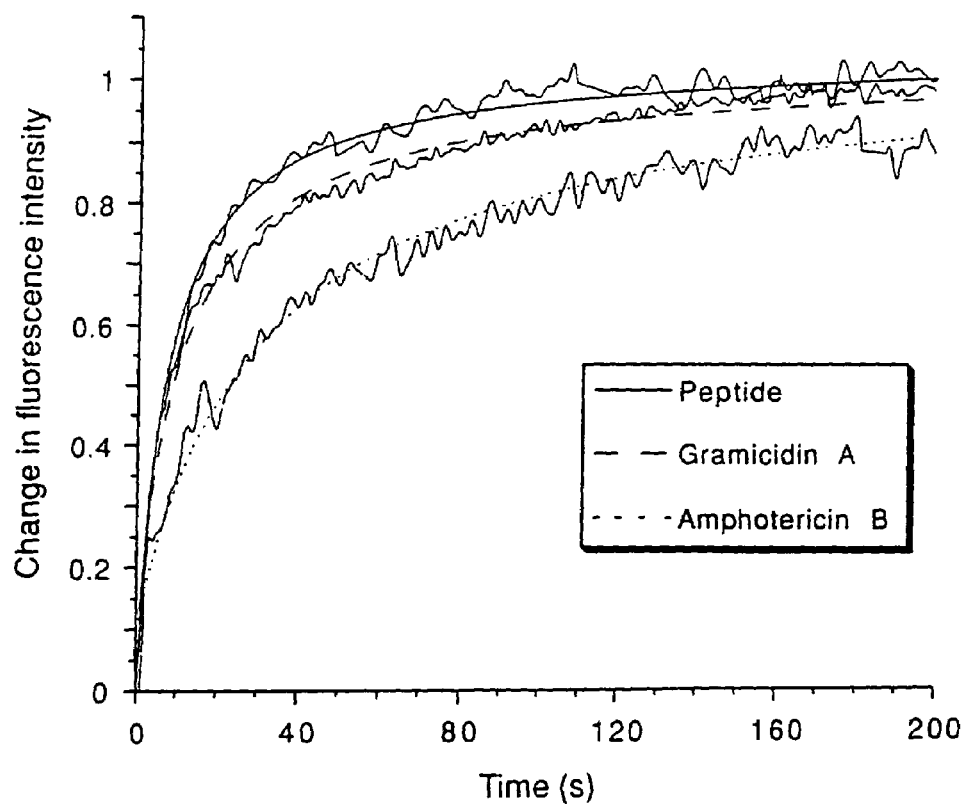
FIG. 25 illustrates the ensuing proton efflux upon the addition of the channel forming compounds indicated in FIG. 24. The proton efflux is expressed in terms of the fractional change in the fluorescence intensity of vesicle entrapped 5(6)-carboxyfluorescein as a function of time (sampling time was at 0.3 seconds interval). Equal molar amounts of channel forming compounds were used in each experiment to allow direct comparisons of channel-mediated proton transport activity. The amount of added channel forming compounds in each experiment ranged from of 2 to 20 nmoles corresponding to approximately 150 channels per liposome for the lowest concentrations to 1100 channels per liposome for the highest amount of added compounds.

Formation of transmembrane channels was also inferred from its highly efficient proton transport activity. Vesicles were prepared having pH 6.5 inside and pH 5.5 in the outside bulk solution. The collapse of the imposed pH gradient in these vesicles, upon formation of the putative transmembrane channel structure, was studied by monitoring the fluorescence intensity of an entrapped pH-sensitive dye. (V. E. Carmichael et al, in *J. Am. Chem. Soc.* (1989), vol. 111, pages 767-769). As shown in FIG. 25, addition of the peptide to such vesicles suspensions causes a rapid collapse of the pH gradient. Unilamellar vesicles were prepared by the reverse-phase evaporation using DPPC, OPPC, cholestrol in the ratio of 1:1:2 in a solution containing 5(6)-carboxyfluorescein (20 mm in phosphate/saline buffer: 137 mM NaCl, 2.6 mM KCl, 6.4 mM $Na_2HPO_4$, 1.4 mM $KH_2PO_4$, pH 6.5) according to the method of F. Szoka et al. in *Proc. Natl. Acad. Sci. USA* (1978), vol. 75, pages 4194-4198. Liposomes were then sized by multiple extrusions through Nucleopore® polycarbonate membranes (10 times, 50 psi, using 0.8 and 2×0.4 micron filter stacks) and the untrapped 5(6)-carboxyfluorescein was removed by size exclusion chromatography (Sephadex G-25 column 1×30 cm) using the same phosphate/saline buffer according to the method of F. Olson et al. in *Biochim. Biophys. Acta* (1979), vol. 557, pages 9-23. Vesicles formed in this way are approximately 150 nanometer in diameter as determined by electron microscopy. (R.R.C. New, Ed. *Liposomes*, Oxford university Press, 1990). In each experiment, 70 ml of the stock vesicle solution ($3.5 \times 10^{-3}$ M in phospholipids) was added to pH 5.5 buffer (1.3 ml, 137 mM NaCl, 2.6 mM KCl, 6.4 Na$_2$HPO$_4$, 1.4 KH$_2$PO$_4$) and placed in a 1 cm quartz cuvett inside a stirring thermojacketed sample holder of the florescence instrument and equilibrated at 25° C. for 15 minutes with gentle stirring. To the cuvett, through an injector port, 25 ml of the channel forming compounds in DMSO was added with continuous fluorescence monitoring at 520 nm (excitation at 470 nm). The observed data were then normalized for comparison into the fractional change in fluorescence (($I_0$-$I_t$)/($I_0$-$I_\infty$)) (V. E. Carmichael et al, in *J.Am. Chem. Soc.* (1989), vol. 111, pages 767-769)). According to these experiments, the apparent ion transport activity of cyclo[-(Trp-D-Leu)$_3$-Gln-D-Leu-] is similar to, if not higher than, that of gramicidin A and amphotericin B (FIG. 25). The lipid bilayers used were formed on the tip of patch pipettes using a mixture of synthetic POPE: POPS (4:1) (1-palmitoyl-2-oleoyl-Sn-glycero-3-phosphatidylethano lamine and -serine). Five to 10 ml of the peptide solution (1.0×10$^{-7}$ or 2.0×10$^{-6}$ M in 25% DMSO in buffer solution containing 500 mM NaCl or KCl, 5 mM CaCl$_2$, 10 mM HEPES, pH 7.5) was added to 150 ml subphase volume resulting in spontaneous partitioning of the peptide into the membrane. Ion channels formed spontaneously after peptide was added to the subphase of lipid bilayers. Ion channel activity was observed in 14 out of 22 membranes under symmetrical solutions of 500 mM NaCl or KCl, 5 mM CaCl$_2$, 10 mM HEPES, pH 7.5. Data acquisition and analysis were performed on a Gateway 2000/486 computer using pClamp software package and TL-1 labmaster interface. Acquisition rate was 0.1 ms and data were filtered at 2 kHz.

Control studies, monitoring the release of 5(6) carboxyfluorescein dye, indicated that the collapse of the pH gradient was not due to the rupturing of the liposomes nor due to the small amounts of organic solvents (<2% DMSO) employed in these studies. Furthermore, the control peptide cyclo[-(Gln-D-Leu)$_4$] which lacks the appropriate surface characteristics for partitioning into the lipid bilayers, but otherwise quite similar in design to the channel forming peptide described above, does not display any ion transport activity under similar conditions. The second control peptide cyclo[-($^{Me}$N-D-Ala-Phe)$_4$-] which has the desirable hydrophobic surface characteristics but lacks the propensity for participating in extended hydrogen bonding network, was also designed and tested for ion transport activity. The peptide design incorporates a novel N-methylation strategy on one face of the ring structure which predisposes the subunit toward a dimeric cylindrical structure (Ghadiri, M. R., Kobayashi, K., Granja, J. R., Chadha, R., and McRee, D. E. manuscript in preparation). Such a dimeric cylindrical ensemble is approximately 10 Å thick and can not span the lipid bilayer. Although the peptide has been shown to partition effectively into lipid bilayers, it does not promote proton transport activity in the above vesicle experiments. Together, these experiments suggest that not only the hydrophobic surface characteristic of the channel forming peptide is an important factor, but also the peptide subunit must be able to participate in extended hydrogen-bonded stacking interactions to produce channel structures long enough to span the lipid bilayer.

The designed transmembrane ensemble also shares important characteristics with natural ion channel formers such as gramicidin A and amphotericin B. First, the peptide shows concentration dependence effects on the rate of channel formation (data not shown). Second, when low concentrations of the channel forming peptide is used in the above proton transport experiments, only part of the vesicle population goes to equilibrium very fast. This phenomenon reflects the statistical distribution of the channel forming species among the vesicle population—only part of the population has enough channel-forming molecules to form permeable competent structures in an all-or-none type of a process. Unlike "ion carriers" such as monensin and valinomycin which bind to metal ions and partition between aqueous-phase and the lipid-phase in order to establish ion equilibrium across the membrane, channel forming species at low concentrations (the designed peptide here, amphotericin B, gramicidin A, and others) because of their inability to defuse back out of the membrane, can not penetrate other vesicles and unlike ionophores can not easily establish proton or ion equilibrium in all vesicles present in solution. Therefore, the observed rapid proton efflux in the above types of experiments simply reflects the rate limiting step of peptide diffusion into the lipid bilayer and self-assembly into ion-transport competent channel structures and does not reflect the actual rate of channel-mediated ion transport which can occur on a much faster time scale (Vide infra).

Figure 26:
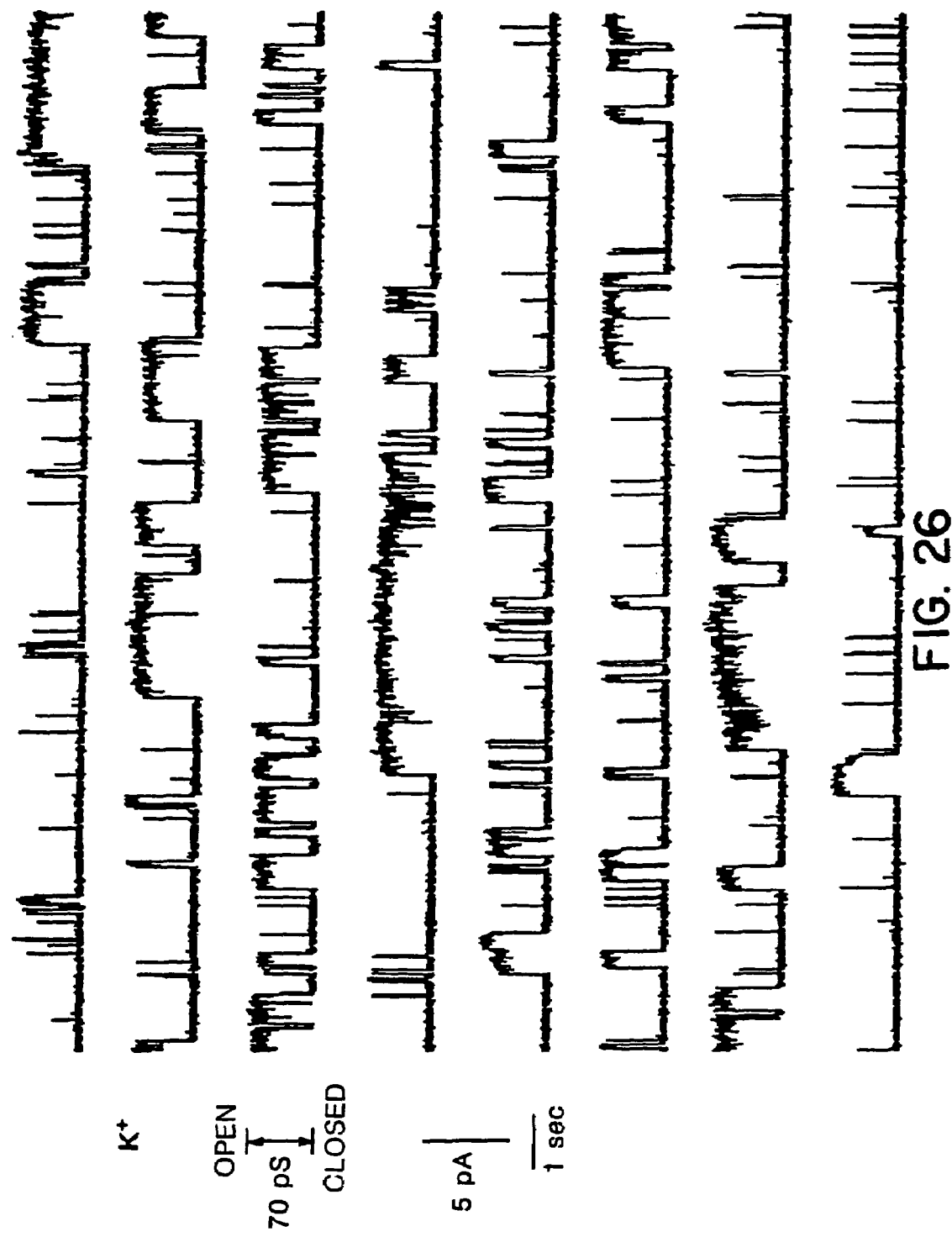
FIG. 26 illustrates a 140 second continuous $K^+$ single channel conductance recording at 50 mV of the channel forming compounds indicated in FIG. 24. Open-closed transitions indicate gating mechanisms which may reflect structural flexibility or rapid assembly-disassembly of the tubular membrane channel structures. Short and long channel life times in the open state could be distinguished with values of $t_{(short)}$=0.7±0.03 ms and $t_{(long)}$=37.14±8.99 ms (total number of events 510) with an overall open probability P(O) of 0.29. Peptide concentration at the subphase was $1.0 \times 10^{-7}$ M. As is expected for any such self-assembling channel forming species, channel opening lifetimes show significant dependence on the peptide concentration. Raising the added peptide concentration in the subphase to $2.0 \times 10^{-5}$ M, produces open channel lifetimes of >30 open channel lifetimes of >30 seconds.

The ultimate test in establishing and quantitating the transport efficiency of a membrane channel structure is to measure its single channel conductance using micro patch clamp techniques. (B. A. Suarez-Isla et al., *Biochemistry* (1983), vol. 22, pages 2319-2323.) Observing a high throughput rate of ions demonstrates ion channel formation and is a diagnostic feature distinguishing ionic channel mechanisms from those of other ion transport devices such as ion carriers. (P. Leuger, *Angew. Chem.* (1985), vol 97, page 939); and *Angew. Chem. Int. Ed. Engl.* (1985), vol. 24, pages 905-923.) Single channel conductances, using planar lipid bilayers with peptide concentrations in the range of 10$^{-7}$ M in the subphase, are approximately 55 pS (pico Siemens) in 500 mM NaCl and 65 pS in 500 mM KCl (FIG. 26). Higher conductance found in KCl as compared to NaCl is consistent with the expected weak ion selectivity of the 7.5 Å pore structures and reflects the relative mobility of Na$^+$ vs. K$^+$ ions in solution. Therefore, a 55 pS channel in NaCl and a 65 pS channel in KCl are likely to arise from the same structural entity (same number of stacked rings). In addition, single channel conductance was shown to be independent of the applied voltage in the measured range of 10-100 mV. The actual rate of channel-mediated ion transport is therefore a prodigious 2.2×10$^7$ ion.sec$^{-1}$ for K$^+$ and 1.8×10$^7$ ion.sec$^{-1}$ for Na$^+$ which is almost three times faster than that of gramicidin A under similar conditions. (E. Bamberg et al. in *Biochim. Biophys. Acta* (1974), vol. 367, pages 127-133.

The strategy described here also allows for the design of transmembrane channel structures with larger pore diameters for use in "molecular" transport across lipid bilayers and as such it should provide a potential vehicle for drug delivery into living cells and may find use in antisense and gene therapy applications.

Figure 27A:
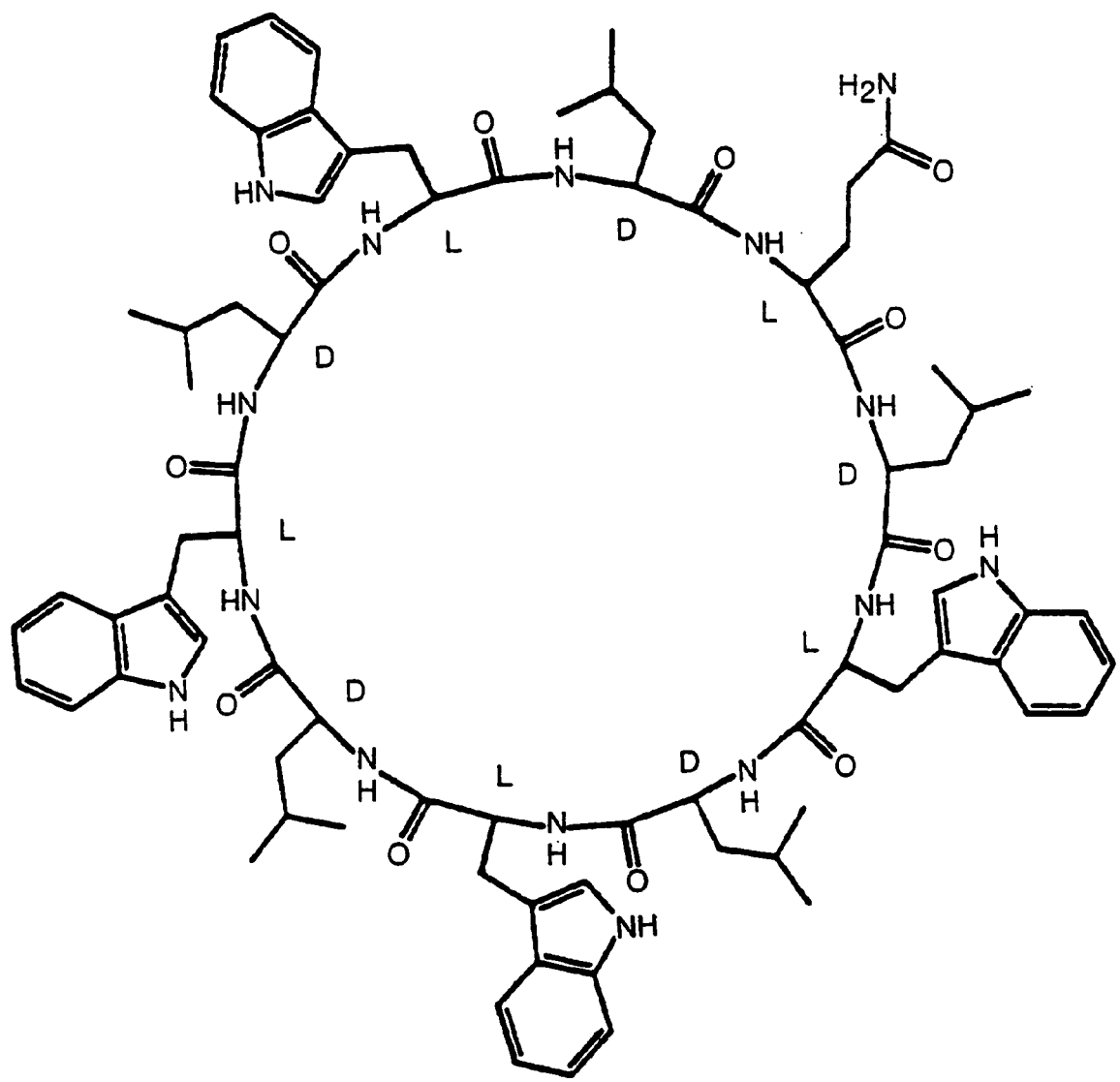
FIG. 27A, the chemical structure of the peptide subunit, i.e., cyclo[-Gln-(D-Leu-Trp)$_4$-D-Leu-] (Sequence No.: 9), is shown on the top (D- or L- refers to the amino acid chirality).
Figure 27B:
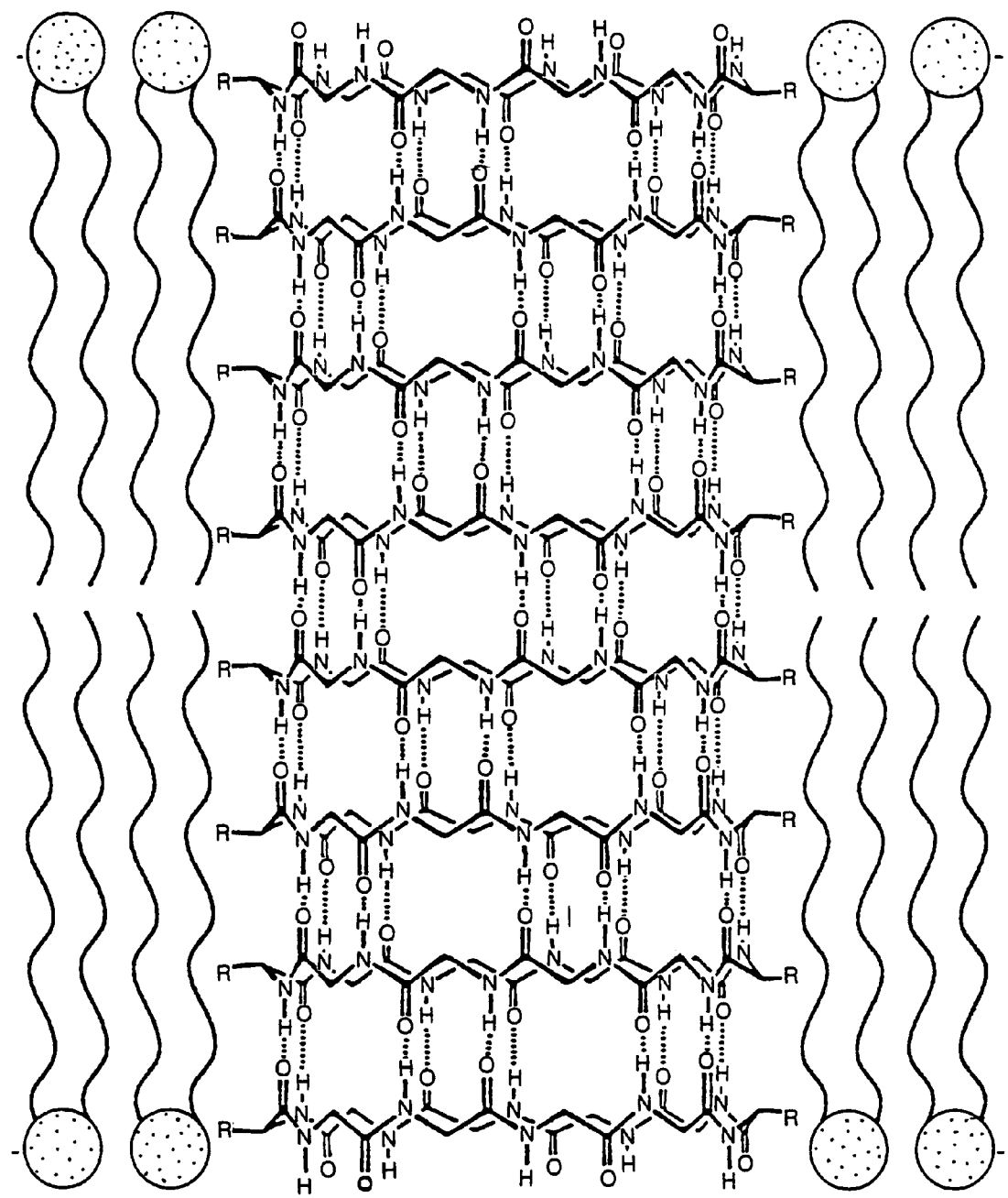
FIG. 27B illustrates a schematic representation of the self-assembled tubular transmembrane channel structure embedded in a lipid bilayer membrane emphasizing the antiparallel ring stacking, the presence of extensive inter-subunit hydrogen-bonding interactions, and side chain-lipid interactions (for clarity most side chains are omitted).

Channel-Mediated Transport of Glucose Across Lipid Bilayers:

The design, synthesis, and characterization of an artificial transmembrane pore structure capable of mediating transport of glucose accross lipid bilayers is disclosed. The design strategy is based on the propensity of a novel 10-residue cyclic peptide subunit cyclo[-Gln-(D-Leu-Trp)$_4$-D-Leu-] (Sequence No. 10) toward spontaneous self-assembly in lipid bilayers to form 10 Å van der Waals aqueous pore structures. Molecular modeling indicated that for the passage of glucose through the cylindrical cavity of the tubular transmembrane structure, the internal van der Waals pore diameter of greater than 9 Å is required. Therefore for the task in hand, a ten-residue peptide subunit is employed which upon self-assembly can produce tubular ensembles having a uniform 10 Å internal diameter (FIGS. 27A-B).

The ten-residue peptide subunit employed in the present study, cyclo[-Gln-(D-Leu-Trp)$_4$-D-Leu-], is made up of largely tryptophan and leucine residues to favor its partitioning into and self-assembly in lipid bilayers. It was synthesized on solid support[5] and characterized by $^1$H NMR spectroscopy and mass spectrometry. Addition of the peptide subunit to aqueous suspensions of large unilamellar liposomes effects a rapid incorporation of the peptide into the lipid bilayer. This has been supported by absorption and fluorescence spectrophotometry and gel permeation studies. Formation of a hydrogen bonded transmembrane channel structure in phosphatidylcholin liposomes has been established by FT-IR spectroscopy[6]. The observed amide-I band at 1,625 cm$^{-1}$ and the N—H stretching band at 3,272 cm$^{-1}$ are similar to those of the previously characterized peptide nanotubes[2a,4] and strongly support the formation of a tight network of b-sheet-like hydrogen bonded structures with an average intersubunit distance of 4.8 Å. Formation of transmembrane channels was also inferred from its remarkably high ion transport efficiencies (>10$^7$ ions.sec$^{-1}$) as indicated by single ion channel recordings using micro patch clamp techniques.

Figure 28:
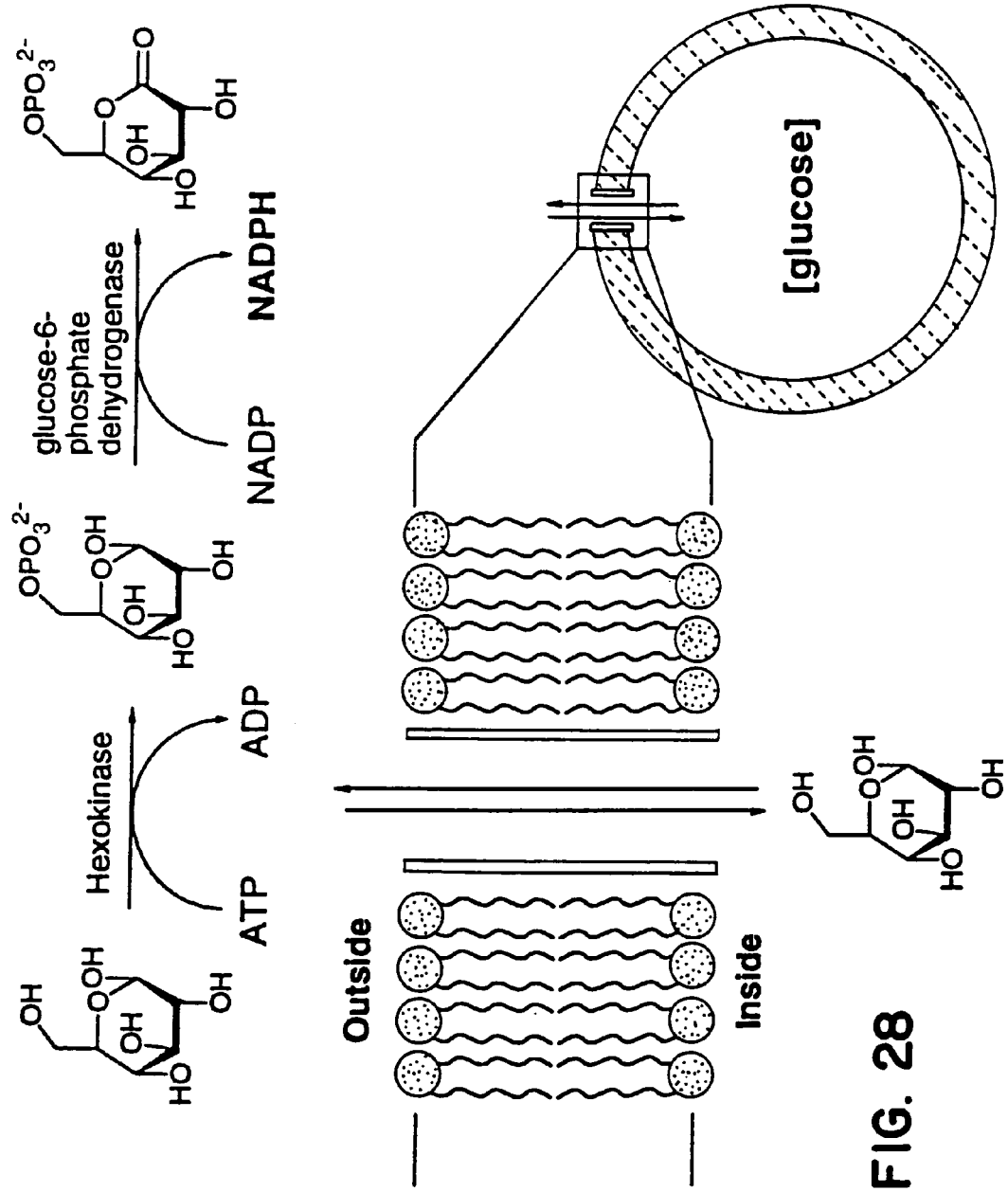
FIG. 28 illustrates a schematic illustration of channel-mediated glucose transport and the enzyme coupled assay used to monitor the transport activity with respect to the channel structure indicated in FIGS. 27A-B. Formation of a transmembrane pore structure(s) initiates glucose efflux from the liposome which can be directly monitored by measuring the rate of NADPH production. The enzymes and cofactors employed are hydrophilic and thus can not pass through the lipid membrane and are too large to penetrate the channel structure. Therefore, only the released glucose can undergo the enzymatic reaction.
Figure 29:
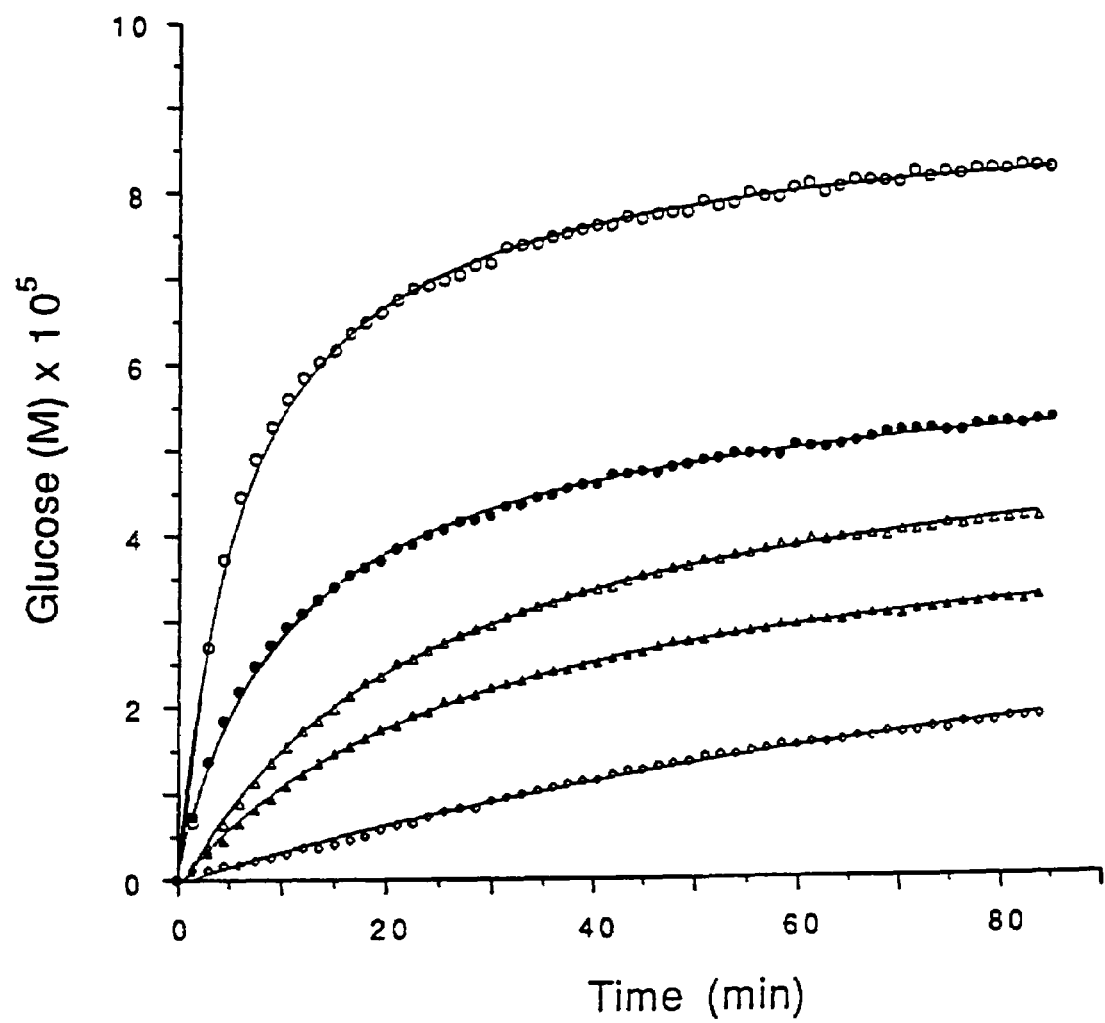
FIG. 29 illustrates the ensuing glucose efflux on the addition of various amounts of the channel forming peptide of FIGS. 27A-B, viz., open circles represent $15.0 \times 10^{-6}$ M; closed circles represent $11.0 \times 10^{-6}$ M; open triangles represent $7.5 \times 10^{-6}$ M; closed triangles represent $5.6 \times 10^{-6}$ M; and open diamonds represent $3.8 \times 10^{-6}$ M. Efflux is expressed in terms of the amount of glucose released as a function of time (sampled at 90 sec intervals). The large unilamellar vesicles used in this study contained 200 mM D-glucose. All curves are background corrected to remove any contribution from the nonspecific glucose leakage from the liposomes.

Glucose transport activity was studied in isotonic solutions using glucose entrapped unilamellar lipid vesicles. Unilamellar vesicles, ~150 nm in diameter, were prepared by the reverse-phase evaporation method using 1,2-dipalmitoyl-Sn-glycero-3-phosphatidylcholine (DPPC), 1-palmitoyl-2-oleoyl-Sn-glycero-3-phosphatidylcholine (POPC), 1-palmitoyl-2-oleoyl-Sn-glycero-3-phosphatidylserine (POPS), and cholesterol in the ratio 1:1:0.1:1 in a solution containing 50, 100, 150, or 200 mM D-glucose, 100 mM NaCl, and 50 mM Tris buffer pH 7.5, according to the method of F. Szoka et al. in *Proc. Natl. Acad. Sci. USA* (1978), vol. 75, pages 4194-4198. Liposomes were gel-filtered using Sephadex G-25 in an isotonic buffer containing 50, 100, 150, or 200 mM sucrose, 100 mM Nacl, and 50 mM Tris buffer pH 7.5. The liposome preparation was stored at 4° C. and used within 24 hours of the synthesis. The transport phenomenon was monitored spectrophotometrically at 340 nm for the production of NADPH using an enzyme coupled assay (FIG. 28), according to the method of S. C. Kinsky in *Methods in Enzymology*; Fleischer, S., Packer, L., Eds; Academic Press: London, 1974; vol. 32, pp 501-513. All experiments were performed on a Spectronic-3000 photodiode-array spectrophotometer using 3 ml quartz cuvettes placed in the thermojacketed multiple cell holder and held at 27° C. In a typical experiment the following solutions were sequentially placed in the cuvettes: 750 ml of buffer (300 mM NaCl, 50 mM Tris pH 7.5, 3.5 mM MgCl$_2$, and 0.15 mM CaCl$_2$), 500 ml of the enzyme solution (8 units.ml$^{-1}$ of hexokinase, 16 units.ml$^{-1}$ of glucose-6-phosphate dehydrogenase, 2.5 mM ATP, 1.3 mM NADP all dissolved in 200 mM NaCl, 50 mM Tris pH 7.5, 3.5 mM MgCl$_2$, and 0.15 mM CaCl$_2$), and 75 ml of the stock liposome solution[8] (2.6×10$^{-3}$ M in phospholipids). Total glucose content in each cuvette was determined by Triton X-100 treatment. Transport was initiated by the addition of an appropriate amount (5, 7.5, 10, 15, or 20 ml) of the peptide solution (1 mM in DMF) to the reference and the sample cuvettes (hexokinase was omitted from the reference sample). For measuring the background (nonspecific glucose leakage from the liposomes) the sample was prepared in an identical fashion except appropriate amounts of DMF were added in place of the channel forming peptide. The production of NADPH was monitored at 340 nm for 1.5 h at 90 second time intervals. Because of the high catalytic efficiencies of the enzymes employed, the rate of NADPH production is directly proportional to the rate at which glucose is released from the liposomes. The transport of glucose initiated by the addition of various amounts of the channel forming peptide to the glucose-entrapped liposomes follows a first order rate profile with an apparent rate constants of 1.2±0.09, 0.74±0.1, 0.48±0.05, and 0.18±0.02 mol(glucose)/mol(peptide)/min for liposomes having initial glucose concentrations of 200, 150, 100, and 50 mM, respectively (FIG. 29). The apparent rate of glucose transport is, in all likelihood, a gross underestimation of the actual rate of channel mediated transport because only a minute fraction of the total number of peptides incorporated in the lipid bilayer are assembled, at a given time, in the form of active transmembrane channel structures. Unlike carrier-mediated transport which must display Michael is-Menten saturation kinetics, the observed linear relation between transport rate and glucose concentration strongly supports a simple transmembrane channel-mediated diffusion process. (W. D. Stein in *Channels, Carriers, and Pumps*, Academic Press: San Diego, 1990.) Control studies, monitoring the release of entrapped 5(6)-carboxyfluorescein under similar conditions, established that the transport of glucose was due to neither the rupturing of the liposomes nor the small amounts of DMF (<2%) employed in these studies. (See: N Jayasuriya et al., in *J. Am. Chem. Soc.* (1990), vol. 112, pages 5844-5850; and J. N. Weinstein et al., in *Science* (1977), vol. 195, pages 489-492.) Furthermore, neither gramicidin A, a well-known naturally occurring ion channel forming peptide with an internal diameter of approximately 4.5 Å, nor the very similar ion channel forming peptide cyclo[-Gln-(D-Leu-Trp)$_3$-D-Leu-],disclosed herein to form channels with approximately 7.5 Å internal diameter, display any glucose transport activity under similar assay conditions. Together, this demonstrates size-selective pore-mediated transport of glucose.

Figure 4:
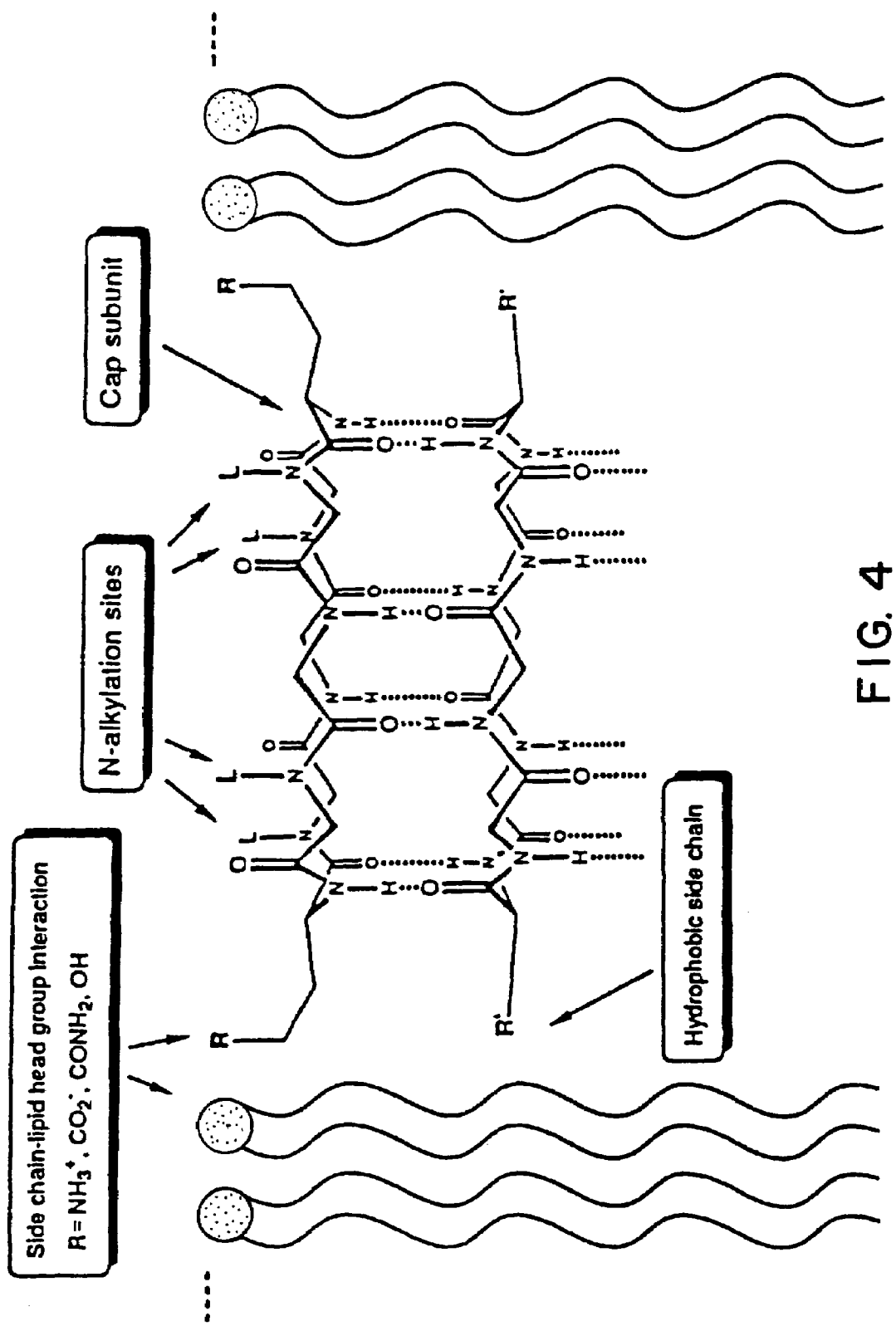
FIG. 4 illustrates a side view of a cap subunit, such as cyclic peptide 7 and its interactions with an adjacent cyclic peptide subunit and the surrounding media.

Carped Nanotubes:

Another such feature has to do with channel capping—the process by which the self-assembled molecular tube is terminated. It is evident from FIG. 4 that the subunits at the channel openings, i.e., at the "cap" positions, are unique with respect to their mode of interaction with the other subunits as well as the micro-environment in which they reside. The peptide subunits at the cap position participate in backbone-backbone hydrogen bonding with only one other subunit and on only one side of the backbone structure. The cap subunits also reside in the amphiphilic micro-environment of the lipid-water interface.

The key structural requirement for producing a multiple ring-stacked tubular structure is the spatial disposition of the backbone hydrogen bond donor and acceptor sites on both faces of the peptide ring structure. However, if the cyclic peptide subunit is devoid of hydrogen bond donation from one face of the ring structure through the blocking, e.g., alkylation of backbone amide nitrogen functionalities of one of the chiral moieties present, such a cyclic peptide subunit cannot participate in an extended hydrogen bonding network, but serves to cap a tubular structure.

Such selectively alkylated cyclic peptides in non-polar solution are predisposed to dimerization. However, the addition of such selectively alkylated cyclic peptide subunits to the aforementioned ring-stacked tubular structure in an appropriate solvent permits capping or termination of the ring-stacked tubular structures by the monomeric, selectively alkylated cyclic peptides.

Figure 15:
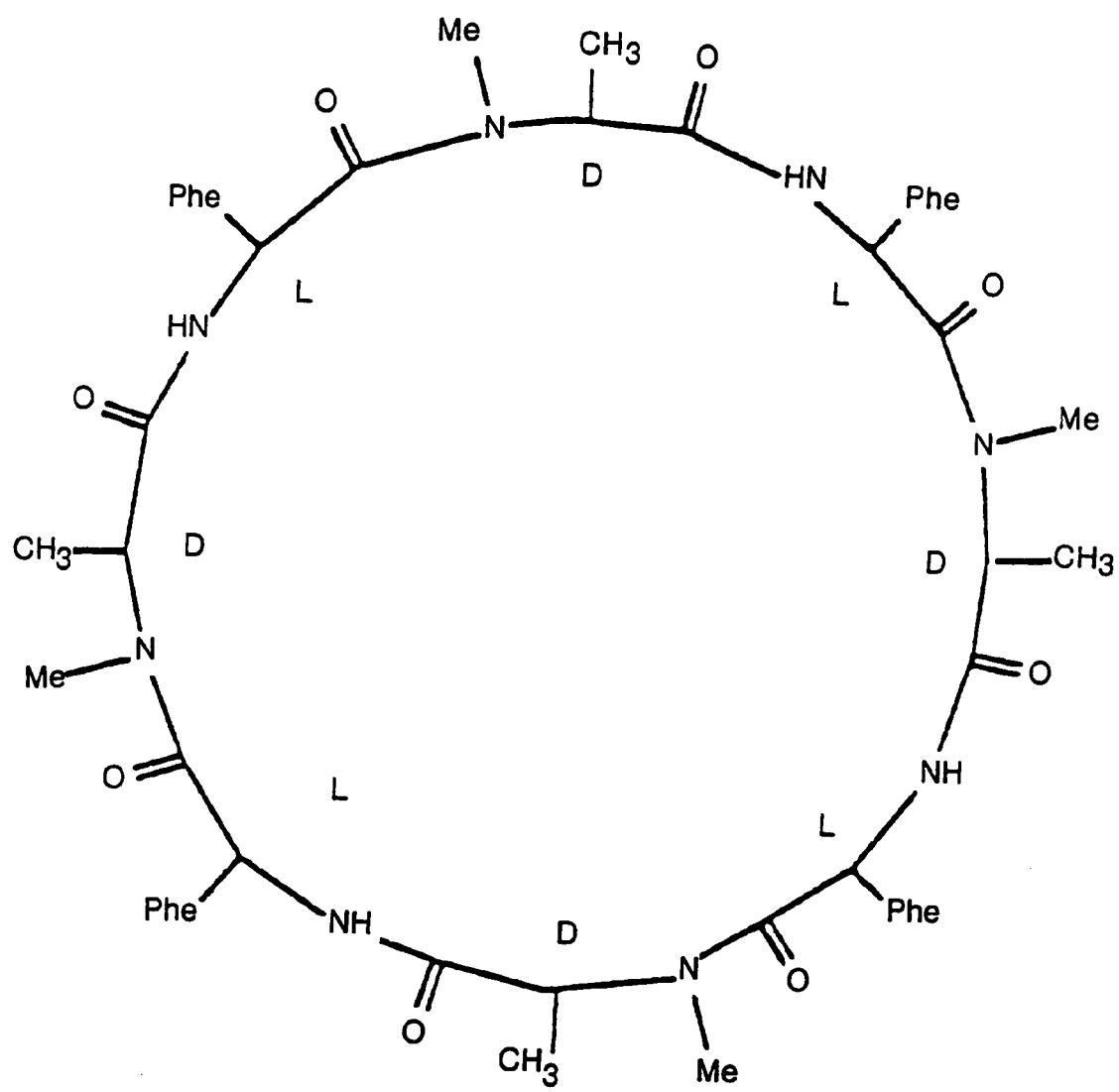
FIG. 15 illustrates the structure of cyclic peptide 7, i.e., an eight amino acid cyclic peptide having the amino acid sequence cyclo[-(Phe-N(Me)Ala$_4$-]. (Sequence No.: 7) Cyclic peptide 7 is a terminal cyclic peptide, i.e., it is capable of hydrogen bonding only on one side of the disk and therefore terminates the assembly of the molecular tube.
Figure 16A:
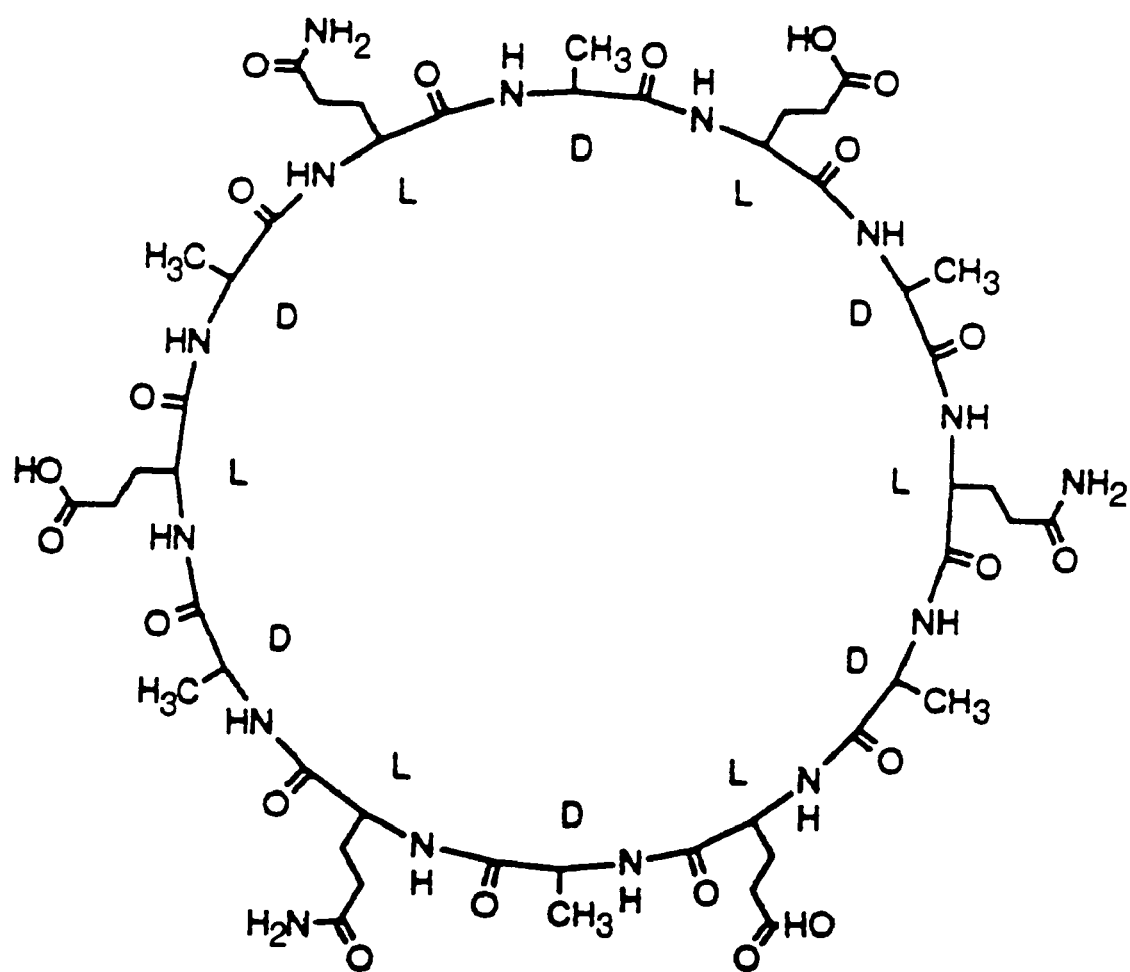
FIG. 16A illustrates the structure of cyclic peptide 8, i.e., a twelve amino acid cyclic peptide having the amino acid sequence cyclo[-(Gln-D-Ala-Glu-D-Ala)$_3$-]. (Sequence No.: 8)
Figure 16B:
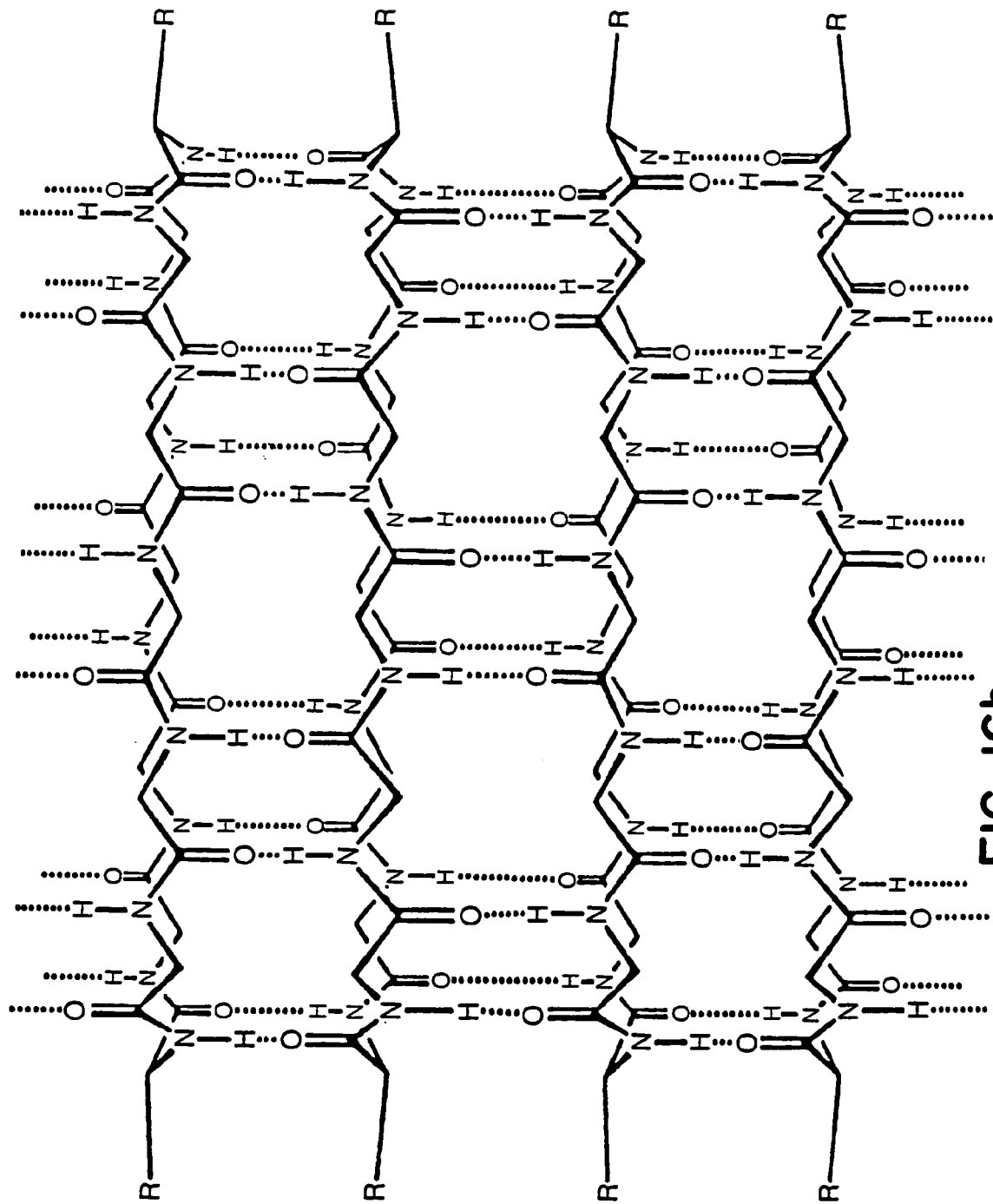
FIG. 16B illustrates a fragment of a molecular tube having four cyclic peptides of type 8.
Figure 17:
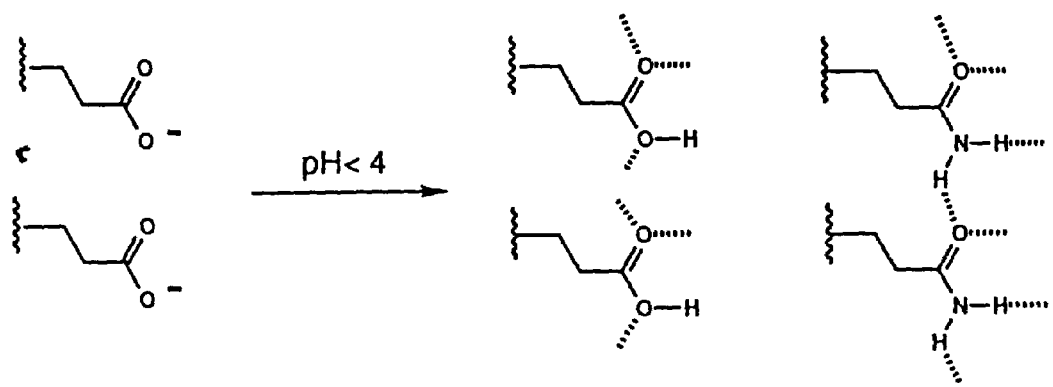
FIG. 17 illustrates the hydrogen bonding of molecular tubes constructed with cyclic peptide 1. At high pH, unfavorable electrostatic interactions and high water solubility disfavors intermolecular interactions. At low pH, specific intermolecular backbone-backbone and side chain-side chain hydrogen bonding interactions as well as the lower water solubility of the peptide monomers promotes the formation of molecular tube ensembles.

One such preferred cyclic peptide is the eight-residue cyclic peptide cyclo[-(L-Phe-D-$^{Me}$NAla)$_4$-] shown in FIG. 15. The most meaningful way of classifying the various amino acids is on the basis of the polarity of their R groups in water near pH 7. There are four main classes: (1) nonpolar or hydrophobic, (2) polar but uncharged, (3) positively charged, (4) negatively charged. The nonpolar or hydrophobic group includes amino acids with aliphatic R-groups, such as alanine, leucine, isoleucine, valine, and proline, amino acids with aromatic ring R-groups, such as phenylalanine and tryptophan, and one amino acid with a sulfur-containing R-group, methionine.

Molecular modeling indicated that methylation of backbone amide nitrogen functionalities at all alanine residues would be sufficient to effectively prevent one face of the putative peptide ring structure from participating in intermolecular hydrogen bonding and ring stacking interactions. The peptide was also designed to have an allowed symmetry for favorable intermolecular packing interactions in the solid-state thus permitting its detailed structural characterization by X-ray crystallographic techniques Amino acids having hydrophobic R-groups were chosen for this Example so as to make the subunit and the resulting dimer ensemble soluble in nonpolar organic solvents. However, the choice of the R group to any given instance depends on the desired solubility characteristics of the end product.

The linear form of the target sequence H$_2$N-(L-Phe-D-$^{Me}$NAla)$_4$—CO$_2$H was synthesized according to standard solid-phase methods described hereinabove and then cyclized in solution to furnish the desired cyclic peptide subunit using the following procedure. A solution of the linear peptide in DMF (1 mM) was treated with TBTU (2-(1H-Benzotriazol-1-yl)-1,1,3,3-tetramethyluronium tetrafluoroborate, 3 mM), HOBt (1-Hydroxybenzotriazole, 3 mM) and DIEA (diisopropylethylamine, 1% v/v) at 5° C. for 12 h to give the desired cyclic peptide monomer, after reverse-phase HPLC purification, in 70% yield, which can then be used for capping or terminating peptide nanotubes.

The $^1$HNMR spectrum of the produced peptide subunit in polar solvents, such as deuterated methanol or dimethyl sulfoxide (DMSO), displays multiple slow-exchanging conformational isomers due to the well-known propensity of secondary amides toward cis-trans isomerization. Variable temperature NMR experiments in DMSO indicate cis-trans conformational activation barriers on the order of 16 to 17 kcal.mol$^{-1}$. However, in nonpolar solvents such as carbon tetrachloride (CCl$_4$) or deuterochloroform (CDCl$_3$) the peptide exists in an all trans flat-ring-shaped backbone conformation which is in dynamic equilibrium with the expected dimeric cylindrical ensemble. The monomeric peptide subunit displays a temperature independent (from −40 to 55° C. in CDCl$_3$) and highly symmetrical $^1$H NMR spectrum excluding the possibility of an intramolecularly hydrogen bonded conformation The preponderance of a flat ring-shaped backbone conformation is also indicated by the observed 7.5 Hz J$_{NH—CaH}$ coupling constant. Intermolecular hydrogen bonding interactions producing the stacked dimeric ensemble are signified by the expected downfield shift of the phenylalanine N—H backbone resonance from 6.98 to 8.73 ppm (J$_{NH—CaH}$=8.5 Hz) and are unequivocally established by the observed exchange and NOE cross peaks in its ROESY spectrum.

ROESY experiments were performed on a Bruker AMX-500 with 300 ms spin lock (mixing) time using Bruker's standard pulse program. Data were processed using FELIX software. Time domain data was apodized using skewed sine-bell squared window functions. Zero-filling was used to obtain the final data size of 1024×1024 complex matrix. A. Bax, D. G. Davis, *J. Magnetic Resonance* 1985, 63, 207-213.

Formation of a tight hydrogen bonded ensemble with an average intersubunit N—O distance of 2.95 Å is also evidenced by the appearance of an N—H stretching band in the infrared spectrum at 3309 cm$^{-1}$. As expected, the self-assembly process displays concentration and solvent dependent spectra with the association constants K$^a$(CCl$_4$)=1.4× 10$^4$M$^{-1}$ and K$_a$(CDCl$_3$)=1.26±0.13×10$^3$M$^{-1}$ at 293 K.

The association constants reported are the lower limits due to the presence of small amounts of included water in the peptide samples. When water is rigorously excluded (4 Å molecular sieves) the association constant K$_a$(CDCl$_3$)= 1260 M$^{-1}$ is approximately doubled to K$_a$(CDCl$_3$)=2540 M$^{-1}$. The K$_a$(CCl$_4$) reported was performed in a mixture of 84% CCl$_4$ and 16% CDCl$_3$ for solubility reasons.

Variable temperature studies (van't Hoff plots) establish the following thermodynamic parameters for the dimerization process in chloroform: ΔCp=−203.1 cal.K$^{-1}$.mol$^{-1}$, ΔH°$_{298}$=−11.0 kcal.mol$^{-1}$, and ΔS°$_{298}$=−23.7 e.u. which clearly supports the expected enthalpic contribution of intermolecular hydrogen bonding interactions (0.5 to 0.7 kcal.mol$^{-1}$ for each hydrogen bonding interaction) as the major driving force in the self-assembly process.

The above experiments indicate that the peptide subunit adopts a flat ring-shaped solution conformation which is energetically favored toward ring stacking and intermolecular hydrogen bonding interactions by 4.0 to 5.6 kcal.mol$^{-1}$, depending on the solvent employed. It follows then that an additive gain in free energy of stabilization is to be expected as the number of ring-stacking interactions are increased. This is particularly relevant to the self-assembled nanotubes and to the transmembrane ion channel structures that can be produced.

Colorless prismatic crystals suitable for X-ray analysis were obtained from the solutions of the peptide in water-saturated dichloromethane by vapor-phase equilibration with hexane. The crystal structure was solved in the space group I422 with a final R-factor of 8.87%. Data were collected on a Rigaku AFC6R diffractometer equipped with a copper rotating anode (Cu$_{Ka}$) and a highly oriented graphite monochromator. The structure was solved in the space group I422 with a final R-factor of 8.87% and weighted R-factor of 10.35% and the residual electron density of 0.64 eÅ$^{-3}$ for 983 unique reflections with F>4.0 σ(F). The unit cell parameters are a=b=16.78, and c=21.97 Å.

The solid-state structure is a cylindrical dimeric ensemble, analogous to the solution structure deduced from the $^1$H NMR and FT-IR analyses, corroborating very well the previously calculated nanotube structures derived primarily from the analysis of electron diffraction patterns. The dimeric ensemble is a combination of a flat ring-shaped cyclic peptides subunit with backbone amide groups perpendicular to the plane of the ring structure and a crystallographic four-fold rotation axis parallel to the c axis passing through the center of the peptide ring. Two peptide subunits are closely stacked in an antiparallel orientation and are related by a two fold rotation along either a or b axis. The b-sheet-like cylindrical ensemble is stabilized by eight intersubunit hydrogen bonding interactions with an intersubunit N—O distance of 2.90 Å. It is noteworthy that the distance of 2.95 Å inferred from the observed NH stretching band at 3312 cm$^{-1}$ in the FT-IR spectrum is remarkably consistent with the crystallographic measurements. The cylindrical ensemble has an approximate 7.5 Å van der Waals internal diameter and a 450 Å$^3$ volume. The tubular cavity is filled with partially disordered water molecules, establishing the hydrophilic internal characteristics of the peptide nanotube structures. The ensemble packs in the crystal in a body centered fashion to produce a continuously channeled superlattice structure along the c axis. The interior surface characteristics of the channels alternate approximately every 11 Å between the hydrophobic domains, created by the aromatic phenyl moieties, and the hydrophilic interior of the peptide cylindrical ensemble. Water molecules near the hydrophobic domains are considerably more disordered, displaying only a weak residual electron density. The observed water electron density is the time average of water molecules binding at multiple overlapping sites suggesting a facile movement of loosely held water molecules within the cavity. This observation which can be attributed to the lack of a discrete, strong binding site(s), is an important attribute of the produced peptide nanotube structures and is believed to contribute to the remarkable transport efficiencies of the formed transmembrane ion channels.

The foregoing discussion and the accompanying examples are presented as illustrative, and are not to be taken as limiting. Still other variations within the spirit and scope of this invention are possible and will readily present themselves to those skilled in the art.

Gated Nanotubes:

Cyclic peptide tubes can also be employed as ion-gated membrane channel structures. By the appropriate choice of the amino acid side chain moieties one can tune, at will, the surface characteristics of the self-assembled cyclic peptide tubes. For the purpose of constructing membrane channel structures, cyclic peptides are designed to have hydrophobic side chain moieties in order to ensure their insertion and self-assembly within the nonpolar environment of lipid bilayer membranes.

The anatomy of the tubular membrane channel structure is schematically shown in FIG. 2. It consists of approximately eight stacks of anti-parallel peptide subunits which enables the channel structure to span the thickness of the average biological lipid membrane-according to our previous electron diffraction studies on the self-assembled organic nanotubes, an average intersubunit distance of 4.8 to 5.0 Å is expected for such an extensively hydrogen bonded antiparallel β-sheet ensemble. The channel structure can form spontaneously upon the dissolution of a sufficient concentration of the peptide monomer in the lipid bilayer. The driving force for the self-assembly of the channel structure is provided by a) the enthalpic contribution of a large number of highly favorable and oriented hydrogen bonding interactions—each hydrogen bond in the nonpolar environment of the membrane is estimated to worth about 5-6 kcal.mol$^{-1}$ (for a channel composed of eight 8-mer cyclic peptides, the hydrogen bond network consists of 56 highly cooperative intermolecular hydrogen bonds), and b) by the increase in the lipid bilayer entropy arising from the side chain-lipid interactions. These highly favorable energetic contributions easily compensate for the loss of entropy associated with the peptide self-assembly and self-organization. Furthermore, considering that only hydrophobic residues are utilized in the peptide design, the unfavorable backbone dissolvation energy does not play a significant role in the assembly process especially since the hydrophilic interior of the channel structure is expected to be filled with a large number of interacting water molecules. In short, such de novo designed cyclic peptides are not only structurally predisposed toward intermolecular interaction, but are also energetically favored to self-assemble, in the lipid bilayer environment, into artificial membrane channels. Furthermore, if needed, simple methods are available for linking the subunits together through side chain-side chain covalent bond formation in order to obtain a permanently fused molecular channel structure.

Figure 3A:
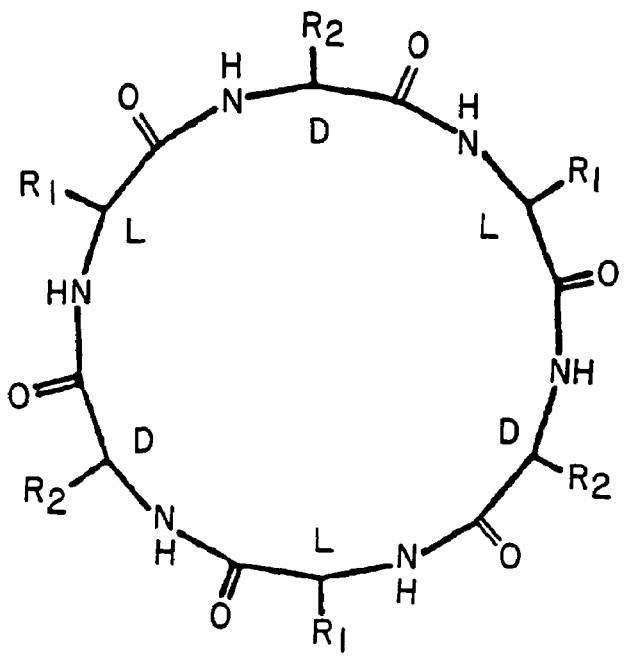
FIGS. 3A-C compare the channel size of three different cyclic peptides employable for constructing transmembrane molecular tubes. D and L denote the chirality of the amino acid residues. $R_1$ and $R_2$ are side chains of hydrophobic amino acid residues such as Val, Leu, Ile, Phe, and Trp.
Figure 3B:
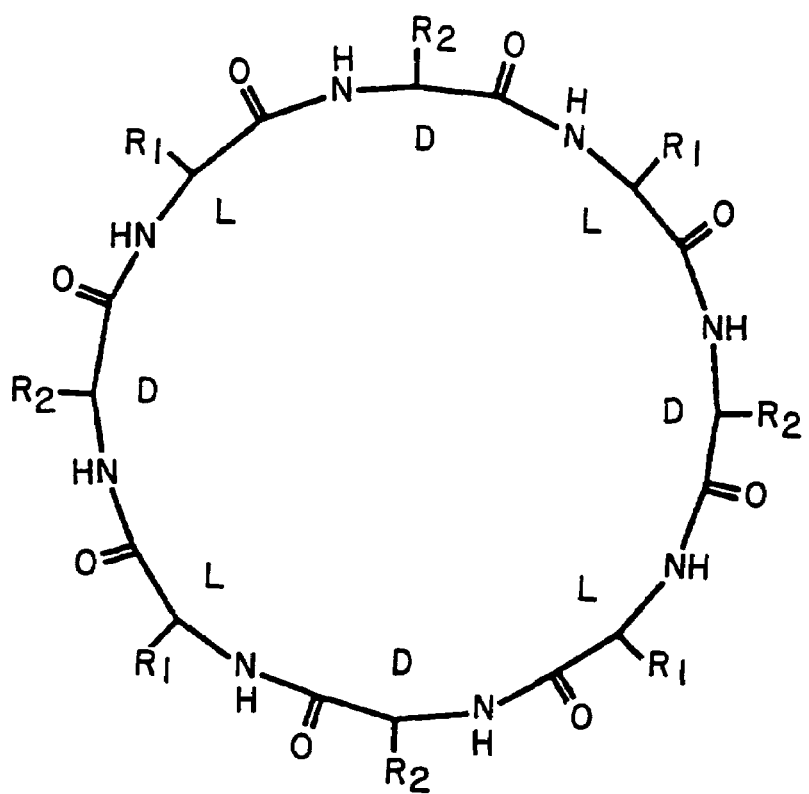
Figure 3C:
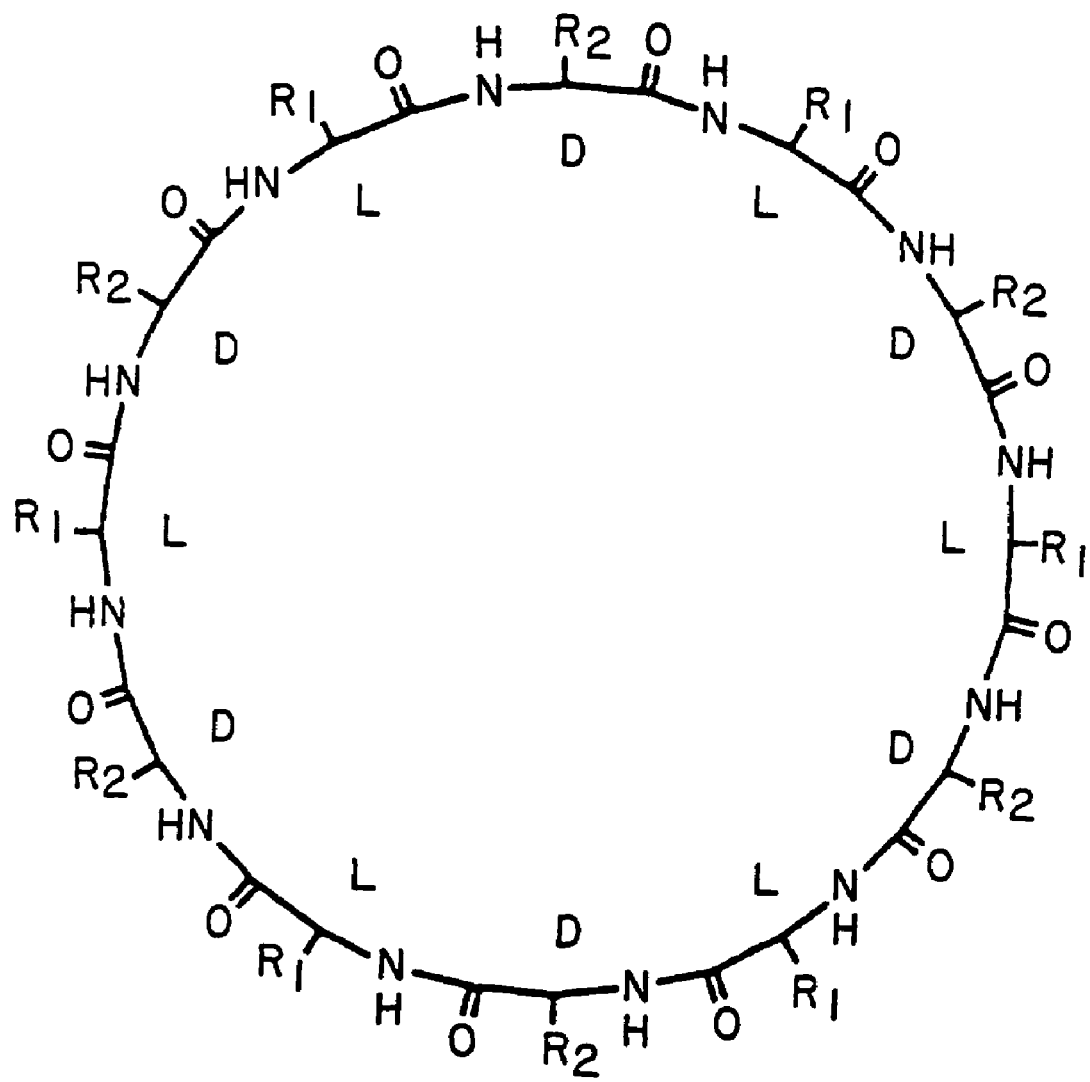

The self-assembled channels have two important and unique structural features which are pertinent hereto. One feature is that the channel pore size can be easily tailored by choosing an appropriate ring size for the cyclic peptide subunit (FIG. 3). This allows for the design of shape-selective membrane pore structures. The second feature, which deserves a brief explanation, has to do with channel gating-the process by which molecular transport across the channel is turned on or off. It is evident from FIG. 4 that the two subunits at the channel entrance, i.e., the "cap" position, are unique with respect to their mode of interaction with the other subunits as well as the micro-environment in which they reside. The peptide subunits at the cap position participate in backbone-backbone hydrogen bonding with only one other subunit and on only one side of the backbone structure. The cap subunits also reside in the amphiphilic micro-environment of the lipid-water interface. These unique characteristics can be exploited for the design of gated membrane channels in the following fashion. In order to ensure segregation of the cap subunits from the other channel forming subunits, one face of the backbone structure can be blocked from participating in inter-subunit hydrogen bonding interactions simply by alkylating the backbone amide nitrogen functionalities at the homochiral residues. Such N-alkylated species not only lack hydrogen bonding donor capability on one face of the disk structure but also the severe steric interaction imposed by the N-alkyl substituents effectively prevents the participation of the peptide subunit in bi-directional hydrogen bonding stacking interactions. Therefore, such N-alkylated subunits can only reside at the cap positions. In addition, side chains capable of interacting with polar lipid head groups may also be introduced to ensure its proper positioning at the lipid surface. As illustrated in FIG. 5, Amide nitrogen alkylation in addition to its hydrogen bonding disruptive capability, also serves another important role, i.e., it provides a simple strategy for designing gated membrane channels. In general, a wide variety of bi- or multi-dentate small-molecule receptors may be introduced at the channel entrance through N-alkylation, as illustrated in FIG. 6.

Figure 7:
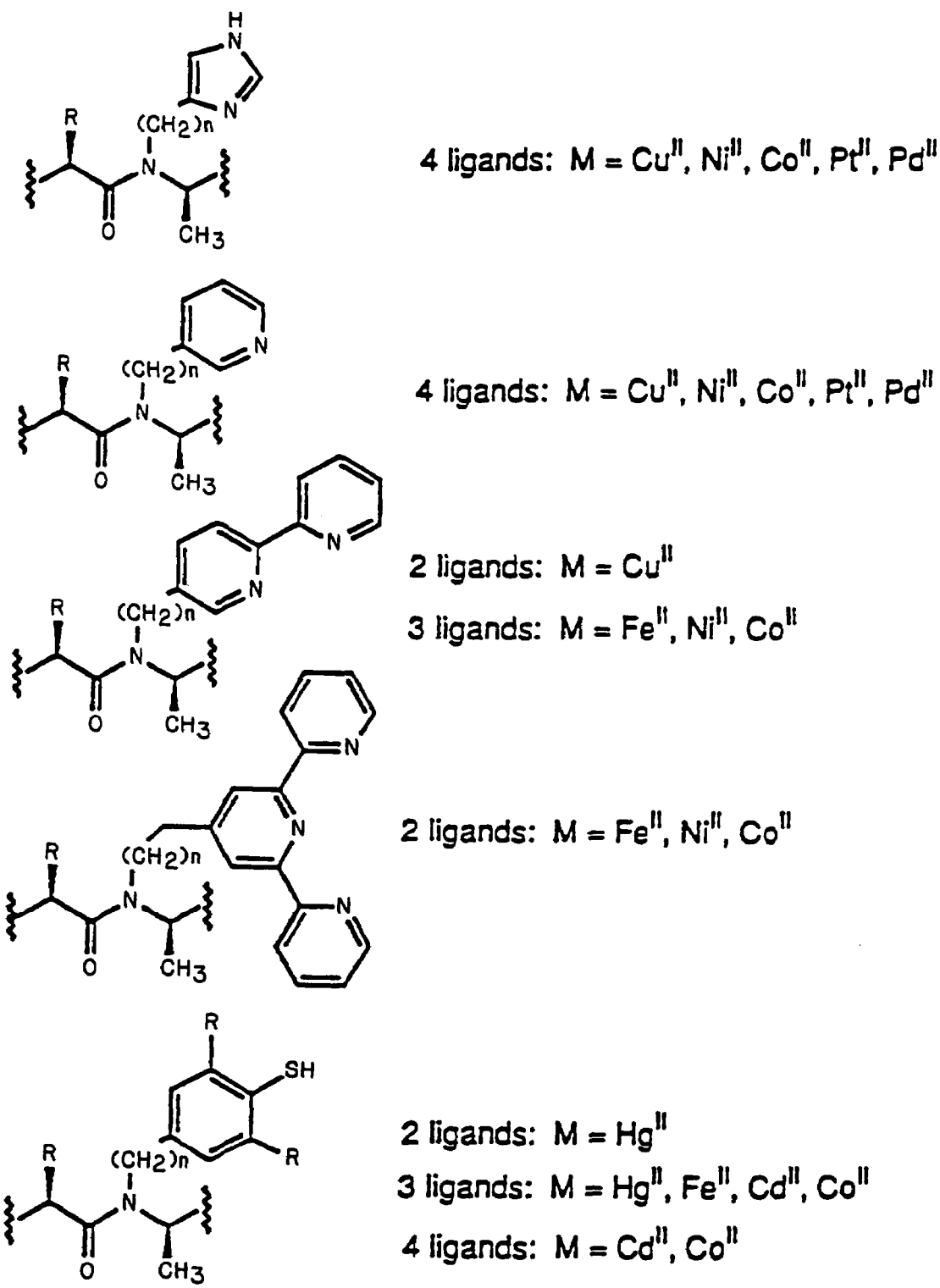
FIG. 7 illustrates preferred ligands for use in the construction of ion-gated membrane channels and their anticipated metal ion selectivity.

FIG. 7, illustrates that this simple anchoring motif can be employed with a number of transition metal ion binding sites. Channels structures assembled in this way, are blocked (in the "off" position) in the presence of transition metal ions toward molecular transport due to the steric hindrance imposed by the metal ion-ligand interactions at the channel entrance, as illustrate in FIG. 8. Such a strategy can also be employed in the design of highly selective and sensitive ion sensors.

Method:

The peptide can be synthesized by the solid phase method disclosed by Rovero, P. et al. (1991), *Tetrahedron Lett.*, 32, 2639-2642 and characterized by $^1$H-NMR spectroscopy, elemental analysis, and ion-spray mass spectrometry. Although a variety of conditions may be used in the self-assembly of cyclic peptide tubes, the following procedure has provided the most consistent results. Approximately 25 mg/ml suspension of peptide subunit is clarified by the addition of 2.5 equivalents of NaOH. The resulting peptide solution was centrifuged to remove traces of solid matter and then acidified by the addition of ⅓ volume of 1% trifluoroacetic acid in acetonitrile. Particles of cyclic peptide tubes gradually form as a white suspension over a period of hours cyclic peptide tubes may then be collected by centrifugation and washed repeatedly with distilled water to remove excess acids and salts. For electron microscopy and diffraction studies, a suspension of particles of cyclic peptide tubes is sonicated briefly and small drops applied to glow discharged carbon support films on EM grids. Excess liquid is removed by blotting and the grids frozen in liquid ethane slush according to the method disclosed by Adrian, M. et al., (1984) *Nature* 308, 32-36 and Milligan, R. A. et al., (1984) *Ultramicroscopy* 13, 1-10. Grids are mounted in a Gatan cold stage and examined in a Philips CM12 electron microscope operating at 120 kV. The specimen temperature was −175° C. during examination and imaging. Images are recorded at 35000× using strict low dose conditions at various defocus levels. For image analysis, micrographs are converted to optical density arrays using a Perkin-Elmer scanning microdensitometer with spot and step sizes equal to 2.86 Å at the specimen. Using the SUPRIM program package disclosed by Schroeter, J. P. et al. (1992), *J. Structural Biology* 109, 235-247, a number of small areas from a single TEM image are rotationally and translationally aligned and then averaged.

SYNTHETIC METHODS

Synthesis of Linear Peptides:

The linear form of the target sequence may be synthesized according to conventional solid-phase methods and then cyclized in solution to furnish the desired cyclic peptide subunit. A preferred method for synthesizing linear peptides is provided as follows:

Step A: The C-terminal amino acid residue (aa.1) of the target linear peptide is attached to a PAM resin (phenyl-acetamido-methyl). Hydroxymethyl PAM resin is a preferred PAM resin. Prior to use, it is washed 4 times in DMF. A N-Boc-aa.1 (N-tert-butoxycarbonyl amino acid) is then linked to the washed PAM resin to form Boc-aa.1-PAM resin. Linkage is achieved by combining the PAM resin with 4 equivalents of N-Boc-amino acid (D or L), 3.8 equivalents of HBTU (2-(1H-benzotriazol-1-yl)-1,1,3,3-tetramethyluronium tetrafluoroborate), and 6 equivalents of DIEA (N,N-diisopropylethylamine) in DMF. The resultant mixture is then shaken for 1 hour. If the C-terminal amino acid residue (aa.1) of the target linear peptide includes a potentially reactive side group, the side group is first blocked by conventional blocking agent prior to its attachment to the PAM resin. After reaction is complete, the product PAM resin is washed 3 times in DMF for 1 minute.

Step B: Because the product mixture will include a component of unreacted PAM resin, the PAM resin then is capped by mixing it with 20 equivalents of trimethylacetic anhydride and 10 equivalents of DIEA in DMF and shaking the resultant mixture overnight. The capped PAM resin bearing an N-Boc-amino acid residue is then washed 3 times in DMF and 3 further times in $CH_2Cl_2$.

Step C: The protected amino group of the Boc-aa.1-PAM-resin is then deprotected by treatment with neat TFA to form aa.1-PAM-resin. Step D: The deprotected Boc-aa.1-PAM-resin is then coupled to the second amino acid residue (aa.2), i.e, the amino acid residue once removed from the C-terminus of the target linear peptide, to form Boc-aa.2-aa.1-PAM-resin. The second amino acid residue (aa.2) has a chirality opposite the chirality of the C-terminal amino acid residue (aa.1), i.e., if aa.1 has a D chirality, aa.2 has an L chirality; if aa.1 has an L chirality, aa.2 has an D chirality. The deprotected Boc-amino acid-PAM-resin of step C is combined with 4 equivalents of N-Boc-aa.2, 3.8 equivalents of HBTU (2-(1H-benzotriazol-1-yl)-1,1,3,3-tetramethyluronium tetrafluoroborate), and 6 equivalents of DIEA (N,N-diisopropylethylamine) in DMF. The reaction mixture is then shaken for one hour.

Step E: The protected amino group of the Boc-aa.2-aa.1-PAM-resin is then deprotected by treatment with neat TFA to produce aa.2-aa.1-PAM-resin.

Step F: Steps D and E are then repeated as required to couple the third and subsequent amino acid residues in succession to the nascent peptide chain to form a reaction product having the structure aa.n-aa(n-1)- . . . aa.1-PAM-resin. The chirality of the even amino acids is opposite the charity of the odd amino acids.

Step G: After the synthesis of the target linear peptide is complete, it is cleaved from the PAM resin. Cleavage is achieved by treatment of the PAM-resin with a 10:1:0.5 mixture of HF, anisole, and dimethylsulfide at 0° C. for 1 hour. The cleavage product may then be extracted from the reaction mixture with aqueous acetic acid (50% v/v) and lyophilized. If the target linear peptide includes protected side groups, these side groups may be deprotected at this time. The product may then be verified by mass spectrometry.

Synthesis of Selectively N-Alkylated Linear Peptides:

The linear form of selectively N-alkylated target peptides may be synthesized according to a modification of conventional solid-phase methods of peptide synthesis. The linear form of selectively N-alkylated target peptides are then cyclized in solution to furnish the desired selectively N-alkylated cyclic peptide. The method for synthesizing linear form of selectively N-alkylated target peptides employs selectively N-alkylated N-Boc-amino acids. Preferred methods for synthesizing these N-alkylated amino acids and selectively N-alkylated linear peptides are provided as follows:

N-Alkylated amino acids may be synthesized according to the method of S.T. Cheung et al. (*Canadian Journal of Chemistry* (1977), vol. 55, p 906; *Canadian Journal of Chemistry* (1977), vol. 55, p 911; and *Canadian Journal of Chemistry* (1977), vol. 55, p 916.) Briefly, 8 equivalents of methyl iodide were combined with tetrahydrofuran (THF) at 0° C. under nitrogen and stirred to form a suspension. Other alkyl iodides and alkyl bromides may be substituted for the methyl iodide. To this suspension was added 1 equivalent of N-Boc-aa (N-tert-butoxycarbonyl amino acid) as a solid and 3 equivalents of sodium hydride. The resulting mixture was then stirred at room temperature under nitrogen for 24 hours. After 24 hours, excess NaH was quenched by the careful addition of an $H_2O$ to the reaction mixture. The mixture was then evaporated and the oily residue partitioned between $Et_2O$ and water. The Et2O layer was then washed with aqueous $NaHCO_3$. The combined aqueous extracts were then acidified to pH 3 with aqueous citric acid (5%). The acidified product was then extracted into EtOAc. The combined EtOAc layer was then serially washed with $H_2O$, aqueous sodium thiosulfate, $H_2O$, and brine. The product was then dried over $MgSO_4$ and subsequently recrystallized. A typical yield is 86%.

Selectively N-alkylated linear peptides may be synthesized by a modification of the method provided above for the synthesis of non-N-methylated linear peptides. N-Alkylated N-Boc-amino acids are less reactive with respect to coupling reactions as compared to non-N-alkylated N-Boc amino acids. As a consequence, coupling reactions involving N-alkylated N-Boc-amino acids may be less efficient. Accordingly, in order to achieve a high over all yield, it is often useful to follow up each coupling reaction with one or more recoupling reactions.

A selectively N-alkylated target peptide may be synthesized as follows:

Step A: The C-terminal amino acid residue (aa.1) of the target linear peptide is attached to a PAM resin (phenylacetamido-methyl). Hydroxymethyl PAM resin is a preferred PAM resin. Prior to use, it is washed 4 times in DMF. A N-Boc-aa.1 (N-tert-butoxycarbonyl amino acid) or a N-alkylated N-Boc-aa.1 is then linked to the washed PAM resin to form Boc-aa.1-PAM resin. Linkage is achieved by combining the PAM resin with 4 equivalents of N-Boc-aa.1 (D or L) or N-alkylated N-Boc-aa.1 (D or L), 3.8 equivalents of HBTU (2-(1H-benzotriazol-1-yl)-1,1,3,3-tetramethyluronium tetrafluoroborate), and 6 equivalents of DIEA (N,N-diisopropylethylamine) in DMF. The resultant mixture is then shaken for 1 hour. If the C-terminal amino acid residue (aa.1) of the target linear peptide includes a potentially reactive side group, the side group is first blocked by conventional blocking agent prior to its attachment to the PAM resin. After reaction is complete, the product PAM resin is washed 3 times in DMF for 1 minute.

Step B: Because the product mixture will include a component of unreacted PAM resin, the PAM resin then is capped by mixing it with 20 equivalents of trimethylacetic anhydride and 10 equivalents of DIEA in DMF and shaking the resultant mixture overnight. The capped PAM resin bearing an N-Boc-amino acid residue or N-alkylated N-Boc amino acid is then washed 3 times in DMF and 3 further times in $CH_2Cl_2$.

Step C: The protected amino group of the Boc-aa.1-PAM-resin or N-alkylated N-Boc-aa.1-Pam resin is then deprotected by treatment with neat TFA to form aa.1-PAM-resin or N-alkylated aa.1-PAM resin, respectively.

Step D: The deprotected Boc-aa.1-PAM-resin or N-alkylated aa.1-PAM resin is then coupled to the second amino acid residue (aa.2 or N-alkyl aa.2), i.e, the amino acid residue once removed from the C-terminus of the target linear peptide, to form Boc-aa.2-aa.1-PAM-resin, Boc-aa.2-N-alkyl aa.1-PAM-resin, N-alkyl Boc-aa.2-aa.1-PAM-resin, or N-alkyl Boc-aa.2-N-alkyl aa.1-PAM-resin. The second amino acid residue (aa.2) has a chirality opposite the chirality of the C-terminal amino acid residue (aa.1), i.e., if aa.1 has a D chirality, aa.2 has an L chirality; if aa.1 has an L chirality, aa.2 has an D chirality. The deprotected Boc-aa.1-PAM-resin or N-alkyl Boc-aa.1-PAM-resin of step C is combined with 4 equivalents of N-Boc-aa.2 or N-alkyl N-Boc-aa.2, 3.8 equivalents of HBTU (2-(1H-benzotriazol-1-yl)-1,1,3,3-tetramethyluronium tetrafluoroborate), and 6 equivalents of DIEA (N,N-diisopropylethylamine) in DMF. The reaction mixture is then shaken for one hour. If coupling is occurring with N-alkyl Boc-aa.1-PAM-resin, the efficiency of the initial coupling reaction may be relatively low. In this event, an aliquot of the reaction mixture may then be assayed by the chloranil test. If the test is positive, the reaction product is treated second time with the above reactants to achieve an essentially quantitative yield of Boc-aa.2-N-alkyl aa.1-PAM-resin or N-alkyl Boc-aa.2-N-alkyl aa.1-PAM-resin.

Step E: The protected amino group of the product of Step D, i.e., Boc-aa.2-aa.1-PAM-resin, Boc-aa.2-N-alkyl aa.1-PAM-resin, N-alkyl Boc-aa.2-aa.1-PAM-resin, or N-alkyl Boc-aa.2-N-alkyl aa.1-PAM-resin, is then deprotected by treatment with neat TFA to produce aa.2-aa.1-PAM-resin, aa.2-N-alkyl aa.1-PAM-resin, N-alkyl-aa.2-aa.1-PAM-resin, or N-alkyl-aa.2-N-alkyl aa.1-PAM-resin.

Step F: Steps D and E are then repeated as required to couple the third and subsequent amino acid residues in succession to the nascent peptide chain to form a target selectively N-alkylated linear peptide linked to resin.

Step G: After the synthesis of the target selectively N-alkylated linear peptide is complete, it is cleaved from the PAM resin. Cleavage is achieved by treatment of the PAM-resin with a 10:1:0.5 mixture of HF, anisole, and dimethylsulfide at 0° C. for 1 hour. The cleavage product may then be extracted from the reaction mixture with aqueous acetic acid (50% v/v) and lyophilized. If the target selectively N-alkylated linear peptide includes protected side groups, these side groups may be deprotected at this time. The product may then be verified by mass spectrometry.

Synthesis of Linear Peptide Precursors of Gated Cyclic Peptides:

The linear form of selectively N-substituted target peptides may be synthesized according to a modification of conventional solid-phase methods of peptide synthesis. Gated cyclic peptides can be formed by cyclization of linear peptides selectively N-substituted with respect to their peptide backbone amino groups. Preferred substitutions for forming gated cyclic peptides are illustrated in FIG. 7. Each of the preferred substitutions includes a heterocyclic structure linked via an alkyl chain, viz. N—$(CH_2)_n$-heterocycle, where N is a peptide amino nitrogen and "n" lies between 1 and 5. The distal end of the alkyl chain is bonded to a selected peptide amino nitrogen on the peptide backbone. In the preferred embodiment, all N-substitutions are on the same face of the cyclic peptide. Preferred heterocyclic structure include imidazole, pyridine, 2,2':6,2"terpyridine, and 2,2'-bipyridine.

N-substituted N-Boc-amino acids are employed for synthesizing the linear form of selectively N-substituted target peptides. The method of S. T. Cheung et al. (*Canadian Journal of Chemistry* (1977), vol. 55, p 906; *Canadian Journal of Chemistry* (1977), vol. 55, p 911; and *Canadian Journal of Chemistry* (1977), vol. 55, p 916.) may be employed for synthesizing these N-substituted amino acids. The synthetic method employs a haloalkyl-heterocycle as a substrate, i.e, X—$(CH_2)_n$-heterocycle, where X is a halogen and "n" lies between 1 and 5. Preferred halogens include bromine and iodine. Preferred alkyl groups include $(CH_2)_n$ were n lies between 1 and 5. The halogen is positioned at one end of the alkyl chain distal with respect to the attachment of the alkyl chain to the heterocycle.

Preferred haloalkyl-heterocyclic substrates may be obtained as follows:

4-(Bromomethyl)-1-H imidazole may be synthesized according to the method of D. E. Ryono et al. in German Patent DE 3309014 (Sep. 29, 1983), claiming priority from U.S. patent application Ser. No. 356941 (Mar. 15, 1982) or according to the method of W. Schunack in *Arch. Pharm.* (1974), vol. 307(1), pages 46-51.

4-(2-Bromoethyl)-1-H imidazole may be synthesized according to the method of E. T Chen in *Anal. Chem.* (1993), vol. 65(19), pages 2563-2567.

4-(3-Bromopropyl)-1-H imidazole may be synthesized according to the method of P. Franchetti et al. in *Farmaco, Ed. Sci., vol.* 29(4), pages 309-316 and according to the method of W. M. P. B. Menge et al. in *J. Labelled Compd. Radiopharm.* (1992), vol. 31(10), pages 781-786.

3-(Bromomethyl)-pyridine may be synthesized according to the method of R. Jokela et al. in *Heterocycles* 1985, vol. 23(7), pages 1707-22.

3-(2-Bromoethyl)-pyridine may be synthesized according to the method of A. Lochead et al. in European Patent Application No. EP 320362 (Jun. 14, 1989) and EP 88-403079 (Dec. 6, 1988), claiming priority from French patent application FR 87-17044 or according to the method of R. A. R. Bruneau et al in European Patent application EP 284174 (Sep. 28, 1988) and EP 88-300281 (Jan. 14, 1988), claiming priority from EP 87-400122 (Jan. 19, 1987) and EP 87-401798 (Jul. 31, 1987).

3-(3-Bromopropyl)-pyridine may be synthesized according to the method of A. W. Van der Made et al. in *Recl. Trav. Chim. Pays-Bas* (1990), vol. 109(11), pages 537-551.

3-(4-Bromobutyl)-pyridine may be synthesized according to the method of J. W. Tilley et al. in the *Journal of Organic Chemistry* (1987), vol. 52(12), pages 2469-2474 or according to the method of U. R. Patel in U.S. Pat. No. 4,855,430 (Aug. 8, 1989) or according to the method of M. Carson et al. in U.S. Pat. No. 4,663,332 (May 5, 1987).

3-(Iodomethyl)-pyridine may be synthesized according to the method of G. G. Abashev in USSR Patent No. SU 1692985 A1 (Nov. 23, 1991).

4'-(4-Bromobutyl)-2,2':6,2"-terpyridine may be synthesized according to the method of J. K. Bashkin in PCT International Patent Application No. WO 9119730 A1 (Dec. 26, 1991) or WO 91-US3880 (Jun. 3, 1991).

5-(Bromomethyl)-2,2'-bipyridine may be synthesized according to the method of J. Uenishi et al. in the *Journal of organic Chemistry* (1993), vol. 58(16), pages 4382-4388 or according to the method of B. Imperiali et al. in the *Journal of Organic Chemistry* (1993), vol. 56(6), pages 1613-1616.

Briefly, 8 equivalents of a haloalkyl-heterocyclic substrate, as indicated above, is combined with tetrahydrofuran (THF) at 0° C. under nitrogen and stirred to form a suspension. To this suspension is added 1 equivalent of N-Boc-aa (N-tert-butoxycarbonyl amino acid) as a solid and 3 equivalents of sodium hydride. The resulting mixture is then stirred at room temperature under nitrogen for 24 hours. After 24 hours, excess NaH is quenched by the careful addition of an $H_2O$ to the reaction mixture. The mixture is then evaporated and the oily residue partitioned between $Et_2O$ and water. The $Et_2O$ layer is then washed with aqueous $NaHCO_3$. The combined aqueous extracts are then acidified to pH 3 with aqueous citric acid (5%). The acidified product is then extracted into EtOAc. The combined EtOAc layer is then serially washed with $H_2O$, aqueous sodium thiosulfate, $H_2O$, and brine. The product is then dried over $MgSO_4$ and subsequently recrystallized.

Selectively N-substituted linear peptides may be synthesized according to the method provided above for the synthesis of N-alkylated or N-methylated linear peptides. If an N-substituent is bulky, the N-substituted N-Boc-amino acids can be even less reactive with respect to coupling reactions than N-methyl N-Boc amino acids due to steric hinderance. As a consequence, coupling reactions involving N-substituted N-Boc-amino acids may be slow and relatively inefficient. Accordingly, in order to achieve a high over all yield, it is often useful to follow up each coupling reaction with repeated recoupling reactions.

A selectively N-substituted target peptide may be synthesized as follows:

Step A: The C-terminal amino acid residue (aa.1) of the target linear peptide is attached to a PAM resin (phenylacetamido-methyl). Hydroxymethyl PAM resin is a preferred PAM resin. Prior to use, it is washed 4 times in DMF. A N-Boc-aa.1 (N-tert-butoxycarbonyl amino acid) or a N-substituted N-Boc-aa.1 is then linked to the washed PAM resin to form Boc-aa.1-PAM resin. Linkage is achieved by combining the PAM resin with 4 equivalents of N-Boc-aa.1 (D or L) or N-substituted N-Boc-aa.1 (D or L), 3.8 equivalents of HBTU (2-(1H-benzotriazol-1-yl)-1,1,3,3-tetramethyluronium tetrafluoroborate), and 6 equivalents of DIEA (N,N-diisopropylethylamine) in DMF. The resultant mixture is then shaken for 1 hour. If the C-terminal amino acid residue (aa.1) of the target linear peptide includes a potentially reactive side group, the side group is first blocked by conventional blocking agent prior to its attachment to the PAM resin. After reaction is complete, the product PAM resin is washed 3 times in DMF for 1 minute.

Step B: Because the product mixture will include a component of unreacted PAM resin, the PAM resin then is capped by mixing it with 20 equivalents of trimethylacetic anhydride and 10 equivalents of DIEA in DMF and shaking the resultant mixture overnight. The capped PAM resin bearing an N-Boc-amino acid residue or N-substituted N-Boc amino acid is then washed 3 times in DMF and 3 further times in $CH_2Cl_2$.

Step C: The protected amino group of the Boc-aa.1-PAM-resin or N-substituted N-Boc-aa.1-Pam resin is then deprotected by treatment with neat TFA to form aa.1-PAM-resin or N-substituted aa.1-PAM resin, respectively.

Step D: The deprotected Boc-aa.1-PAM-resin or N-substituted aa.1-PAM resin is then coupled to the second amino acid residue (aa.2 or N-alkyl aa.2), i.e, the amino acid residue once removed from the C-terminus of the target linear peptide, to form Boc-aa.2-aa.1-PAM-resin, Boc-aa.2-N-alkyl aa.1-PAM-resin, N-alkyl Boc-aa.2-aa.1-PAM-resin, or N-alkyl Boc-aa.2-N-alkyl aa.1-PAM-resin. The second amino acid residue (aa.2) has a chirality opposite the chirality of the C-terminal amino acid residue (aa.1), i.e., if aa.1 has a D chirality, aa.2 has an L chirality; if aa.1 has an L chirality, aa.2 has an D chirality. The deprotected Boc-aa.1-PAM-resin or N-alkyl Boc-aa.1-PAM-resin of step C is combined with 4 equivalents of N-Boc-aa.2 or N-alkyl N-Boc-aa.2, 3.8 equivalents of HBTU (2-(1H-benzotriazol-1-yl)-1,1,3,3-tetramethyluronium tetrafluoroborate), and 6 equivalents of DIEA (N,N-diisopropylethylamine) in DMF. The reaction mixture is then shaken for one hour. If coupling is occurring with N-alkyl Boc-aa.1-PAM-resin, the efficiency of the initial coupling reaction may be relatively low. In this event, an aliquot of the reaction mixture may then be assayed by the chloranil test. If the test is positive, the reaction product is treated second time with the above reactants to achieve an essentially quantitative yield of Boc-aa.2-N-alkyl aa.1-PAM-resin or N-alkyl Boc-aa.2-N-alkyl aa.1-PAM-resin.

Step E: The protected amino group of the product of Step D, i.e., Boc-aa.2-aa.1-PAM-resin, Boc-aa.2-N-alkyl aa.1-PAM-resin, N-alkyl Boc-aa.2-aa.1-PAM-resin, or N-alkyl Boc-aa.2-N-alkyl aa.1-PAM-resin, is then deprotected by treatment with neat TFA to produce aa.2-aa.1-PAM-resin, aa.2-N-alkyl aa.1-PAM-resin, N-alkyl-aa.2-aa.1-PAM-resin, or N-alkyl-aa.2-N-alkyl aa.1-PAM-resin.

Step F: Steps D and E are then repeated as required to couple the third and subsequent amino acid residues in succession to the nascent peptide chain to form a target selectively N-substituted linear peptide linked to resin.

Step G: After the synthesis of the target selectively N-substituted linear peptide is complete, it is cleaved from the PAM resin. Cleavage is achieved by treatment of the PAM-resin with a 10:1:0.5 mixture of HF, anisole, and dimethylsulfide at 0° C. for 1 hour. The cleavage product may then be extracted from the reaction mixture with aqueous acetic acid (50% v/v) and lyophilized. If the target selectively N-substituted linear peptide includes protected side groups, these side groups may be deprotected at this time. The product may then be verified by mass spectrometry.

Cyclization of Linear Peptides:

The target linear peptides, selectively N-alkylated target linear peptides, and selectively N-substituted target linear peptides, whose syntheses are described above, may each be cyclized according to the following protocol:

A solution of the linear peptide in DMF (1 mM) is treated with TBTU (2-(1H-Benzotriazol-1-yl)-1,1,3,3-tetramethyluronium tetrafluoroborate, 3 mM), HOBt (1-Hydroxybenzotriazole, 3 mM) and DIEA (diisopropylethylamine, 1% v/v) at 5° C. for 12 hours to give the desired cyclic peptide monomer. The product may be purified by reverse-phase HPLC purification. A typical yield for the cyclization of N-methylated linear peptides octomer is 70% yield.

Alternative Method for Peptide Synthesis and Cyclization:

Alternatively, peptides containing an Asp residue can be synthesized and cyclized by the solid phase method disclosed by Rovero, P. et al. (1991), *Tetrahedron Lett.,* 32, 2639-2642. Briefly, Boc-Asp (N-tert-butoxycarbonyl aspartic acid) is linked to PAM resin (phenyl-acetamido-methyl) through the β-carboxylic function while the α-carboxylic groups is protected as a fluorenylmethyl ester (OFm). Boc-Asp(β-PAM-resin)OFm may be purchased from Bachem A G, Switzerland. A linear peptide having the D-L chirality motif may then be built upon the Boc-Asp(β-PAM-resin) OFm according to the classical Boc/Benzyl strategy using an automatic or semi-automatic peptide synthesizer, e.g., Labortec SP 640. Synthesis is achieved by consecutively adding Boc-protected amino acids according to the BOP coupling procedure, i.e., 3 equivalents Boc-amino acid, 3 equivalent BOP and 6 equivalent DIEA in DMF for 1 hour. Completeness may be achieved by repeating each coupling twice. Once the synthesis of the linear peptide is complete, it ready for cyclization. Prior to cyclization, the N-terminal amino group was deprotected with TFA and the C-terminal fluorenylmethyl ester was deblocked with piperidine (20% v/v piperidine in DMF) for 3+7; minutes. Cyclization was then achieved by treatment with 3 equivalents of BOP (benzotriazolyl-N-oxy-tris(dimethylamino)-phosphonium hexafluorophosphate) and 6 equivalents of DIEA (N,N-diisopropylethylamine) in DMF for 3 hours. If the cyclization reaction is incomplete, the BOP treatment may be repeated. Deprotection of the side chains and cleavage of the cyclic peptide from the resin may be achieved by treatment with a 10:1:0.5 mixture of HF, anisole, and dimethylsulfide at 0° C. for 1 hour. The product may then be extracted from the reaction mixture with aqueous acetic acid (50% v/v) and lyophilized.

Capped and gated cyclic peptides may also be synthesized according to the above method by cyclizing the corresponding N-substituted linear peptides.

SEQUENCE LISTING

```
<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: Length:  8 amino acids
      Type:   amino acids
      Topology:   circular, cyclic peptide
<220> FEATURE:
<221> NAME/KEY: MOD_RES
<222> LOCATION: 2
<223> OTHER INFORMATION: D-alanine or D-Ala which corresponds to the
      D-isomer of the amino acid alanine
<220> FEATURE:
<221> NAME/KEY: MOD_RES
<222> LOCATION: 4
<223> OTHER INFORMATION: D-alanine or D-Ala which corresponds to the
      D-isomer of the amino acid alanine
<220> FEATURE:
<221> NAME/KEY: MOD_RES
<222> LOCATION: 6
<223> OTHER INFORMATION: D-alanine or D-Ala which corresponds to the
      D-isomer of the amino acid alanine
<220> FEATURE:
<221> NAME/KEY: MOD_RES
<222> LOCATION: 8
<223> OTHER INFORMATION: D-alanine or D-Ala which corresponds to the
      D-isomer of the amino acid alanine

<400> SEQUENCE: 1

Gln Ala Glu Ala Gln Ala Glu Ala
 1               5

<210> SEQ ID NO 2
<211> LENGTH: 8
```

```
<212> TYPE: PRT
<213> ORGANISM: Artificial Sequence
<220> FEATURE:
<223> OTHER INFORMATION: Length:  8 amino acids
      Type:  amino acids
      Topology:  circular, cyclic peptide
<220> FEATURE:
<221> NAME/KEY: MOD_RES
<222> LOCATION: 2
<223> OTHER INFORMATION: D-alanine or D-Ala which corresponds to the
      D-isomer of the amino acid alanine
<220> FEATURE:
<221> NAME/KEY: MOD_RES
<222> LOCATION: 4
<223> OTHER INFORMATION: D-alanine or D-Ala which corresponds to the
      D-isomer of the amino acid alanine
<220> FEATURE:
<221> NAME/KEY: MOD_RES
<222> LOCATION: 6
<223> OTHER INFORMATION: D-alanine or D-Ala which corresponds to the
      D-isomer of the amino acid alanine
<220> FEATURE:
<221> NAME/KEY: MOD_RES
<222> LOCATION: 8
<223> OTHER INFORMATION: D-alanine or D-Ala which corresponds to the
      D-isomer of the amino acid alanine

<400> SEQUENCE: 2

Gln Ala Gln Ala Gln Ala Gln Ala
 1               5

<210> SEQ ID NO 3
<211> LENGTH: 8
<212> TYPE: PRT
<213> ORGANISM: Artificial Sequence
<220> FEATURE:
<223> OTHER INFORMATION: Length:  8 amino acids
      Type:  amino acids
      Topology:  Circular
<220> FEATURE:
<221> NAME/KEY: MOD_RES
<222> LOCATION: 2
<223> OTHER INFORMATION: D-leucine or D-Leu which corresponds to the
      D-isomer
      of the amino acid leucine
<220> FEATURE:
<221> NAME/KEY: MOD_RES
<222> LOCATION: 4
<223> OTHER INFORMATION: D-leucine or D-Leu which corresponds to the
      D-isomer
      of the amino acid leucine
<220> FEATURE:
<221> NAME/KEY: MOD_RES
<222> LOCATION: 6
<223> OTHER INFORMATION: D-leucine or D-Leu which corresponds to the
      D-isomer
      of the amino acid leucine
<220> FEATURE:
<221> NAME/KEY: MOD_RES
<222> LOCATION: 8
<223> OTHER INFORMATION: D-leucine or D-Leu which corresponds to the
      D-isomer
      of the amino acid leucine

<400> SEQUENCE: 3

Gln Leu Gln Leu Gln Leu Gln Leu
 1               5

<210> SEQ ID NO 4
<211> LENGTH: 8
<212> TYPE: PRT
<213> ORGANISM: Artificial Sequence
<220> FEATURE:
<223> OTHER INFORMATION: Length:  8 amino acids
      Type:  amino acids
```

```
          Topology: Circular
<220> FEATURE:
<221> NAME/KEY: MOD_RES
<222> LOCATION: 2
<223> OTHER INFORMATION: D-valine or D-Val which corresponds to the
      D-isomer of the amino acid valine
<220> FEATURE:
<221> NAME/KEY: MOD_RES
<222> LOCATION: 4
<223> OTHER INFORMATION: D-valine or D-Val which corresponds to the
      D-isomer of the amino acid valine
<220> FEATURE:
<221> NAME/KEY: MOD_RES
<222> LOCATION: 6
<223> OTHER INFORMATION: D-valine or D-Val which corresponds to the
      D-isomer of the amino acid valine
<220> FEATURE:
<221> NAME/KEY: MOD_RES
<222> LOCATION: 8
<223> OTHER INFORMATION: D-valine or D-Val which corresponds to the
      D-isomer of the amino acid valine

<400> SEQUENCE: 4

Gln Val Gln Val Gln Val Gln Val
 1               5

<210> SEQ ID NO 5
<211> LENGTH: 8
<212> TYPE: PRT
<213> ORGANISM: Artificial Sequence
<220> FEATURE:
<223> OTHER INFORMATION: Length:  8 amino acids
      Type:  amino acids
      Topology: Circular
<220> FEATURE:
<221> NAME/KEY: MOD_RES
<222> LOCATION: 2
<223> OTHER INFORMATION: D-leucine or D-Leu which corresponds to the
      D-isomer of the amino acid leucine
<220> FEATURE:
<221> NAME/KEY: MOD_RES
<222> LOCATION: 4
<223> OTHER INFORMATION: D-leucine or D-Leu which corresponds to the
      D-isomer of the amino acid leucine
<220> FEATURE:
<221> NAME/KEY: MOD_RES
<222> LOCATION: 6
<223> OTHER INFORMATION: D-leucine or D-Leu which corresponds to the
      D-isomer of the amino acid leucine
<220> FEATURE:
<221> NAME/KEY: MOD_RES
<222> LOCATION: 8
<223> OTHER INFORMATION: D-leucine or D-Leu which corresponds to the
      D-isomer of the amino acid leucine

<400> SEQUENCE: 5

Phe Leu Phe Leu Phe Leu Phe Leu
 1               5

<210> SEQ ID NO 6
<211> LENGTH: 8
<212> TYPE: PRT
<213> ORGANISM: Artificial Sequence
<220> FEATURE:
<223> OTHER INFORMATION: Length:  8 amino acids
      Type:  amino acids
      Topology: Circular
<220> FEATURE:
<221> NAME/KEY: MOD_RES
<222> LOCATION: 2
<223> OTHER INFORMATION: D-Alanine or D-Ala which corresponds to the
      D-isomer of the amino acid alanine
<220> FEATURE:
<221> NAME/KEY: MOD_RES
<222> LOCATION: 4
```

```
<223> OTHER INFORMATION: D-Alanine or D-Ala which corresponds to the
      D-isomer of the amino acid alanine
<220> FEATURE:
<221> NAME/KEY: MOD_RES
<222> LOCATION: 6
<223> OTHER INFORMATION: D-Alanine or D-Ala which corresponds to the
      D-isomer of the amino acid alanine
<220> FEATURE:
<221> NAME/KEY: MOD_RES
<222> LOCATION: 8
<223> OTHER INFORMATION: D-Alanine or D-Ala which corresponds to the
      D-isomer of the amino acid alanine

<400> SEQUENCE: 6

Phe Ala Phe Ala Phe Ala Phe Ala
 1               5

<210> SEQ ID NO 7
<211> LENGTH: 8
<212> TYPE: PRT
<213> ORGANISM: Artificial Sequence
<220> FEATURE:
<223> OTHER INFORMATION: Length:  8 amino acids
      Type:  amino acids
      Topology:  Circular
<220> FEATURE:
<221> NAME/KEY: MOD_RES
<222> LOCATION: 2
<223> OTHER INFORMATION: N-Methyl-D-Alanine or N-Me-D-Ala which
      corresponds to the N-methylated derivative of the D-isomer of
      the amino acid alanine
<220> FEATURE:
<221> NAME/KEY: MOD_RES
<222> LOCATION: 4
<223> OTHER INFORMATION: N-Methyl-D-Alanine or N-Me-D-Ala which
      corresponds to the N-methylated derivative of the D-isomer of
      the amino acid alanine
<220> FEATURE:
<221> NAME/KEY: MOD_RES
<222> LOCATION: 6
<223> OTHER INFORMATION: N-Methyl-D-Alanine or N-Me-D-Ala which
      corresponds to the N-methylated derivative of the D-isomer of
      the amino acid alanine
<220> FEATURE:
<221> NAME/KEY: MOD_RES
<222> LOCATION: 8
<223> OTHER INFORMATION: N-Methyl-D-Alanine or N-Me-D-Ala which
      corresponds to the N-methylated derivative of the D-isomer of
      the amino acid alanine

<400> SEQUENCE: 7

Phe Ala Phe Ala Phe Ala Phe Ala
 1               5

<210> SEQ ID NO 8
<211> LENGTH: 12
<212> TYPE: PRT
<213> ORGANISM: Artificial Sequence
<220> FEATURE:
<223> OTHER INFORMATION: Length:  12 amino acids
      Type:  amino acids
      Topology:  Circular
<220> FEATURE:
<221> NAME/KEY: MOD_RES
<222> LOCATION: 2
<223> OTHER INFORMATION: D-Ala or the D-isomer of the amino acid alanine
<220> FEATURE:
<221> NAME/KEY: MOD_RES
<222> LOCATION: 4
<223> OTHER INFORMATION: D-Ala or the D-isomer of the amino acid alanine
<220> FEATURE:
<221> NAME/KEY: MOD_RES
<222> LOCATION: 6
<223> OTHER INFORMATION: D-Ala or the D-isomer of the amino acid alanine
<220> FEATURE:
```

```
<221> NAME/KEY: MOD_RES
<222> LOCATION: 8
<223> OTHER INFORMATION: D-Ala or the D-isomer of the amino acid alanine
<220> FEATURE:
<221> NAME/KEY: MOD_RES
<222> LOCATION: 10
<223> OTHER INFORMATION: D-Ala or the D-isomer of the amino acid alanine
<220> FEATURE:
<221> NAME/KEY: MOD_RES
<222> LOCATION: (12)...(12)
<223> OTHER INFORMATION: D-Ala or the D-isomer of the amino acid alanine

<400> SEQUENCE: 8

Gln Ala Glu Ala Gln Ala Glu Ala Gln Ala Glu Ala
 1               5                  10

<210> SEQ ID NO 9
<211> LENGTH: 8
<212> TYPE: PRT
<213> ORGANISM: Artificial Sequence
<220> FEATURE:
<223> OTHER INFORMATION: Length:  8 amino acids
      Type:   amino acids
      Topology:  Circular
<220> FEATURE:
<221> NAME/KEY: MOD_RES
<222> LOCATION: 2
<223> OTHER INFORMATION: D-Leu or the D-isomer of the amino acid leucine
<220> FEATURE:
<221> NAME/KEY: MOD_RES
<222> LOCATION: 4
<223> OTHER INFORMATION: D-Leu or the D-isomer of the amino acid leucine
<220> FEATURE:
<221> NAME/KEY: MOD_RES
<222> LOCATION: 6
<223> OTHER INFORMATION: D-Leu or the D-isomer of the amino acid leucine
<220> FEATURE:
<221> NAME/KEY: MOD_RES
<222> LOCATION: 8
<223> OTHER INFORMATION: D-Leu or the D-isomer of the amino acid leucine

<400> SEQUENCE: 9

Trp Leu Trp Leu Trp Leu Gln Leu
 1               5

<210> SEQ ID NO 10
<211> LENGTH: 10
<212> TYPE: PRT
<213> ORGANISM: Artificial Sequence
<220> FEATURE:
<223> OTHER INFORMATION: Length:  10 amino acids
      Type:   amino acids
      Topology:  Circular
<220> FEATURE:
<221> NAME/KEY: MOD_RES
<222> LOCATION: 2
<223> OTHER INFORMATION: D-Leu or the D-isomer of the amino acid leucine
<220> FEATURE:
<221> NAME/KEY: MOD_RES
<222> LOCATION: 4
<223> OTHER INFORMATION: D-Leu or the D-isomer of the amino acid leucine
<220> FEATURE:
<221> NAME/KEY: MOD_RES
<222> LOCATION: 6
<223> OTHER INFORMATION: D-Leu or the D-isomer of the amino acid leucine
<220> FEATURE:
<221> NAME/KEY: MOD_RES
<222> LOCATION: 8
<223> OTHER INFORMATION: D-Leu or the D-isomer of the amino acid leucine
<220> FEATURE:
<221> NAME/KEY: MOD_RES
<222> LOCATION: 10
<223> OTHER INFORMATION: D-Leu or the D-isomer of the amino acid leucine

<400> SEQUENCE: 10
```

```
Gln Leu Trp Leu Trp Leu Trp Leu Trp Leu
 1               5                  10

<210> SEQ ID NO 11
<211> LENGTH: 8
<212> TYPE: PRT
<213> ORGANISM: Artificial Sequence
<220> FEATURE:
<223> OTHER INFORMATION: Length:  8 amino acids
      Type:  amino acids
      Topology:  Circular
<220> FEATURE:
<221> NAME/KEY: MOD_RES
<222> LOCATION: 2
<223> OTHER INFORMATION: N-(4-Methyl-1H-imidazole)-D-
      Ala or the D-isomer of alanine with a
      4-methyl-1H-imidazole group on the nitrogen
<220> FEATURE:
<221> NAME/KEY: MOD_RES
<222> LOCATION: 4
<223> OTHER INFORMATION: N-(4-Methyl-1H-imidazole)-D-
      Ala or the D-isomer of alanine with a
      4-methyl-1H-imidazole group on the nitrogen
<220> FEATURE:
<221> NAME/KEY: MOD_RES
<222> LOCATION: 6
<223> OTHER INFORMATION: N-(4-Methyl-1H-imidazole)-D-
      Ala or the D-isomer of alanine with a
      4-methyl-1H-imidazole group on the nitrogen
<220> FEATURE:
<221> NAME/KEY: MOD_RES
<222> LOCATION: 8
<223> OTHER INFORMATION: N-(4-Methyl-1H-imidazole)-D-
      Ala or the D-isomer of alanine with a
      4-methyl-1H-imidazole group on the nitrogen

<400> SEQUENCE: 11

Phe Ala Phe Ala Phe Ala Phe Ala
 1               5
```

What is claimed is:

1. A method for constructing molecular tubes comprising the following steps:

Step A: providing a first solution having charged cyclic peptides solubilized therein, each of said cyclic peptides having one or more ionized amino acid residues for imparting a net charge to said charged cyclic peptides, said charged cyclic peptides being homodetic and having an amino acid sequence with a length between 6 and 16 amino acid residues, a repeating D-L chirality motif, and an even number of amino acid residues, wherein all of said ionized amino acid residues are either ionized acidic amino acid residues or ionized basic amino acid residues; and then Step B: neutralizing the charge of the charged cyclic peptides of said Step A by changing the pH of the first solution for forming a second solution having neutral cyclic peptides lacking a net charge and for promoting hydrogen bond formation; and then Step C: forming a suspension of molecular tubes within said second solution by allowing self-assembly of the neutral cyclic peptides with stacking of the neutral cyclic peptides upon one another in an anti-parallel fashion with a formation of β-sheet hydrogen bonds between adjacent neutral cyclic peptides.

2. A molecular tube comprising:

a plurality of cyclic peptides, each of said peptides being homodetic and having an amino acid sequence with a length between 6 and 16 amino acid residues, a repeating D-L chirality motif, and an even number of amino acid residues;

each of said cyclic peptides including an ionizable amino acid residue;

said molecular tube being formed in solution by self-assembly induced by neutralization of the ionizable amino acid residue and stacking of said cyclic peptides upon one another in an anti-parallel fashion with a formation of β-sheet hydrogen bonds between adjacent cyclic peptides.

3. A molecular tube as described in claim 2 further comprising:

a terminal cyclic peptide having a ring structure with a first face and a second face, the first face having hydrogen bond donors, the second face being devoid of hydrogen bond donors;

said terminal cyclic peptide forming a terminal end of said molecular tube by stacking the first face thereonto in an anti-parallel fashion with a formation of β-sheet hydrogen bonds.

4. A molecular tube as described in claim 3 wherein the second face of said terminal cyclic peptide has alkyl-block amino groups thereon.

5. A method as described in claim 1 wherein:

in said Step A, all of said ionized amino acid residues are ionized acidic amino acid residues and impart a net negative charge to said charged cyclic peptides; and in said Step B, the net negative charge of said charged cyclic peptides of said Step A is neutralized by protonation by decreasing the pH of the first solution.

6. A method as described in claim 1 wherein:

in said Step A, all of said ionized amino acid residues are ionized basic amino acid residues and impart a net positive charge to said charged cyclic peptides; and in said Step B, the net positive charge of said charged cyclic peptides of said Step A is neutralized by deprotonation by increasing the pH of the first solution.

* * * * *